(12) United States Patent
Tanabe et al.

(10) Patent No.: US 11,912,977 B2
(45) Date of Patent: Feb. 27, 2024

(54) PLURIPOTENT STEM CELL PRODUCTION SYSTEM

(71) Applicants: I Peace, Inc., Palo Alto, CA (US); Koji Tanabe, Palo Alto, CA (US)

(72) Inventors: Koji Tanabe, Palo Alto, CA (US); Brendan Kelly, Palo Alto, CA (US); Kenta Suto, Palo Alto, CA (US); Hidenori Shimoda, Palo Alto, CA (US); Ryoji Hiraide, Palo Alto, CA (US)

(73) Assignee: I Peace, Inc., Palo Alto, CA (US)

( * ) Notice: Subject to any disclaimer, the term of this patent is extended or adjusted under 35 U.S.C. 154(b) by 28 days.

(21) Appl. No.: 17/817,287

(22) Filed: Aug. 3, 2022

(65) Prior Publication Data
US 2022/0389368 A1      Dec. 8, 2022

Related U.S. Application Data

(63) Continuation of application No. 15/756,031, filed as application No. PCT/JP2016/075540 on Aug. 31, 2016, now Pat. No. 11,518,974.
(Continued)

(30) Foreign Application Priority Data

Aug. 31, 2015   (JP) .................. 2015-170797

(51) Int. Cl.
*C12N 5/074*    (2010.01)
*C12M 1/36*     (2006.01)
(Continued)

(52) U.S. Cl.
CPC ............ *C12M 41/48* (2013.01); *C12M 23/28* (2013.01); *C12M 23/44* (2013.01); *C12M 27/00* (2013.01);
(Continued)

(58) Field of Classification Search
CPC ...... C12N 5/0696; C12M 23/58; C12M 23/14
See application file for complete search history.

(56) References Cited

U.S. PATENT DOCUMENTS

| 5,071,760 A | 12/1991 | Watanabe et al. |
| 6,498,690 B2 | 12/2002 | Ramm et al. |
| (Continued) | | |

FOREIGN PATENT DOCUMENTS

| CN | 102174395 A | 9/2011 |
| EP | 1 473 360 A2 | 11/2004 |
| (Continued) | | |

OTHER PUBLICATIONS

"Biotech Cellulose Ester (CE) Membrane: Dialysis Tubing & Dialysis Trial Kits", Spectrum Laboratories, Inc. [online], Apr. 22, 2012 [retrieved Jan. 4, 2017]. Retrieved from the Internet: URL <http://web.archive.org/web/20120422151024/http://www.spectrumlabs.com/dialysis/BiotechTubing.html>, 2 pages.
(Continued)

*Primary Examiner* — Jonathan M Hurst
(74) *Attorney, Agent, or Firm* — Studebaker & Brackett PC

(57) ABSTRACT

A stem cell production system provided with a preintroduction cell-feeding solution channel 20 through which a solution containing cells passes, an induction factor-feeding solution mechanism 21 for feeding a pluripotency induction factor to the preintroduction cell-feeding solution channel 20, a factor introduction device 30 connected to the preintroduction cell-feeding solution channel 20 for making cells with induction factor introduced by introducing the pluripotency induction factor into the cells, a cell mass-making device 40 for making multiple cell masses comprising stem
(Continued)

cells by culturing the cells with induction factor introduced, and a packaging device 100 for sequentially packaging each of the multiple cell masses.

30 Claims, 44 Drawing Sheets

Related U.S. Application Data

(60) Provisional application No. 62/356,199, filed on Jun. 29, 2016.

(51) Int. Cl.

| | |
|---|---|
| C12M 1/00 | (2006.01) |
| C12M 1/34 | (2006.01) |
| C12M 1/33 | (2006.01) |
| C12M 1/42 | (2006.01) |
| C12N 5/078 | (2010.01) |
| C12M 3/00 | (2006.01) |
| C12M 1/02 | (2006.01) |
| C12M 1/12 | (2006.01) |

(52) U.S. Cl.
CPC ............ *C12M 29/00* (2013.01); *C12M 29/04* (2013.01); *C12M 35/00* (2013.01); *C12M 37/02* (2013.01); *C12M 41/12* (2013.01); *C12M 41/36* (2013.01); *C12M 45/02* (2013.01); *C12M 47/04* (2013.01); *C12N 5/0634* (2013.01); *C12N 5/0696* (2013.01)

(56) References Cited

U.S. PATENT DOCUMENTS

| | | | |
|---|---|---|---|
| 2009/0029462 | A1 | 1/2009 | Beardsley et al. |
| 2009/0068742 | A1 | 3/2009 | Yamanaka |
| 2009/0104594 | A1 | 4/2009 | Webb |
| 2009/0191159 | A1 | 7/2009 | Sakurada et al. |
| 2010/0136690 | A1 | 6/2010 | Sundstrom et al. |
| 2011/0281281 | A1 | 11/2011 | Irion |
| 2012/0196358 | A1 | 8/2012 | Burbank et al. |
| 2012/0258536 | A1 | 10/2012 | Aidun et al. |
| 2013/0309710 | A1 | 11/2013 | Nakamura |
| 2013/0345094 | A1 | 12/2013 | Noggle et al. |
| 2014/0106348 | A1 | 4/2014 | Nishino et al. |
| 2014/0220665 | A1 | 8/2014 | King et al. |
| 2014/0248698 | A1 | 9/2014 | Kotera et al. |
| 2014/0287509 | A1 | 9/2014 | Sharei et al. |
| 2014/0315311 | A1 | 10/2014 | Miltenyi et al. |
| 2014/0329317 | A1 | 11/2014 | Nakatsuji |
| 2015/0159127 | A1 | 6/2015 | Guerini et al. |
| 2016/0060588 | A1 | 3/2016 | Nakatsuji et al. |
| 2016/0272929 | A1 | 9/2016 | Fuji et al. |
| 2017/0306279 | A1 | 10/2017 | Kagawa et al. |
| 2018/0169148 | A1 | 6/2018 | Adair et al. |

FOREIGN PATENT DOCUMENTS

| | | |
|---|---|---|
| JP | 2006-014693 A | 1/2006 |
| JP | 2007-000038 A | 1/2007 |
| JP | 2008-526203 A | 7/2008 |
| JP | 4183742 B1 | 11/2008 |
| JP | 2010-532173 A | 10/2010 |
| JP | 2015-092849 A | 5/2015 |
| WO | 2009/106760 A2 | 9/2009 |
| WO | 2009/106760 A3 | 5/2010 |
| WO | 2012/115153 A1 | 8/2012 |
| WO | 2013/077423 A1 | 5/2013 |
| WO | 2013/094365 A1 | 6/2013 |
| WO | 2013/136372 A1 | 9/2013 |
| WO | 2014/136581 A1 | 9/2014 |
| WO | 2014/144789 A2 | 9/2014 |
| WO | 2016/117615 A1 | 7/2016 |

OTHER PUBLICATIONS

Chanda et al., "Generation of Induced Neuronal Cells by the Single Reprogramming Factor ASCLI", Stem Cell Reports. Aug. 12, 2014;3(2):282-96. Epub Jul. 4, 2014.

Fusaki et al., "Efficient induction of transgene-free human pluripotent stem cells using a vector based on Sendai virus, an RNA virus that does not integrate into the host genome", Proc Jpn Acad Ser B Phys Biol Sci. 2009;85(8):348-62.

Hacein-Bey-Abina et al., "LM02-Associated Clonal T Cell Proliferation in Two Patients after Gene Therapy for SCID-X1", Science. Oct. 17, 2003;302(5644):415-9.

Hacein-Bey-Abina et al., "Sustained correction of X-linked severe combined immunodeficiency by ex vivo gene therapy", N Engl J Med. Apr. 18, 2002;346(16):1185-93.

Hamot et al., "Method validation for automated isolation of viable peripheral blood mononuclear cells", Biopreserv Biobank. Jun. 2015;13(3):152-63. Epub Apr. 1, 2015.

Ishii et al., "Novel cultivation method development for suspension culture of pluripotent stem cell", BIO Clinica. May 2015;30(5):82-86.

"Lipofectamine® MessengerMAX™", Thermo Fisher Scientific [online], Aug. 25, 2015 [retrieved Jan. 3, 2017]. Retrieved from the Internet: URL <http://web.archive.org/web/20150825014508/ http:// www.thermofisher.com/us/en/home/brands/product-brand/lipofecta mine/lipofecta mine-messengermax.html>, 5 pages.

Ohnuki et al., "Dynamic regulation of human endogenous retroviruses mediates factor-induced reprogramming and differentiation potential", Proc Natl Acad Sci U S A. Aug. 26, 2014;111(34):12426-31. Epub Aug. 5, 2014.

Okita et al., "Generation of germline-competent induced pluripotent stem cells", Nature. Jul. 19, 2007;448(7151):313-7. Epub Jun. 6, 2007.

Osafune et al., "Marked differences in differentiation propensity among human embryonic stem cell lines", Nat Biotechnol. Mar. 2008;26(3):313-5. Epub Feb. 17, 2008.

Ujam et al., "Isolation of monocytes from human peripheral blood using immuno-affinity expanded-bed adsorption", Biotechnol Bioeng. Sep. 5, 2003;83(5):554-66.

Yu et al., "Human Induced Pluripotent Stem Cells Free of Vector and Transgene Sequences", Science. May 8, 2009;324(5928):797-801. Epub Mar. 26, 2009.

Fig. 32A
Fig. 32B
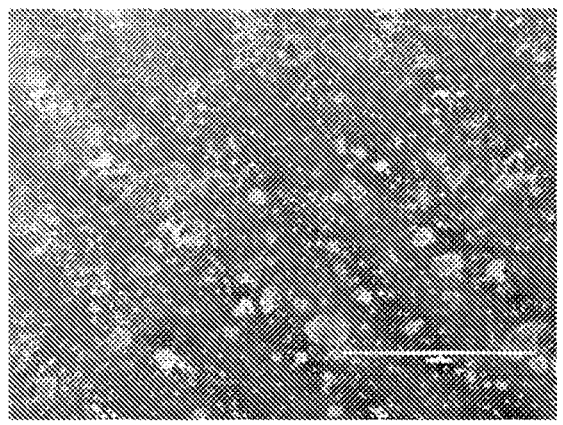
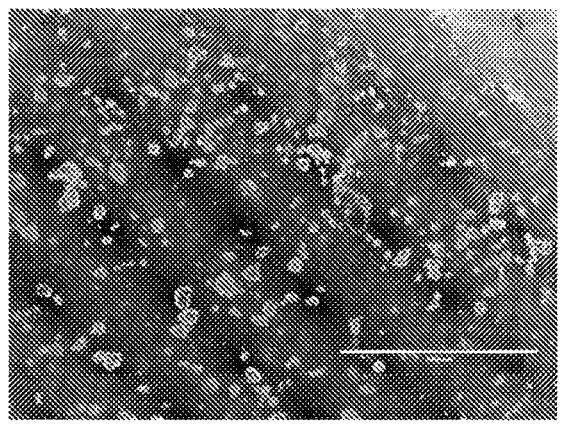

Suspension culturing with gelled medium  Suspension culturing with non-gelled medium 1st day 9th day Colonies before reseeding on feeder cells Colonies 3 days after reseeding on feeder cells With dialysis tube
With medium exchange With dialysis tube
Without medium exchange Without dialysis tube
Without medium exchange

PLURIPOTENT STEM CELL PRODUCTION SYSTEM

CROSS-REFERENCE TO RELATED APPLICATIONS

This application is a Continuation of U.S. patent application Ser. No. 15/756,031, filed Feb. 27, 2018, which is the U.S. National Stage of International Application No. PCT/JP2016/075540, filed Aug. 31, 2016, which claims the benefit of priority to U.S. Provisional Patent Application No. 62/356,199, filed Jun. 29, 2016, and the benefit of priority of Japanese Patent Application No. 2015-170797, filed on Aug. 31, 2015, the entire contents of which are incorporated herein by reference.

TECHNICAL FIELD

The present invention relates to cell preservation technology, and particularly to a pluripotent stem cell production system.

BACKGROUND ART

Embryonic stem cells (ES cells) are stem cells established from early embryos of human or mice. ES cells are pluripotent, being capable of differentiating into all cells in the body. At the current time, human ES cells are usable in cell transplantation therapy for numerous diseases including Parkinson's disease, juvenile onset diabetes and leukemia. However, barriers exist against transplantation of ES cells. In particular, transplantation of ES cells can provoke immunorejection similar to the rejection encountered after unsuccessful organ transplantation. Moreover, there are many ethical considerations as well as critical and dissenting opinions against the use of ES cell lines that have been established by destruction of human embryos.

It was against this background that Professor Shinya Yamanaka of Kyoto University was successful in establishing induced pluripotent stem cells (iPS cells) by transferring four genes: Oct3/4, Klf4, c-Myc and Sox2, into somatic cells. For this, Professor Yamanaka received the Nobel Prize in Physiology or Medicine in 2012 (see PTL 1, for example). iPS cells are ideal pluripotent cells free of the issues of rejection or ethical problems. Therefore, iPS cells are considered promising for use in cell transplantation therapy.

CITATION LIST

Patent Literature

PTL 1: Japanese Patent Publication No. 4183742

SUMMARY OF INVENTION

Technical Problem

Induced stem cells such as iPS cells are established by introducing inducing factors such as genes into cells which are then subjected to amplifying culturing and cryopreservation. However, the following problems are involved in the preparation and industrialization of iPS cells for clinical use (for example, GLP or GMP grade).
1) Cost
iPS cells for clinical use must be prepared and stored in a cleanroom kept in a state of very high cleanliness. The cost for maintaining the required level of cleanliness, however, is extremely high. The preparation of iPS cells is therefore very costly, and this has been a great hindrance against industrialization.
2) Quality
The series of operations from establishment of stem cells to their storage are complex, and many of them must be carried out by hand. Moreover, the preparation of stem cells often depends on a personal level of skill. Therefore, the quality of iPS cells varies depending on the preparer and on the particular experimental batch.
3) Time
In order to prevent cross-contamination with iPS cells other than those of a particular donor in the cleanroom, iPS cells from only a single individual are prepared in the same cleanroom over a prescribed period of time. In addition, long time periods are necessary to establish iPS cells and evaluate their quality. However, since iPS cells are only prepared once for a single individual in the cleanroom, a very long period of time is required to prepare iPS cells for many different individuals.
4) Personnel
As mentioned above, currently the preparation of iPS cells is for a large part carried out by hand. Nevertheless, few technicians have the skills necessary for them to prepare iPS cells for clinical use.

It is a problem that the series of operations from establishment of stem cells to their storage are complex. To counter this problem, it is an object of the present invention to provide a stem cell production system that allows production of stem cells.

Solution to Problem

According to one aspect of the invention there is provided a stem cell production system comprising a preintroduction cell solution-feeding channel through which a cell-containing solution passes, a factor introducing device connected to the preintroduction cell solution-feeding channel, that introduces pluripotency inducing factors into cells to prepare inducing factor-introduced cells, a cell mass preparation device that cultures the inducing factor-introduced cells to prepare a plurality of cell masses comprising stem cells, and an enclosure that houses the preintroduction cell solution-feeding channel, inducing factor solution-feeding mechanism, factor introducing device and cell mass preparation device, wherein the cell mass preparation device comprises an initializing culturing apparatus that cultures the inducing factor-introduced cells that have been prepared by the factor introducing device, and an amplifying culturing apparatus that carries out amplifying culturing of the plurality of cell masses comprising stem cells that have been established by the initializing culturing apparatus, the initializing culturing apparatus comprises a first culture medium supply device that supplies culture medium to the inducing factor-introduced cells, and the amplifying culturing apparatus comprises a second culture medium supply device that supplies culture medium to the plurality of cell masses.

In the stem cell production system described above, the first culture medium supply device may also supply culture medium to the inducing factor-introduced cells in a continuous manner.

In the stem cell production system described above, the first culture medium supply device may also supply culture medium to the inducing factor-introduced cells at a prescribed timing.

In the stem cell production system described above, the second culture medium supply device may also supply culture medium to the plurality of cell masses in a continuous manner.

In the stem cell production system described above, the second culture medium supply device may also supply culture medium to the plurality of cell masses at a prescribed timing.

In the stem cell production system described above, the factor introducing device may also comprise a factor introducing device connected to the preintroduction cell solution-feeding channel, a factor storing device that stores the pluripotency inducing factors, a factor solution-feeding channel for streaming of the pluripotency inducing factors from the factor storing device to the factor introducing device, and a pump for streaming of the liquid in the factor solution-feeding channel.

In the stem cell production system described above, the pluripotency inducing factors may be introduced into the cells by RNA lipofection at the factor introducing device.

In the stem cell production system described above, the pluripotency inducing factor may be DNA, RNA or protein.

In the stem cell production system described above, the pluripotency inducing factors may be incorporated into a vector.

In the stem cell production system described above, the vector may be Sendai virus vector.

In the stem cell production system described above, the pump may be a diaphragm pump, a tubing pump or Peristaltic Pump®.

In the stem cell production system described above, the initializing culturing apparatus may also comprise a suspension culture vessel that comprises a dialysis tube in which the inducing factor-introduced cells and gel medium have been inserted, and a vessel in which the dialysis tube is placed and the gel medium is situated around the periphery of the dialysis tube.

In the stem cell production system described above, the molecular cutoff of the dialysis tube may be 0.1 KDa or greater.

In the stem cell production system described above, the dialysis tube may be made of at least one material selected from among cellulose esters, cellulose ester derivatives, regenerated cellulose and cellulose acetate.

In the stem cell production system described above, the first culture medium supply device may supply the gel medium to the periphery of the dialysis tube in the vessel.

In the stem cell production system described above, the first culture medium supply device may supply the gel medium into the dialysis tube.

The stem cell production system described above may further comprise a culture medium solution-feeding channel through which the supplied gel medium flows.

In the stem cell production system described above, the culture medium solution-feeding channel may be carbon dioxide-permeable.

The stem cell production system described above may further comprise a pump for streaming of liquid in the culture medium solution-feeding channel.

In the stem cell production system described above, the pump may be a diaphragm pump, a tubing pump or a Peristaltic Pump®.

The stem cell production system described above may further comprise a cold storage section in which the supplied gel medium is kept in cold storage.

The stem cell production system described above may further comprise a waste liquid solution-feeding channel connected to the vessel, the waste liquid solution-feeding channel serving for discharge of the gel medium in the vessel to the outside.

The stem cell production system described above may further comprise an introduced cell solution-feeding channel for delivery of the inducing factor-introduced cells from the factor introducing device to the initializing culturing apparatus.

In the stem cell production system described above, the introduced cell solution-feeding channel may be carbon dioxide-permeable.

The stem cell production system described above may further comprise a pump for streaming of liquid in the introduced cell solution-feeding channel.

In the stem cell production system described above, the pump may be a diaphragm pump, a tubing pump or a Peristaltic Pump®.

In the stem cell production system described above, the amplifying culturing apparatus may also comprise a suspension culture vessel that comprises a dialysis tube in which the plurality of cell masses and gel medium have been inserted, and a vessel in which the dialysis tube is inserted and the gel medium is inserted surrounding the dialysis tube.

In the stem cell production system described above, the molecular cutoff of the dialysis tube may be 0.1 KDa or greater.

In the stem cell production system described above, the dialysis tube is made of at least one material selected from among cellulose esters, cellulose ester derivatives, regenerated cellulose and cellulose acetate.

In the stem cell production system described above, the second culture medium supply device may supply the gel medium to the periphery of the dialysis tube in the vessel.

In the stem cell production system described above, the second culture medium supply device may supply the gel medium into the dialysis tube.

The stem cell production system described above may further comprise a culture medium solution-feeding channel through which the supplied gel medium flows.

In the stem cell production system described above, the culture medium solution-feeding channel may be carbon dioxide-permeable.

The stem cell production system described above may further comprise a pump for streaming of liquid in the culture medium solution-feeding channel.

In the stem cell production system described above, the pump may be a diaphragm pump, a tubing pump or a Peristaltic Pump®.

The stem cell production system described above may further comprise a cold storage section in which the supplied gel medium is kept in cold storage.

The stem cell production system described above may further comprise a waste liquid solution-feeding channel connected to the vessel, the waste liquid solution-feeding channel serving for discharge of the gel medium in the vessel to the outside.

The stem cell production system described above may further comprise an introduced cell solution-feeding channel for delivery of the inducing factor-introduced cells from the initializing culturing apparatus to the amplifying culturing apparatus.

The stem cell production system described above may further comprise an introduced cell solution-feeding channel that connects inside of the dialysis tube of the suspension culture vessel of the initializing culturing apparatus with the inside of the dialysis tube of the suspension culture vessel of the amplifying culturing apparatus.

In the stem cell production system described above, the introduced cell solution-feeding channel may be carbon dioxide-permeable.

The stem cell production system described above may further comprise a pump for streaming of liquid in the introduced cell solution-feeding channel.

In the stem cell production system described above, the pump may be a diaphragm pump, a tubing pump or a Peristaltic Pump®.

In the stem cell production system described above, either or both the initializing culturing apparatus and the amplifying culturing apparatus may comprise a carbon dioxide-permeable bag in which a culture medium is to be placed.

In the stem cell production system described above, the cell mass preparation device may further comprise a first dissociating mechanism that dissociates a cell mass comprising stem cells established in the initializing culturing apparatus, into a plurality of cell masses, and a second dissociating mechanism that dissociates the cell mass comprising stem cells that have undergone amplifying culturing in the amplifying culturing apparatus, into a plurality of cell masses.

In the stem cell production system described above, the first dissociating mechanism may be provided in the introduced cell solution-feeding channel that serves for delivery of the inducing factor-introduced cells from the initializing culturing apparatus to the amplifying culturing apparatus.

In the stem cell production system described above, either or both the first and second dissociating mechanisms may dissociate the cell mass into single cells.

In the stem cell production system described above, either or both the first and second dissociating mechanisms may comprise a dissociator having a through-hole in the interior, the through-hole may have large pore size sections and small pore size sections connecting with the large pore size sections and having smaller pore sizes than the large pore size sections, in an alternating manner, and the cell mass-containing culture medium may flow through the through-hole.

In the stem cell production system described above, the central axes of the large pore size sections and the central axes of the small pore size sections may be offset.

In the stem cell production system described above, either or both the first and second dissociating mechanisms each comprise a connecting block with a through-hole provided in the interior, a recess is provided at the first edge of the connecting block and a protrusion is provided at the second edge of the connecting block, in the case of multiple connecting blocks, the protrusions engage with the recesses of the adjacent connecting blocks, and the through-hole has a first large pore size section that connects with the recess, a small pore size section that connects with the first large pore size section and has a smaller pore size than the first large pore size section, and a second large pore size section that connects with the small pore size section, has a larger pore size than the small pore size section and has an opening at the tip of the protrusion, wherein the cell mass-containing culture medium may flow through the through-hole.

In the stem cell production system described above, when multiple connecting blocks are present and the multiple connecting blocks are connected, the second large pore size sections may be smoothly connecting with the first large pore size sections of adjacent connecting blocks.

In the stem cell production system described above, the central axes of the first and second large pore size sections and the central axis of the small pore size section may be offset.

In the stem cell production system described above, the first and second dissociating mechanisms may each further comprise a tip block with a through-hole provided in the interior, a recess may be provided at the first edge of the tip block and a nozzle at the second edge of the tip block, the recess of the tip block may be engaged with the protrusion of the connecting block, and the through-hole may have a large pore size section that connects with the recess, and a small pore size section that connects with the large pore size section, has a smaller pore size than the large pore size section and has an opening at the tip of the nozzle.

In the stem cell production system described above, when the connecting block and the tip block have been connected, the second large pore size section of the connecting block and the large pore size section of the tip block may be smoothly connecting.

In the stem cell production system described above, the first and second dissociating mechanisms may each further comprise a terminal block with a through-hole provided in the interior, a recess may be provided at the first edge of the terminal block and a protrusion at the second edge of the terminal block, and the protrusion of the terminal block may be engaged with the recess of the connecting block.

In the stem cell production system described above, the first and second dissociating mechanisms may each further comprise an insertion nozzle that is inserted in the recess of the terminal block, and a suction drainer in connection with the insertion nozzle, that suction drains the cell mass-containing culture medium.

In the stem cell production system described above, there may be further provided a packaging device that packages each of the plurality of cell masses in order, and the enclosure may house the packaging device.

In the stem cell production system described above, the cell mass preparation device may further comprise a cell mass transport mechanism that successively delivers the plurality of cell masses to the packaging device.

In the stem cell production system described above, the packaging device may freeze the cell masses using a Peltier element or liquid nitrogen.

In the stem cell production system described above, the packaging device may also freeze the cell masses by evaporative compression or evaporative absorption.

The stem cell production system described above may further comprise a solution exchanger comprising a tubular component and a liquid permeable filter disposed inside the tubular component, the solution exchanger being provided with, in the tubular component, a cell mass introduction hole for introduction of solution including a plurality of cell masses onto the liquid permeable filter, an exchange solution introduction hole for introduction of exchange solution onto the liquid permeable filter, a cell mass outflow hole for outflow of the exchange solution including the plurality of cell masses onto the liquid permeable filter, and a waste liquid outflow hole through which the solution that has permeated the liquid permeable filter flows out.

The stem cell production system described above may further comprise a waste liquid solution-feeding channel connected to the waste liquid outflow hole, permitting the solution containing the plurality of cell masses to flow through the waste liquid solution-feeding channel when the solution is discarded, and not permitting the solution to flow through the waste liquid solution-feeding channel when the plurality of cell masses are being dispersed in the exchange solution.

In the stem cell production system described above, the exchange solution may be culture medium, a cryopreservation liquid, or a cell mass dissociating enzyme solution.

The stem cell production system described above may further comprise an introduced cell solution-feeding channel for delivery of the plurality of cell masses from the amplifying culturing apparatus to the solution exchanger.

The stem cell production system described above may further comprise an introduced cell solution-feeding channel connecting the inside of the dialysis tube of the suspension culture vessel of the amplifying culturing apparatus with the cell mass introduction hole of the solution exchanger.

In the stem cell production system described above, the introduced cell solution-feeding channel may be carbon dioxide-permeable.

The stem cell production system described above may further comprise a pump for streaming of liquid in the introduced cell solution-feeding channel.

In the stem cell production system described above, the pump may be a diaphragm pump, a tubing pump or a Peristaltic Pump®.

The stem cell production system described above may further comprise a separating device that separates cells from blood, and the cell-containing solution separated by the separating device may pass through the preintroduction cell solution-feeding channel.

In the stem cell production system described above, the separating device may separate mononuclear cells from blood by a magnetic cell separation method or a method using an erythrocyte coagulant.

In the stem cell production system described above, the separating device may further comprise a mononuclear cell purifying filter that purifies mononuclear cells.

The stem cell production system described above may further comprise a pump for streaming of liquid in the preintroduction cell solution-feeding channel.

In the stem cell production system described above, the pump may be a diaphragm pump, a tubing pump or a Peristaltic Pump®.

The stem cell production system described above may further comprise a case that houses at least one from among the factor introducing device, the suspension culture vessel of the initializing culturing apparatus and the suspension culture vessel of the amplifying culturing apparatus, the case being disposed in the enclosure.

In the stem cell production system described above, the suspension culture vessel of the initializing culturing apparatus, the suspension culture vessel of the amplifying culturing apparatus and the case may be disposable.

The stem cell production system described above may further comprise a case that houses at least one from among the separating device, the factor introducing device, the suspension culture vessel of the initializing culturing apparatus, the suspension culture vessel of the amplifying culturing apparatus and the solution exchanger, the case being disposed in the enclosure.

In the stem cell production system described above, the separating device, the factor introducing device, the suspension culture vessel of the initializing culturing apparatus, the suspension culture vessel of the amplifying culturing apparatus, the solution exchanger and the case may be disposable.

The stem cell production system described above may further comprise a plurality of cases disposed in the enclosure, at least one from among the factor introducing device, the suspension culture vessel of the initializing culturing apparatus and the suspension culture vessel of the amplifying culturing apparatus being housed in each of the plurality of cases.

In the stem cell production system described above, the suspension culture vessel of the initializing culturing apparatus, the suspension culture vessel of the amplifying culturing apparatus and the plurality of cases may be disposable.

The stem cell production system described above may further comprise a plurality of cases disposed in the enclosure, at least one from among the separating device, the factor introducing device, the suspension culture vessel of the initializing culturing apparatus, the suspension culture vessel of the amplifying culturing apparatus and the solution exchanger being housed in each of the plurality of cases.

In the stem cell production system described above, the separating device, the factor introducing device, the suspension culture vessel of the initializing culturing apparatus, the suspension culture vessel of the amplifying culturing apparatus, the solution exchanger and the plurality of cases may be disposable.

In the stem cell production system described above, the case and the enclosure may comprise engaging parts that mutually engage, and the case may be disposed at a prescribed location in the enclosure.

In the stem cell production system described above, when the case is disposed in the enclosure, the solution-feeding channel inside the case and the pump outside the case may be connected.

In the stem cell production system described above, when the case is disposed in the enclosure, the factor introducing device inside the case and the factor storing device outside the case may be connected.

In the stem cell production system described above, when the case is disposed in the enclosure, the suspension culture vessel of the initializing culturing apparatus and the suspension culture vessel of the amplifying culturing apparatus inside the case, and a culture medium storing unit that stores culture medium outside the case, may be connected.

In the stem cell production system described above, when the case is disposed in the enclosure, the suspension culture vessel of the initializing culturing apparatus and the suspension culture vessel of the amplifying culturing apparatus inside the case, and a waste liquid storage section that stores waste liquid outside the case, may be connected.

In the stem cell production system described above, when the case is disposed in the enclosure, the separating device inside the case and a blood storing unit that stores blood outside the case, may be connected.

In the stem cell production system described above, when the case is disposed in the enclosure, the separating device inside the case and a separating agent storing device that stores a blood separating agent outside the case, may be connected.

In the stem cell production system described above, when the case is disposed in the enclosure, the solution exchanger inside the case and a cryopreservation liquid storing device that stores cryopreservation liquid outside the case, may be connected.

The stem cell production system described above may further comprise an initializing culturing photographing device that photographs cells cultured in the initializing culturing apparatus, and an amplifying culturing photographing device that photographs cells cultured in the amplifying culturing apparatus.

In the stem cell production system described above, the initializing culturing photographing device and the amplifying culturing photographing device may each photograph the cells through a telecentric lens.

The stem cell production system described above may further comprise an image processor that applies a highpass filter to the image obtained from either or both the initializing culturing photographing device and the amplifying culturing photographing device.

In the stem cell production system described above, the image processor may apply a watershed algorithm to the image to which the highpass filter has been applied, to extract the cell masses in the image.

In the stem cell production system described above, the image processor may also apply a Distance Transform method to the image before applying a watershed algorithm to the image.

In the stem cell production system described above, the image processor may calculate the sizes of the extracted cell masses.

In the stem cell production system described above, when the cell mass sizes that have been calculated from the image photographed by the initializing culturing photographing device are above a threshold value, the plurality of cell masses comprising stem cells that have been established in the initializing culturing apparatus may be moved to the amplifying culturing apparatus.

In the stem cell production system described above, when the cell mass sizes that have been calculated from the image photographed by the amplifying culturing photographing device are above a threshold value, the plurality of cell masses may be subcultured in the amplifying culturing apparatus.

In the stem cell production system described above, the supply rate of culture medium in the initializing culturing apparatus may be varied according to the cell mass sizes calculated from the image photographed by the initializing culturing photographing device.

In the stem cell production system described above, the supply rate of culture medium in the amplifying culturing apparatus may be varied according to the cell mass sizes calculated from the image photographed by the amplifying culturing photographing device.

In the stem cell production system described above, the image processor may calculate the number of extracted cell masses.

In the stem cell production system described above, the supply rate of culture medium in the initializing culturing apparatus may be varied according to the cell mass number calculated from the image photographed by the initializing culturing photographing device.

In the stem cell production system described above, the supply rate of culture medium in the amplifying culturing apparatus may be varied according to the cell mass number calculated from the image photographed by the amplifying culturing photographing device.

The stem cell production system described above may further comprise a relationship memory unit that stores the relationship between the turbidity of the culture medium and the density of cell masses in the culture medium, and it may still further comprise an image processor that calculates the value of the turbidity of the culture medium in which the cells are being cultured, based on the image obtained from either or both the initializing culturing photographing device and the amplifying culturing photographing device, and, based on the calculated turbidity value and the relationship, calculates the value of the density of cell masses that have been photographed.

In the stem cell production system described above, when the cell mass density that has been calculated from the image photographed by the initializing culturing photographing device is above a threshold value, the plurality of cell masses comprising stem cells that have been established in the initializing culturing apparatus may be moved to the amplifying culturing apparatus.

In the stem cell production system described above, when the cell mass density that has been calculated from the image photographed by the amplifying culturing photographing device is above a threshold value, the plurality of cell masses may be subcultured in the amplifying culturing photographing device.

In the stem cell production system described above, the supply rate of culture medium in the initializing culturing apparatus may be varied according to the cell mass density calculated from the image photographed by the initializing culturing photographing device.

In the stem cell production system described above, the supply rate of culture medium in the amplifying culturing apparatus may be varied according to the cell mass density calculated from the image photographed by the amplifying culturing photographing device.

The stem cell production system described above may further comprise a relationship memory unit that stores the relationship between the color of the culture medium and the hydrogen ion exponent of the culture medium, and it may still further comprise an image processor that calculates the value of the color of the culture medium in the image obtained from either or both the initializing culturing photographing device and the amplifying culturing photographing device, and, based on the calculated color value and the relationship, calculates the value of the hydrogen ion exponent of the culture medium that has been photographed.

In the stem cell production system described above, when the hydrogen ion exponent calculated from the image photographed by the initializing culturing photographing device is outside of a prescribed range, the culture medium in the initializing culturing apparatus may be exchanged.

In the stem cell production system described above, when the hydrogen ion exponent calculated from the image photographed by the amplifying culturing photographing device is outside of a prescribed range, the culture medium in the amplifying culturing apparatus may be exchanged.

In the stem cell production system described above, the color of the culture medium may be the hue of the culture medium.

In the stem cell production system described above, when the hydrogen ion exponent measured by the initializing culturing apparatus is outside of a prescribed range, the culture medium in the initializing culturing apparatus may be exchanged.

In the stem cell production system described above, when the hydrogen ion exponent measured by the amplifying culturing apparatus is outside of a prescribed range, the culture medium in the amplifying culturing apparatus may be exchanged.

In the stem cell production system described above, the inner wall of the preintroduction cell solution-feeding channel may be non-cell-adherent.

In the stem cell production system described above, the preintroduction cell solution-feeding channel and the inducing factor solution-feeding mechanism may be provided on a substrate.

The stem cell production system described above may further comprise an air purifier that purifies the gas in the enclosure.

The stem cell production system described above may further comprise a temperature regulating device that regulates the temperature of the gas in the enclosure.

The stem cell production system described above may further comprise a temperature regulating device that regulates the temperature of the culture medium in the initializing culturing apparatus and the amplifying culturing apparatus.

In the stem cell production system described above, the temperature regulating device may raise the temperature of the culture medium when the temperature of the culture medium is lower than a prescribed range, and it may lower the temperature of the culture medium when the temperature of the culture medium is higher than a prescribed range.

The stem cell production system described above may further comprise a carbon dioxide concentration control device that controls the carbon dioxide concentration of the gas in the enclosure.

The stem cell production system described above may further comprise a sterilizing device that carries out dry heat sterilization or gas sterilization inside the enclosure.

In the stem cell production system described above, the inducing factor solution-feeding mechanism, the factor introducing device and the cell mass preparation device may be controlled based on an operation procedure by a server, and the server may monitor whether or not the inducing factor solution-feeding mechanism, the factor introducing device and the cell mass preparation device are running based on the operation procedure, and may create a running record of it.

According to this aspect of the invention, there is provided a cell mass dissociator comprising a connecting block provided in its interior with a through-hole through which a cell mass-containing culture medium flows, wherein a recess is provided at the first edge of the connecting block and a protrusion is provided at the second edge of the connecting block, in the case of multiple connecting blocks, the protrusions engage with the recesses of the adjacent connecting blocks, and the through-hole has a first large pore size section that connects with the recess, a small pore size section that connects with the first large pore size section and has a smaller pore size than the first large pore size section, and a second large pore size section that connects with the small pore size section, has a larger pore size than the small pore size section and has an opening at the tip of the protrusion.

In the cell mass dissociator described above, when multiple connecting blocks are present and the multiple connecting blocks are connected, the second large pore size sections may be smoothly connecting with the first large pore size sections of adjacent connecting blocks.

In the cell mass dissociator described above, the central axes of the first and second large pore size sections and the central axes of the small pore size sections may be offset.

In the cell mass dissociator described above, the first and second dissociating mechanisms may each further comprise a tip block with a through-hole provided in the interior, a recess may be provided at the first edge of the tip block and a nozzle at the second edge of the tip block, the recess of the tip block may be engaged with the protrusion of the connecting block, and the through-hole may have a large pore size section that connects with the recess, and a small pore size section that connects with the large pore size section, has a smaller pore size than the large pore size section and has an opening at the tip of the nozzle.

In the cell mass dissociator described above, when the connecting block and the tip block have been connected, the second large pore size section of the connecting block and the large pore size section of the tip block may be smoothly connecting.

The cell mass dissociator described above may further comprise a terminal block with a through-hole provided in the interior, a recess may be provided at the first edge of the terminal block and a protrusion at the second edge of the terminal block, and the protrusion of the terminal block may be engaged with the recess of the connecting block.

The cell mass dissociator described above may further comprise an insertion nozzle that is inserted in the recess of the terminal block, and a suction drainer in connection with the insertion nozzle, that suction drains the cell mass-containing culture medium.

According to another aspect of the invention there is provided a stem cell production system comprising a photographing device that photographs cultured cells, and an image processor that applies a highpass filter to the image obtained by the photographing device.

In the stem cell production system described above, the photographing device may photograph the cells through a telecentric lens.

In the stem cell production system described above, the image processor may apply a watershed algorithm to the image to which the highpass filter has been applied, to extract the cell masses in the image.

In the stem cell production system described above, the image processor may also apply a Distance Transform method to the image before applying a watershed algorithm to the image.

In the stem cell production system described above, the image processor may calculate the sizes of the extracted cell masses.

In the stem cell production system described above, when the cell mass sizes that have been calculated from the image photographed by the photographing device are above a threshold value, the plurality of cell masses comprising stem cells that have been established in the initializing culturing may be moved to the amplifying culturing.

In the stem cell production system described above, when the cell mass sizes that have been calculated from the image photographed by the photographing device are above a threshold value, the plurality of cell masses may be subcultured in the amplifying culturing.

In the stem cell production system described above, the supply rate of culture medium in the culturing vessel may be varied according to the cell mass sizes calculated from the image photographed by the photographing device.

In the stem cell production system described above, the image processor may calculate the number of extracted cell masses.

In the stem cell production system described above, the supply rate of culture medium in the culturing vessel may be varied according to the cell mass number calculated from the image photographed by the photographing device.

According to another aspect of the invention there is provided a stem cell production system comprising a photographing device that photographs cultured cells, a relationship memory unit that stores the relationship between the turbidity of the culture medium and the density of cell masses in the culture medium, and an image processor that calculates the value of the turbidity of the culture medium in which the cells are being cultured, based on the image obtained from the photographing device, and, based on the calculated turbidity value and the relationship, calculates the value of the density of cell masses that have been photographed.

In the stem cell production system described above, the photographing device may photograph the cells through a telecentric lens.

In the stem cell production system described above, when the cell mass density that has been calculated from the image photographed by the photographing device is above a threshold value, the plurality of cell masses comprising stem cells that have been established in the initializing culturing may be moved to the amplifying culturing.

In the stem cell production system described above, when the cell mass density that has been calculated from the image photographed by the photographing device is above a threshold value, the plurality of cell masses may be subcultured in the amplifying culturing.

In the stem cell production system described above, the supply rate of culture medium in the culturing vessel may be varied according to the cell mass density calculated from the image photographed by the photographing device.

According to another aspect of the invention there is provided a stem cell production system comprising a photographing device that photographs cultured cells, a relationship memory unit that stores the relationship between the color of the culture medium and the hydrogen ion exponent of the culture medium, and an image processor that calculates the value of the color of the culture medium in the image obtained from the photographing device, and, based on the calculated color value and the relationship, calculates the value of the hydrogen ion exponent of the culture medium that has been photographed.

In the stem cell production system described above, when the hydrogen ion exponent calculated from the image photographed by the photographing device is outside of a prescribed range, the culture medium in the culturing vessel may be exchanged.

In the stem cell production system described above, the color of the culture medium may be the hue of the culture medium.

Advantageous Effects of Invention

According to the invention it is possible to provide a stem cell production system that allows production of stem cells.

BRIEF DESCRIPTION OF DRAWINGS

FIGS. 32A and 32B is an example of images of dissociated cell masses, according to an embodiment of the invention.

DESCRIPTION OF EMBODIMENTS

Figure 1:
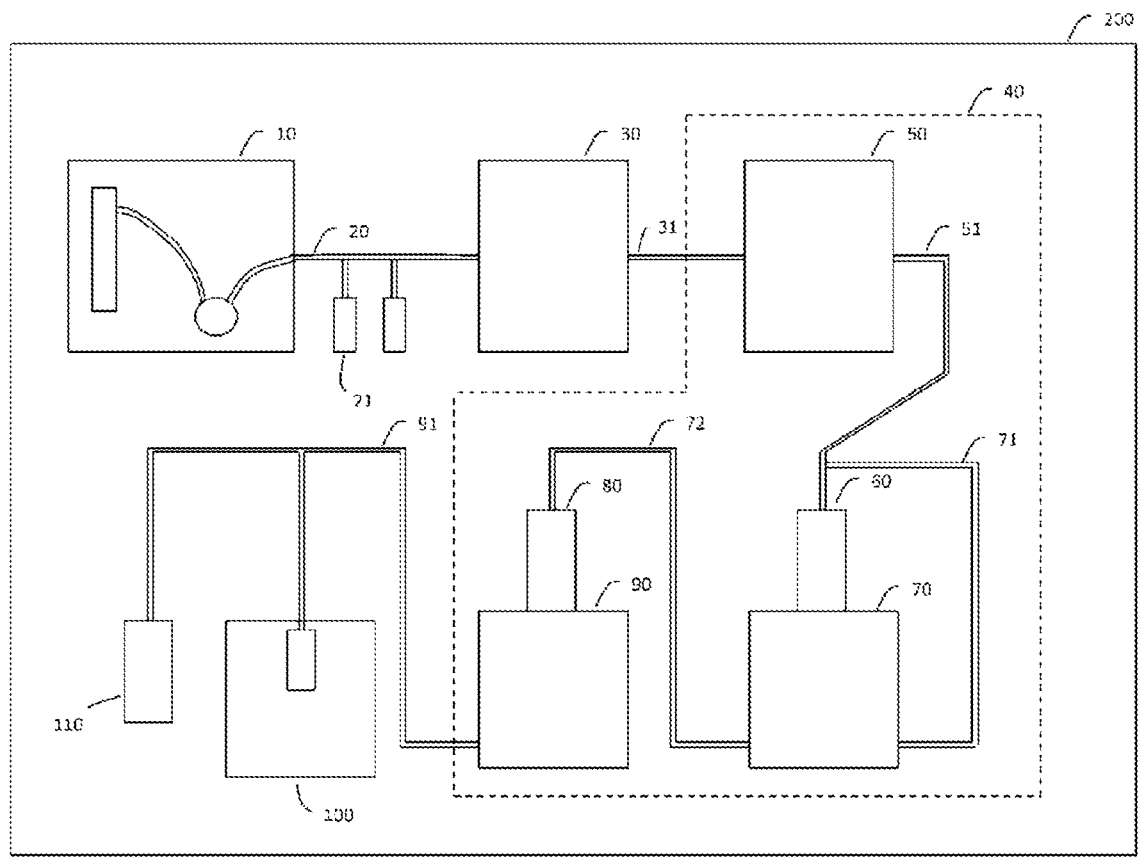
FIG. 1 is a schematic view of a stem cell production system according to an embodiment of the invention.

An embodiment of the invention will now be explained. In the accompanying drawings, identical or similar parts will be indicated by identical or similar reference numerals. However, the drawings are schematic representations. The specific dimensions, therefore, should be judged in light of the following explanation. Furthermore, this naturally includes parts that have different dimensional relationships and proportions between drawings.

The stem cell production system according to an embodiment of the invention comprises, as shown in FIG. 1, a separating device 10 that separates cells from blood, a preintroduction cell solution-feeding channel 20 through which a solution containing cells that have been separated by the separating device 10 passes, an inducing factor solution-feeding mechanism 21 that delivers pluripotency inducing factors into the preintroduction cell solution-feeding channel 20, a factor introducing device 30 connected to the preintroduction cell solution-feeding channel 20, that introduces the pluripotency inducing factors to the cells to prepare inducing factor-introduced cells, a cell mass preparation device 40 that cultures the inducing factor-introduced cells to prepare a plurality of cell masses comprising stem cells, and a packaging device 100 that packages each of the plurality of cell masses in order.

The stem cell production system further comprises a miniature enclosure 200 that houses the separating device 10, the preintroduction cell solution-feeding channel 20, the inducing factor solution-feeding mechanism 21, the factor introducing device 30, the cell mass preparation device 40 and the packaging device 100.

The stem cell production system still further comprises an air purifier that purifies the gas in the enclosure 200, a temperature regulating device that regulates the temperature of the gas in the enclosure 200, and a carbon dioxide concentration control device that controls the concentration of carbon dioxide ($CO_2$) in the gas in the enclosure 200. The air purifier may also comprise a cleanliness sensor that monitors the cleanliness of the gas in the enclosure 200. The air purifier purifies the air in the enclosure 200 using a HEPA (High Efficiency Particulate Air) filter, for example. The air purifier purifies the air in the enclosure 200 to a cleanliness conforming to ISO standard 14644-1, class ISO1 to ISO6, for example. The temperature regulating device may also comprise a temperature sensor that monitors the temperature of the gas in the enclosure 200. The $CO_2$ concentration control device may also comprise a $CO_2$ concentration sensor that monitors the $CO_2$ concentration of the gas in the enclosure 200.

A door or the like is provided in the enclosure 200, the interior being completely sealed when the door is closed, allowing constant cleanliness, temperature and $CO_2$ concentration to be maintained for the air in the interior. The enclosure 200 is preferably transparent so as to allow observation of the state of the interior devices from the outside. In addition, the enclosure 200 may be a glove box integrated with gloves, such as rubber gloves.

The separating device 10 receives vials containing human blood, for example. The separating device 10 comprises an anticoagulant tank that stores anticoagulants such as ethylenediaminetetraacetic acid (EDTA), heparin and biologically standardized blood storage Solution A (ACD Solution A, product of Terumo Corp.), for example. The separating device 10 employs a pump or the like to add an anticoagulant to human blood from the anticoagulant tank.

In addition, the separating device 10 comprises a separating reagent tank that stores a mononuclear cell separating reagent such as Ficoll-Paque PREMIUM® (product of GE Healthcare, Japan). The separating device 10 employs a pump or the like to inject 5 mL of mononuclear cell separating reagent from the separating reagent tank into each of two 15 mL tubes, for example. Resin bags may be used instead of tubes.

The separating device 10 also comprises a buffering solution tank that stores a buffering solution such as phosphate-buffered saline (PBS). The separating device 10 employs a pump to add 5 mL of buffering solution from the buffering solution tank to 5 mL of human blood, for example, to dilute it. In addition, the separating device 10 employs a pump or the like to add 5 mL of the diluted human blood to each of the mononuclear cell separating reagents in the tubes.

The separating device 10 further comprises a temperature-adjustable centrifuge. The centrifuge is set to 18° C., for example. The separating device 10 employs a moving apparatus or the like to place the tubes in which the mononuclear cell separating reagent and human blood have been placed, into holders of the centrifuge. The centrifuge performs centrifugation of the solutions in the tubes for 30 minutes at 400×g, for example. Resin bags may be centrifuged instead of tubes.

After centrifugation, the separating device 10 collects the intermediate layers that have become turbid and white by the mononuclear cells in the solutions in the tubes, using a pump or the like. The separating device 10 employs a pump or the like to deliver the recovered mononuclear cell suspensions to the preintroduction cell solution-feeding channel 20. Alternatively, the separating device 10 also adds 12 mL of PBS, for example, to 2 mL of the recovered mononuclear cell solutions, and places the tubes in holders of the centrifuge. The centrifuge performs centrifugation of the solutions in the tubes for 10 minutes at 200×g, for example.

After centrifugation, the separating device 10 employs a pump or the like to remove the supernatants of the solutions in the tubes by suction, and adds 3 mL of mononuclear cell culture medium such as X-VIVO 10® (Lonza, Japan) to the mononuclear cell solutions in the tubes to prepare suspensions. The separating device 10 employs a pump or the like to deliver the mononuclear cell suspensions to the preintroduction cell solution-feeding channel 20. The separating device 10 may also employ a dialysis membrane to separate the mononuclear cells from the blood. When using somatic cells such as fibroblasts previously separated from skin or the like, the separating device 10 is not necessary.

The separating device 10 may also separate cells suitable for induction by a method other than centrifugal separation. For example, if the cells to be separated are T cells, cells that are CD3-, CD4- or CD8-positive may be separated by panning. If the cells to be separated are vascular endothelial precursor cells, then cells that are CD34-positive may be separated by panning. If the cells to be separated are B cells, cells that are CD10-, CD19- or CD20-positive may be separated by panning. The separation may also be carried out by a magnetic-activated cell sorting (MACS) method or flow cytometry, without limitation to panning. Moreover, the cells suitable for induction are not limited to cells derived from blood.

The inducing factor solution-feeding mechanism 21 comprises an inducing factor introducing reagent tank that stores an inducing factor introducing reagent solution. The inducing factor introducing reagent solution such as a gene introducing reagent solution includes, for example, an electroporation solution such as Human T Cell Nucleofector® (Lonza, Japan), a supplement solution, and a plasmid set. The plasmid set includes, for example, 0.83 µg of pCXLE-hOCT3/4-shp53-F, 0.83 µg of pCXLE-hSK, 0.83 µg of pCE-hUL and 0.5 µg of and pCXWB-EBNA1. The inducing factor solution-feeding mechanism 21 employs a micropump or the like to deliver the inducing factor introducing reagent solution to the preintroduction cell solution-feeding channel 20, in such a manner that the mononuclear cell suspension is suspended in the inducing factor introducing reagent solution.

The inner wall of the preintroduction cell solution-feeding channel 20 may be coated with poly-HEMA (poly 2-hydroxyethyl methacrylate) to render it non-cell-adherent, so that the cells do not adhere. Alternatively, a material resistant to cell adhesion may be used as the material for the preintroduction cell solution-feeding channel 20. Also, by using a material with good thermal diffusivity and $CO_2$ permeability as the material of the preintroduction cell solution-feeding channel 20, the conditions in the preintroduction cell solution-feeding channel 20 will be equivalent to the controlled temperature and $CO_2$ concentration in the enclosure 200. In addition, a back-flow valve may be provided in the preintroduction cell solution-feeding channel 20 from the viewpoint of preventing contamination.

The factor introducing device 30 connected to the preintroduction cell solution-feeding channel 20 is an electroporator, for example, and it receives a liquid mixture of the inducing factor introducing reagent solution and mononuclear cell suspension and carries out plasmid electroporation in the mononuclear cells. After carrying out electroporation, the factor introducing device 30 adds mononuclear cell culture medium to the solution containing the plasmid-electroporated mononuclear cells. The factor introducing device 30 employs a pump or the like to deliver the solution containing the plasmid-electroporated mononuclear cells (hereunder referred to as "inducing factor-introduced cells") to the introduced cell solution-feeding channel 31.

The factor introducing device 30 is not limited to an electroporator. The factor introducing device 30 may also introduce RNA coding for an initializing factor into the cells by a lipofection method. A lipofection method is a method in which a complex of nucleic acid as a negatively charged substance with positively charged lipids, is formed by electrical interaction, and the complex is incorporated into cells by endocytosis or membrane fusion. Lipofection is advantageous as it creates little damage to cells and has excellent introduction efficiency, while operation is convenient and less time is required. In addition, since there is no possibility of the initializing factor being inserted into the genome of the cells in lipofection, there is no need to confirm the presence or absence of insertion of exogenous genes by full genome sequencing of the obtained stem cells. Initializing factor RNA when used as a pluripotency inducing factor may include, for example, Oct3/4 mRNA, Sox2 mRNA, Klf4 mRNA, and c-Myc mRNA.

Lipofection of initializing factor RNA uses small interfering RNA (siRNA) or a lipofection reagent, for example. An siRNA lipofection reagent or mRNA lipofection reagent may be used as RNA lipofection reagents. More specifically, as RNA lipofection reagents there may be used Lipofectamine® RNAiMAX (Thermo Fisher Scientific), Lipofectamine® MessengerMAX (Thermo Fisher Scientific), Lipofectamin® 2000, Lipofectamin® 3000, NeonTransfection System (Thermo Fisher scientific), Stemfect RNA transfection reagent (Stemfect), NextFect® RNA Transfection Reagent (BioScientific), Amaxa® Human T cell Nucleofector® kit (Lonza, VAPA-1002), Amaxa® Human CD34 cell Nucleofector® kit (Lonza, VAPA-1003) or ReproRNA® transfection reagent (STEMCELL Technologies).

When the factor introducing device 30 is to introduce an initializing factor into cells by lipofection, the initializing factor RNA and reagents are introduced into the preintroduction cell solution-feeding channel 20 by the inducing factor solution-feeding mechanism 21.

Figure 2:
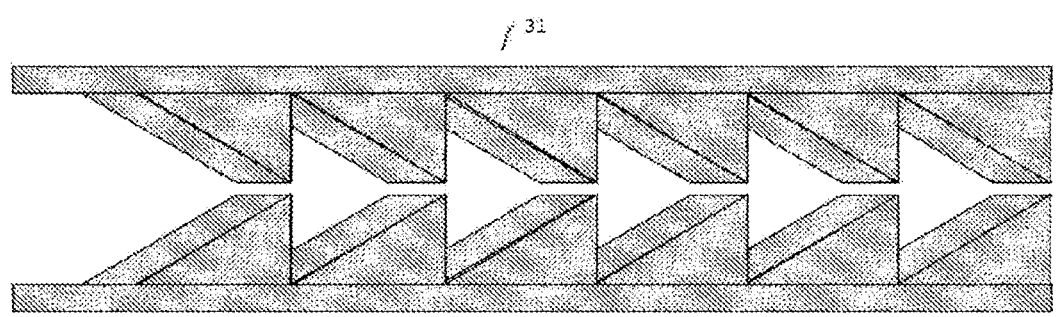
FIG. 2 is a schematic cross-sectional view of an example of an introduced cell solution-feeding channel in a stem cell production system according to an embodiment of the invention.
Figure 3:
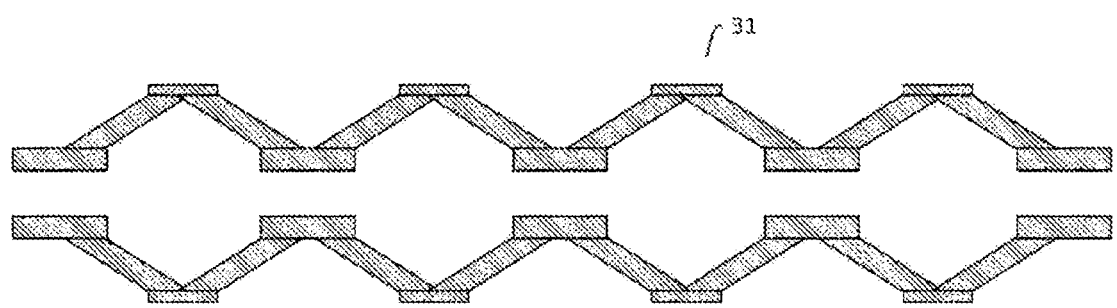
FIG. 3 is a schematic cross-sectional view of an example of an introduced cell solution-feeding channel in a stem cell production system according to an embodiment of the invention.

The inner wall of the introduced cell solution-feeding channel 31 may be coated with poly-HEMA to render it non-adhesive, so that the cells do not adhere. Alternatively, a material resistant to cell adhesion may be used as the material for the introduced cell solution-feeding channel 31. Also, by using a material with good thermal diffusivity and $CO_2$ permeability as the material of the introduced cell solution-feeding channel 31, the conditions in the introduced cell solution-feeding channel 31 will be equivalent to the controlled temperature and $CO_2$ concentration in the enclosure 200. In addition, a back-flow valve may be provided in the introduced cell solution-feeding channel 31 from the viewpoint of preventing contamination. Numerous cells die after electroporation, and cell masses of dead cells often result. Therefore, a filter may be provided in the introduced cell solution-feeding channel 31 to remove the dead cell masses. Alternatively, as shown in FIG. 2, one or a plurality of folds may be formed in the interior of the introduced cell solution-feeding channel 31 to intermittently vary the inner diameter. As another alternative, the inner diameter of the introduced cell solution-feeding channel 31 may be intermittently varied, as shown in FIG. 3.

As shown in FIG. 1, the cell mass preparation device 40 connected to the introduced cell solution-feeding channel 31 comprises an initializing culturing apparatus 50 that cultures the inducing factor-introduced cells prepared at the factor introducing device 30, a first dissociating mechanism 60 that dissociates the cell mass comprising stem cells (cell colonies) established at the initializing culturing apparatus 50 into a plurality of cell masses, an amplifying culturing apparatus 70 that carries out amplifying culturing of the plurality of cell masses that have been dissociated at the first dissociating mechanism 60, a second dissociating mechanism 80 that dissociates the cell mass comprising stem cells that have been amplifying cultured at the amplifying culturing apparatus 70 into a plurality of cell masses, and a cell mass transport mechanism 90 that successively delivers the plurality of cell masses to the packaging device 100.

The initializing culturing apparatus 50 can house a well plate in its interior. The initializing culturing apparatus 50 also comprises a pipetting machine. The initializing culturing apparatus 50 receives the solution containing the inducing factor-introduced cells from the introduced cell solution-feeding channel 31, and allocates the solution into the wells with the pipetting machine. The initializing culturing apparatus 50 adds stem cell culture medium such as StemFit® (Ajinomoto Co., Inc.) on the 3rd, 5th and 7th days, for example, after allocating the inducing factor-introduced cells to the wells. Basic fibroblast growth factor (basic FGF) may also be added to the culture medium as a supplement. Sustained-release beads, such as StemBeads FGF2 (Funakoshi Corp.), may also be added to the culture medium, for continuous supply of the FGF-2 (basic FGF, bFGF, FGF-b) to the culture medium. Also, since FGF is often unstable, a heparin-like polymer may be conjugated with the FGF to stabilize the FGF. Transforming growth factor beta (TGF-β), activin or the like may also be added to the culture medium. The initializing culturing apparatus 50 carries out culture medium exchange on the 9th day, for example, after allocating the inducing factor-introduced cells to the wells, and thereafter conducts culture medium exchange every 2 days until the iPS cell masses (colonies) exceed 1 mm. Medium exchange includes partial exchange of the culture medium, as well as replenishment.

When cell masses form, the initializing culturing apparatus 50 collects the cell masses with a pipetting machine, and adds a trypsin-substituting recombinant enzyme such as TrypLE Select® (Life Technologies Corp.) to the collected cell masses. In addition, the initializing culturing apparatus 50 places a vessel containing the collected cell masses in an incubator, and reacts the cell masses with the trypsin-substituting recombinant enzyme for 10 minutes at 37° C., 5% $CO_2$. When the cell masses are to be physically disrupted, there is no need for a trypsin-substituting recombinant enzyme. For example, the initializing culturing apparatus 50 disrupts the cell masses by pipetting with a pipetting machine. Alternatively, the initializing culturing apparatus 50 may disrupt the cell masses by passing the cell masses through a pipe provided with a filter, or a pipe that intermittently varies the inner diameter, similar to the introduced cell solution-feeding channel 31 shown in FIG. 2 or FIG. 3. Next, the initializing culturing apparatus 50 adds culture medium for pluripotent stem cells such as StemFit® (Ajinomoto Co., Inc.), to the solution containing the disrupted cell masses.

Culturing in the initializing culturing apparatus 50 may be carried out in a $CO_2$-permeable bag instead of a well plate. The culturing may be by adhesion culture or suspension culture. In the case of suspension culture, agitation culture may be carried out. The culture medium may also be in the form of agar. Agar culture media include gellan gum polymers. When an agar culture medium is used, there is no settling or adhesion of cells, and therefore agitation is not necessary even though it is suspension culture, and it is possible to form a single cell mass deriving from one cell, while the culturing in the initializing culturing apparatus 50 can also be by hanging drop culture.

The initializing culturing apparatus 50 may also comprise a first culture medium supply device that supplies culture medium including culture solution to a well plate or a $CO_2$-permeable bag. The first culture medium supply device collects the culture solution in the well plate or $CO_2$-permeable bag, and it may use a filter or dialysis membrane to filter the culture solution, to allow reuse of the purified culture solution. During this time, growth factors or the like may be added to the culture solution that is to be reused. Furthermore, the initializing culturing apparatus 50 may also comprise a temperature regulating device that regulates the temperature of the culture medium, and a humidity control device that controls the humidity in the vicinity of the culture medium.

Figure 4:
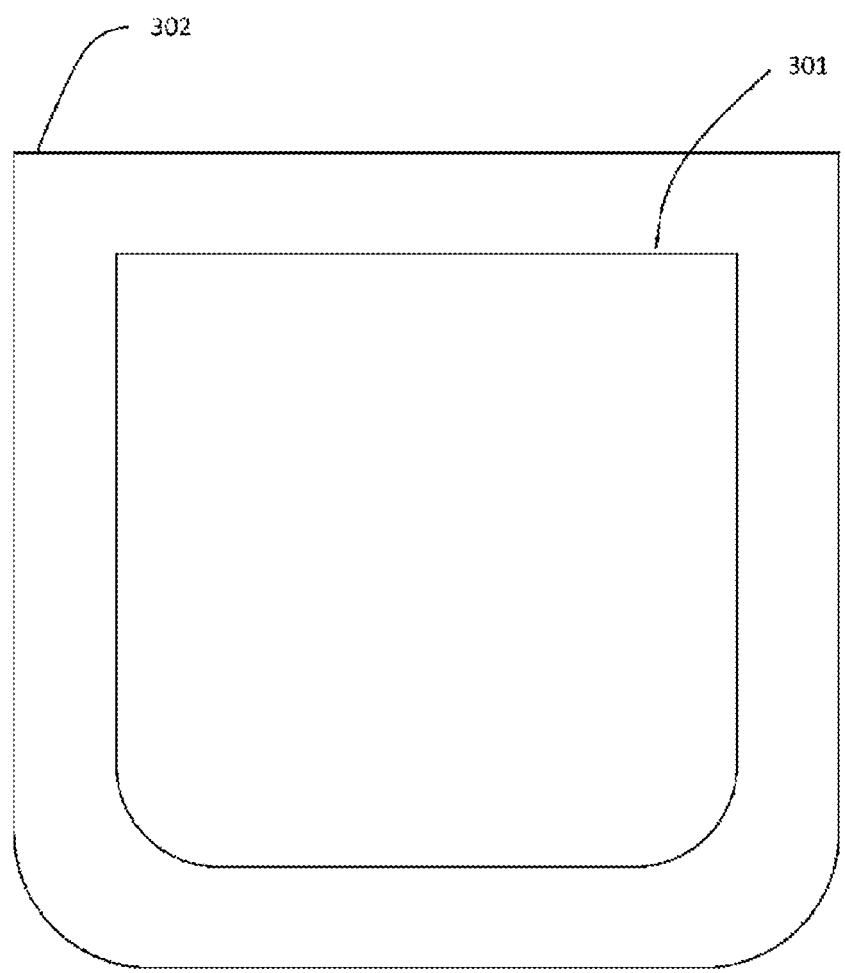
FIG. 4 is a schematic view of a culturing bag to be used in a stem cell production system according to an embodiment of the invention.

In the initializing culturing apparatus 50, the cells may be placed in a culture solution-permeable bag 301 such as a dialysis membrane as shown in FIG. 4, for example, and the culture solution-permeable bag 301 may be placed in a culture solution-impermeable $CO_2$-permeable bag 302, so that the culture solution is placed in bags 301, 302. The initializing culturing apparatus 50 may have multiple bags 302 prepared containing fresh culture solution, and the bag 302 in which the cell-containing bag 301 is placed may be replaced by a bag 302 containing fresh culture solution, at prescribed intervals of time.

Figure 5:
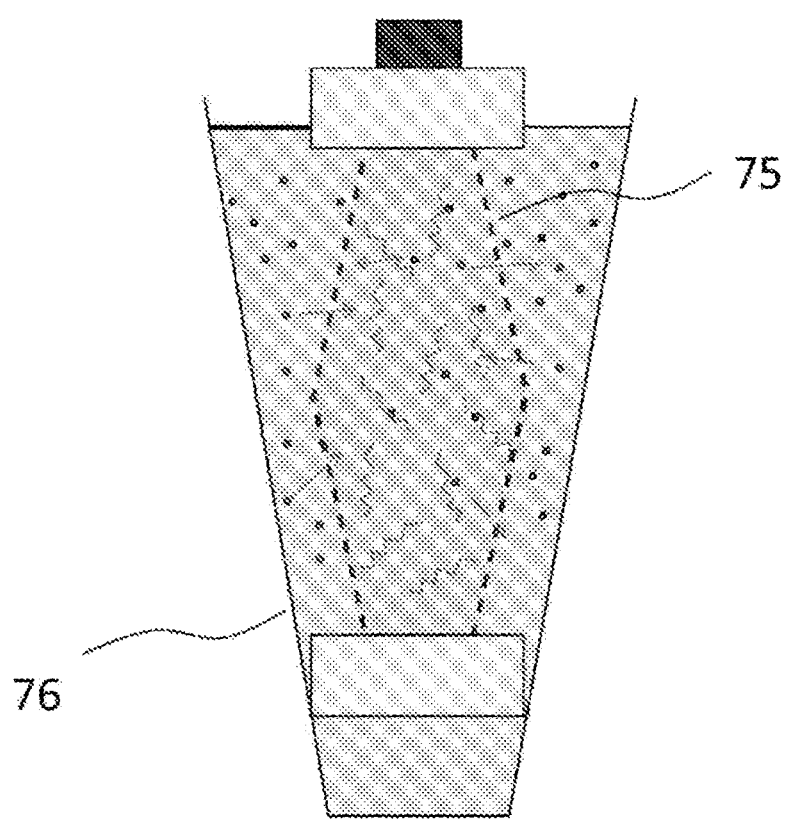
FIG. 5 is a schematic view of a suspension culture vessel according to an embodiment of the invention.

The method of culturing in the initializing culturing apparatus 50 is not limited to the method described above, and a suspension culture vessel such as shown in FIG. 5 may be used. The suspension culture vessel shown in FIG. 5 comprises a dialysis tube 75 in which the inducing factor-introduced cells and gel medium have been inserted, and a vessel 76 in which the dialysis tube 75 is placed and the gel medium is situated, around the periphery of the dialysis tube 75. Also, the suspension culture vessel may comprise a pH sensor that measures the hydrogen ion exponent (pH) of the gel medium surrounding the dialysis tube 75.

The dialysis tube 75 is made of a semipermeable membrane, and it allows permeation of ROCK inhibitor, for example. The molecular cutoff of the dialysis tube 75 is >0.1 KDa, >10 KDa, or >50 KDa. The dialysis tube 75 is made of, for example, cellulose ester, ethyl cellulose, a cellulose ester derivative, regenerated cellulose, polysulfone, polyacrylnitrile, polymethyl methacrylate, ethylenevinyl alcohol copolymer, polyester-based polymer alloy, polycarbonate, polyamide, cellulose acetate, cellulose diacetate, cellulose triacetate, copper ammonium rayon, saponified cellulose, a Hemophan membrane, a phosphatidylcholine membrane or a vitamin E coated membrane.

The vessel 76 used may be a conical tube such as a centrifugation tube. The vessel 76 is made of polypropylene, for example. The vessel 76 may also be $CO_2$-permeable. G-Rex® (Wilson Wolf) may be used as a $CO_2$-permeable vessel 76.

The inducing factor-introduced cells are to be placed in the dialysis tube 75. The gel medium is not agitated. Also, the gel medium does not include feeder cells. A solution-feeding channel may be connected to the dialysis tube 75 to deliver cell-containing culture medium into the dialysis tube 75. A solution-feeding channel may also be connected to the dialysis tube 75 to deliver the cell-containing culture medium in the dialysis tube 75 to the outside of the vessel.

The gel medium is prepared, for example, by adding deacylated gellan gum to the blood cell culture medium or stem cell culture medium, to a final concentration of 0.5 wt % to 0.001 wt %, 0.1 wt % to 0.005 wt % or 0.05 wt % to 0.01 wt %. For example, at the start of initializing culturing, gel medium prepared from the blood cell culture medium is used, and then gel medium prepared from stem cell culture medium is used.

The stem cell culture medium used may be human ES/iPS culture medium such as Primate ES Cell Medium (ReproCELL), for example.

The stem cell culture medium is not limited to this, however, and various stem cell culture media may be used. For example, Primate ES Cell Medium, Reprostem, ReproFF, ReproFF2, ReproXF (Reprocell), mTeSR1, TeSR2, TeSRE8, ReproTeSR (STEMCELL Technologies), PluriSTEM® Human ES/iPS Medium (Merck), NutriStem® XF/FF Culture Medium for Human iPS and ES Cells, Pluriton reprogramming medium (Stemgent), PluriSTEM®, Stemfit AKO2N, Stemfit AK03 (Ajinomoto), ESC-Sure® serum and feeder free medium for hESC/iPS (Applied StemCell) or L7® hPSC Culture System (LONZA) may be used.

The gel medium may include one or more high molecular compounds selected from the group consisting of gellan gum, hyaluronic acid, rhamsan gum, diutan gum, xanthan gum, carrageenan, fucoidan, pectin, pectic acid, pectinic acid, heparan sulfate, heparin, heparitin sulfate, keratosulfate, chondroitin sulfate, dermatan sulfate, rhamnan sulfate, and salts of the foregoing. The gel medium may also include methyl cellulose. Including methyl cellulose allows greater control of aggregation between the cells.

Alternatively, the gel medium may include at least one temperature sensitive gel selected from among poly(glycerol monomethacrylate) (PGMA), poly(2-hydroxypropyl methacrylate) (PHPMA), poly (N-isopropylacrylamide) (PNIPAM), amine terminated, carboxylic acid terminated, maleimide terminated, N-hydroxysuccinimide (NHS) ester terminated, triethoxysilane terminated, poly (N-isopropylacrylamide-co-acrylamide), poly (N-isopropylacrylamide-co-acrylic acid), poly (N-isopropylacrylamide-co-butylacrylate), poly (N-isopropylacrylamide-co-methacrylic acid), poly (N-isopropylacrylamide-co-methacrylic acid-co-octadecyl acrylate) and N-isopropylacrylamide.

The gel medium placed in the dialysis tube 75 does not need to include a ROCK inhibitor. The ROCK inhibitor may be added to the gel medium placed around the dialysis tube 75 in the vessel 76, to a final concentration of 1000 µmol/L to 0.1 µmol/L, 100 µmol/L to 1 µmol/L, or 5 µmol/L to 20 µmol/L, for example. By adding a ROCK inhibitor to the gel medium surrounding the dialysis tube 75, the ROCK inhibitor will penetrate into the dialysis tube 75 and colony formation by the cells will be promoted.

The gel medium may either include or not include growth factors such as basic fibroblast growth factor (bFGF) or TGF-β.

During suspension culturing of the cells in the dialysis tube 75, the gel medium surrounding the dialysis tube 75 in the vessel 76 is exchanged. Medium exchange includes partial exchange of the culture medium, as well as replenishment. In this case, the gel medium in the dialysis tube 75 does not need to be supplied. The gel medium may instead be supplied into the dialysis tube 75 during suspension culturing of the cells in the dialysis tube 75. In this case, the gel medium surrounding the dialysis tube 75 in the vessel 76 does not need to be supplied.

Figure 6:
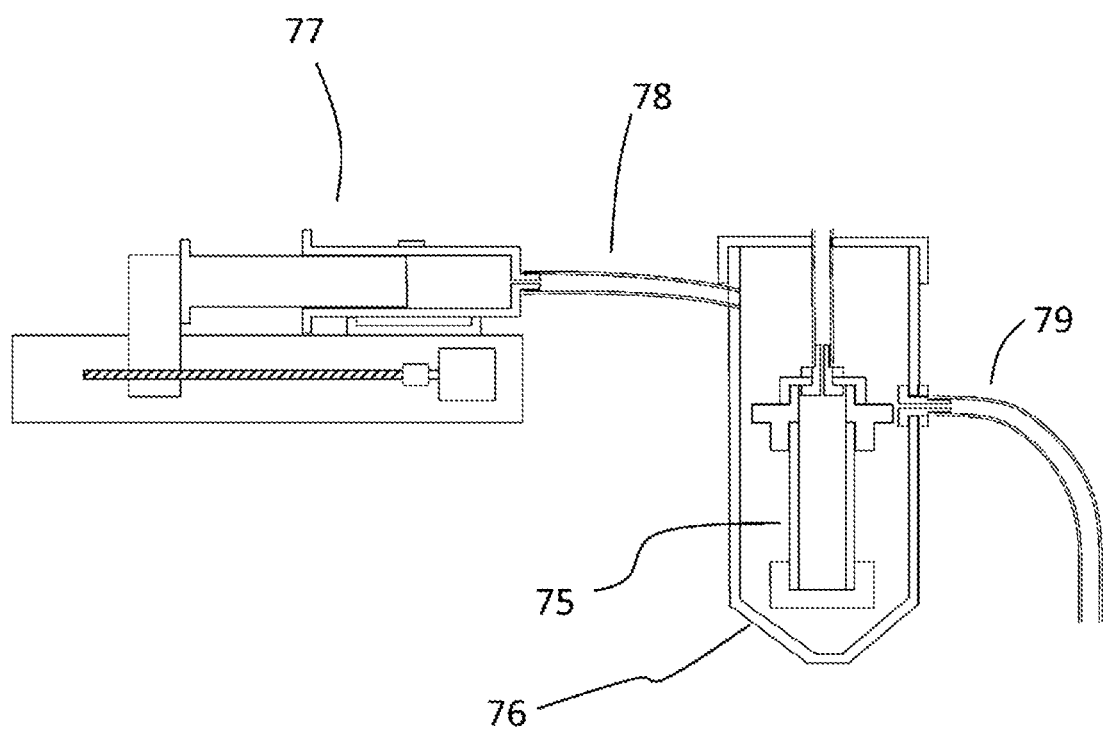
FIG. 6 is a schematic view of a supply culture medium solution-feeding pump and suspension culture vessel according to an embodiment of the invention.

As shown in FIG. 6, the stem cell production system of this embodiment uses a supply culture medium solution-feeding pump 77 as a culture medium supply device to exchange or supply gel medium surrounding the dialysis tube 75 in the vessel 76. The supply culture medium solution-feeding pump 77 used may be a pump used for drip infusion. The supply culture medium solution-feeding pump 77 and the suspension culture vessel 76 are connected by a solution-feeding tube 78. The supply culture medium solution-feeding pump 77 delivers gel medium into the suspension culture vessel 76 through the solution-feeding tube 78. A waste liquid tube 79 is connected to the suspension culture vessel 76. The gel medium in the suspension culture vessel 76 is discharged through the waste liquid tube 79. The gel medium in the suspension culture vessel 76 may be discharged, for example, by the pressure of fresh gel medium supplied by the supply culture medium solution-feeding pump 77, or it may be discharged utilizing gravity, or it may be discharged by a discharge pump.

The temperature of the gel medium to be delivered from the supply culture medium solution-feeding pump 77 to the culturing vessel is set, for example, so that the temperature of the gel medium in the culturing vessel does not vary drastically. For example, when the temperature of the gel medium in the culturing vessel is 37° C., the temperature of the gel medium delivered to the culturing vessel is set to 37° C. However, the culture medium before it is delivered to the culturing vessel may be set in cold storage at a low temperature of 4° C., for example, at the cold storage section.

The supply culture medium solution-feeding pump 77 is controlled so that, for example, the amount of the gel medium delivered into the suspension culture vessel 76 by the supply culture medium solution-feeding pump 77 and the amount of the gel medium discharged from the suspension culture vessel 76 are equal. The supply culture medium solution-feeding pump 77 may deliver the gel medium into the suspension culture vessel 76 constantly, or it may deliver the gel medium at appropriate intervals.

When the gel medium is delivered constantly, the flow rate of the gel medium being delivered may be constant or variable. For example, as explained below, the culture medium and the cell masses in the culture medium may be monitored with a photographing device, and the flow rate of the gel medium being delivered may be increased or decreased depending on the state of the culture medium and the cell mass in the culture medium.

Also, instead of constant delivery of the gel medium, delivery of the gel medium may be started and stopped depending on the state of the culture medium and the cell masses in the culture medium. In this case as well, the flow rate of the gel medium being delivered may be increased or decreased depending on the state of the culture medium and the cell masses in the culture medium.

If the flow rate of the gel medium being delivered to the culturing vessel is too high, the cells in the culturing vessel may undergo damage by the pressure of the gel medium. Therefore, the flow rate of the gel medium being delivered to the culturing vessel is set so that the cells do not suffer damage.

When culturing of the cells is to be continued without exchange of the culture medium, accumulation of waste products such as lactic acid discharged by the cells, or variation in pH, can adversely affect the cell culture. In addition, proteins including bFGF or recombinant proteins present in the culture medium may be degraded, resulting in loss of the components necessary for cell culturing.

To counter this, fresh culture medium may be delivered to the culturing vessel by the supply culture medium solution-feeding pump 77, and the old culture medium discharged from the culturing vessel, to remove waste products from the culturing vessel, to keep the pH in the culture medium in a suitable range, and to allow supply of the components necessary for culturing of the cells. This will allow the state of the culture medium to be kept nearly constant.

Figure 7:
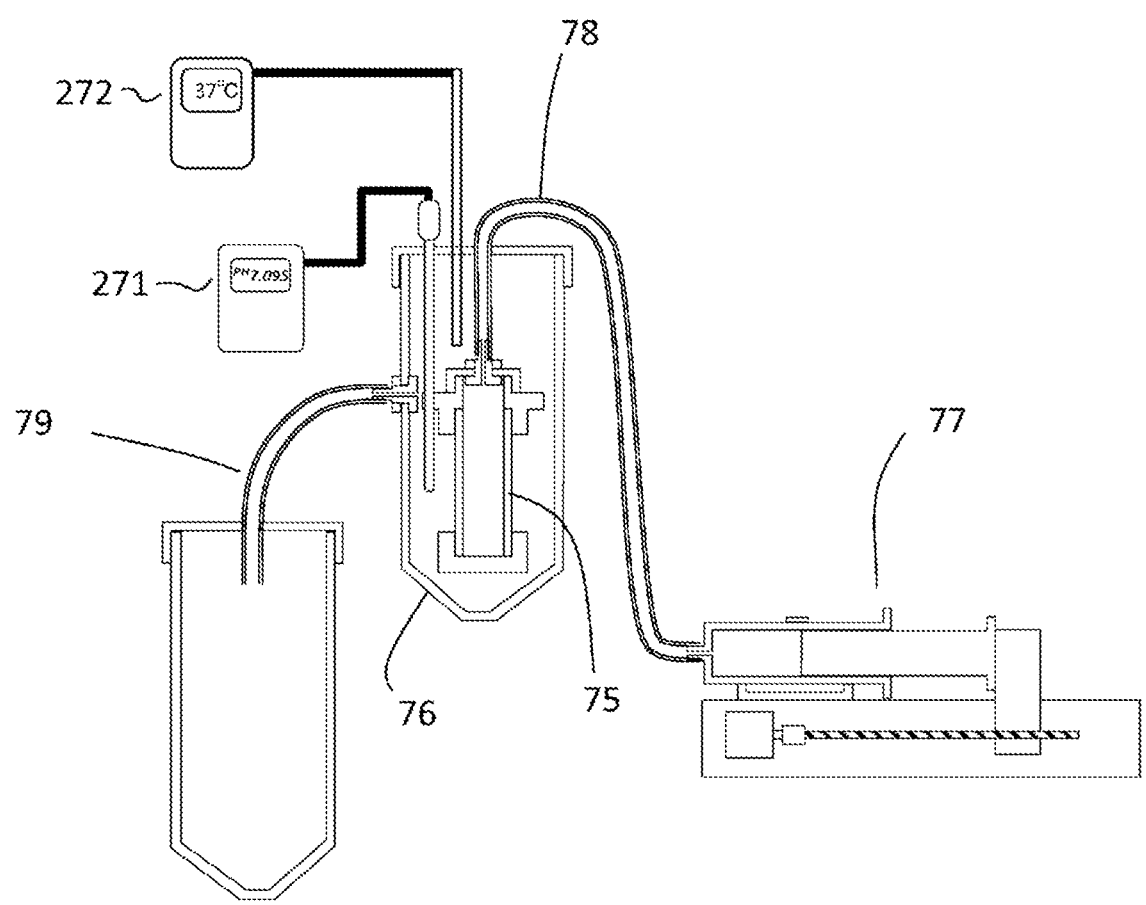
FIG. 7 is a schematic view of a supply culture medium solution-feeding pump and suspension culture vessel according to an embodiment of the invention.

FIG. 6 shows an example in which the supply culture medium solution-feeding pump 77 and the suspension culture vessel 76 are connected by the solution-feeding tube 78. In contrast, as shown in FIG. 7, the supply culture medium solution-feeding pump 77 and the interior of the dialysis tube 75 in the suspension culture vessel 76 may be connected by the solution-feeding tube 78. By delivering fresh gel medium into the dialysis tube 75, waste products present in the culture medium in the dialysis tube 75 are discharged out of the dialysis tube 75. In addition, the pH of the culture medium in the dialysis tube 75 can be kept in a suitable range, and the components necessary for culturing of the cells can be supplied to the culture medium in the dialysis tube 75.

The stem cell production system shown in FIG. 1 may further comprise an initializing culturing photographing device such as a photographing camera or video camera that photographically records culturing in the initializing culturing apparatus 50. If a colorless culture medium is used for the culture medium in the initializing culturing apparatus 50, it will be possible to minimize diffuse reflection and autologous fluorescence that may be produced when using a colored culture medium. In order to confirm the pH of the culture medium, however, a pH indicator such as phenol red may be included. Moreover, since induced cells and non-induced cells have differences in cellular shape and size, the stem cell production system may further comprise an induced state monitoring device that calculates the proportion of induced cells by photographing the cells in the initializing culturing apparatus 50. Alternatively, the induced state monitoring device may determine the proportion of induced cells by antibody immunostaining or RNA extraction. In addition, the stem cell production system may comprise a non-induced cell removing device that removes cells that have not been induced, by magnetic-activated cell sorting, flow cytometry or the like.

When the cells are being cultured on a flat dish such as a plate, the cell region spreads out in a planar manner. Thus, if the photographing device and the plate are oriented so that the optical axis of the lens of the photographing device is perpendicular to the dish surface, it will be possible to adjust the focus on essentially all of the cells on the plate.

When the cells are suspended in the culture medium for suspension culture, however, the cell region will spread out three-dimensionally, and therefore the distance in the optical axis direction from the photographing device to each of the cells will vary. It may therefore be difficult to adjust the focus to all of the cells without using a lens.

However, by using a bright lens (a lens with a low F value) or by imaging with as small an aperture as possible for the lens while illuminating the measuring target with a bright lighting, it is possible to increase the depth of the field.

Alternatively, a plurality of images may be taken while gradually varying the focal point of the lens, and the plurality of images synthesized to obtain a pseudo-deep focused image. Each of the plurality of images will be a blend of the focused cells and the blurry non-focused cells. The partial focused images may then be compiled from the plurality of images to produce a single synthetic image.

Figure 8:
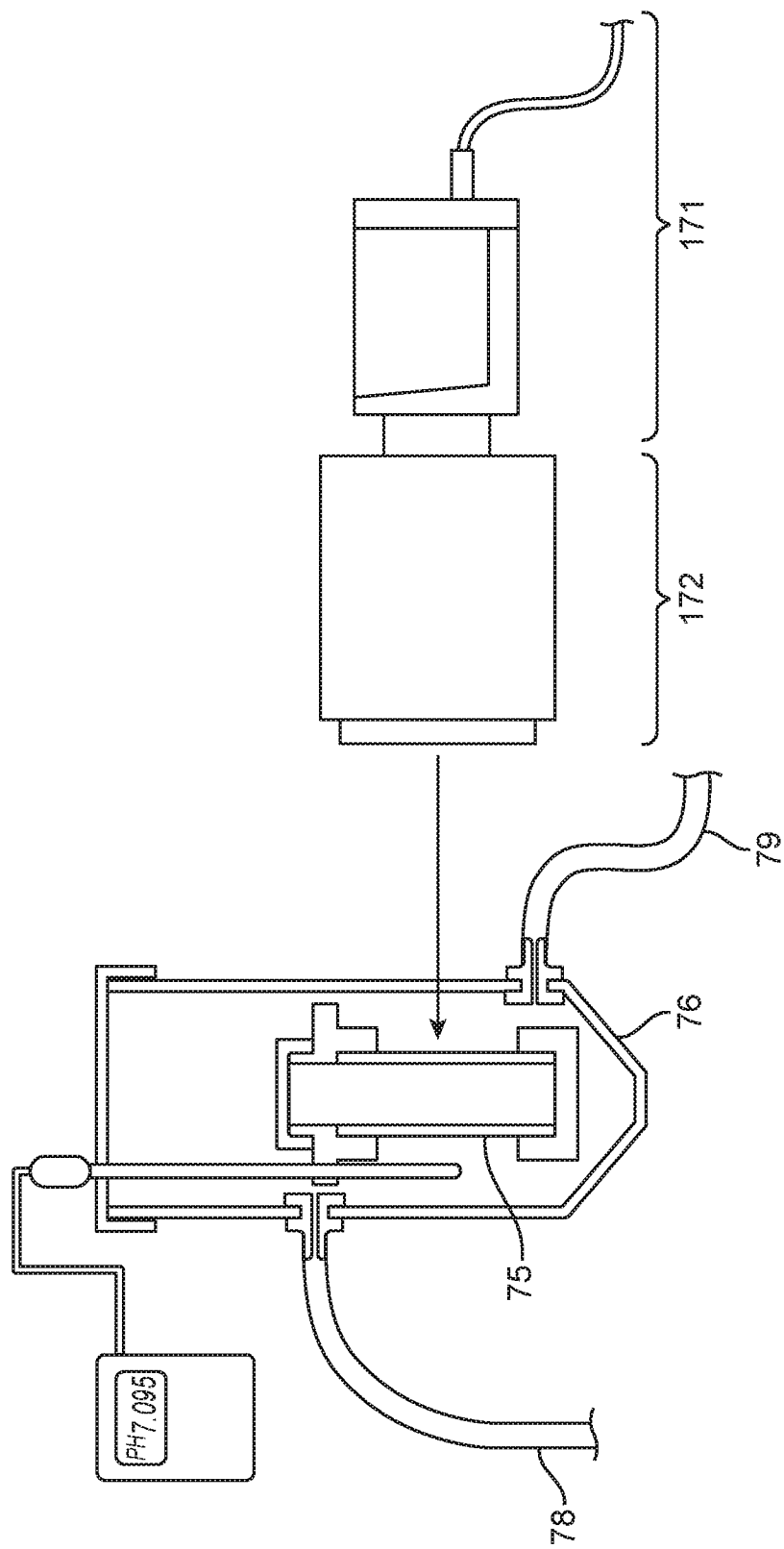
FIG. 8 is a schematic view of a suspension culture vessel and photographing device according to an embodiment of the invention.

Alternatively, as shown in FIG. 8, a telecentric lens 172 may be disposed between the initializing culturing photographing device 171 and the object, such as cells, in the suspension culture vessel. With the telecentric lens 172, the principal ray running from the object, such as cells, through the center of the lens aperture is parallel to the lens optical axis, and therefore the sizes of the photographed cells do not vary with distance even if the distances from the initializing culturing photographing device 171 to each of the plurality of cells in the suspension culture vessel are not uniform.

Figure 9:
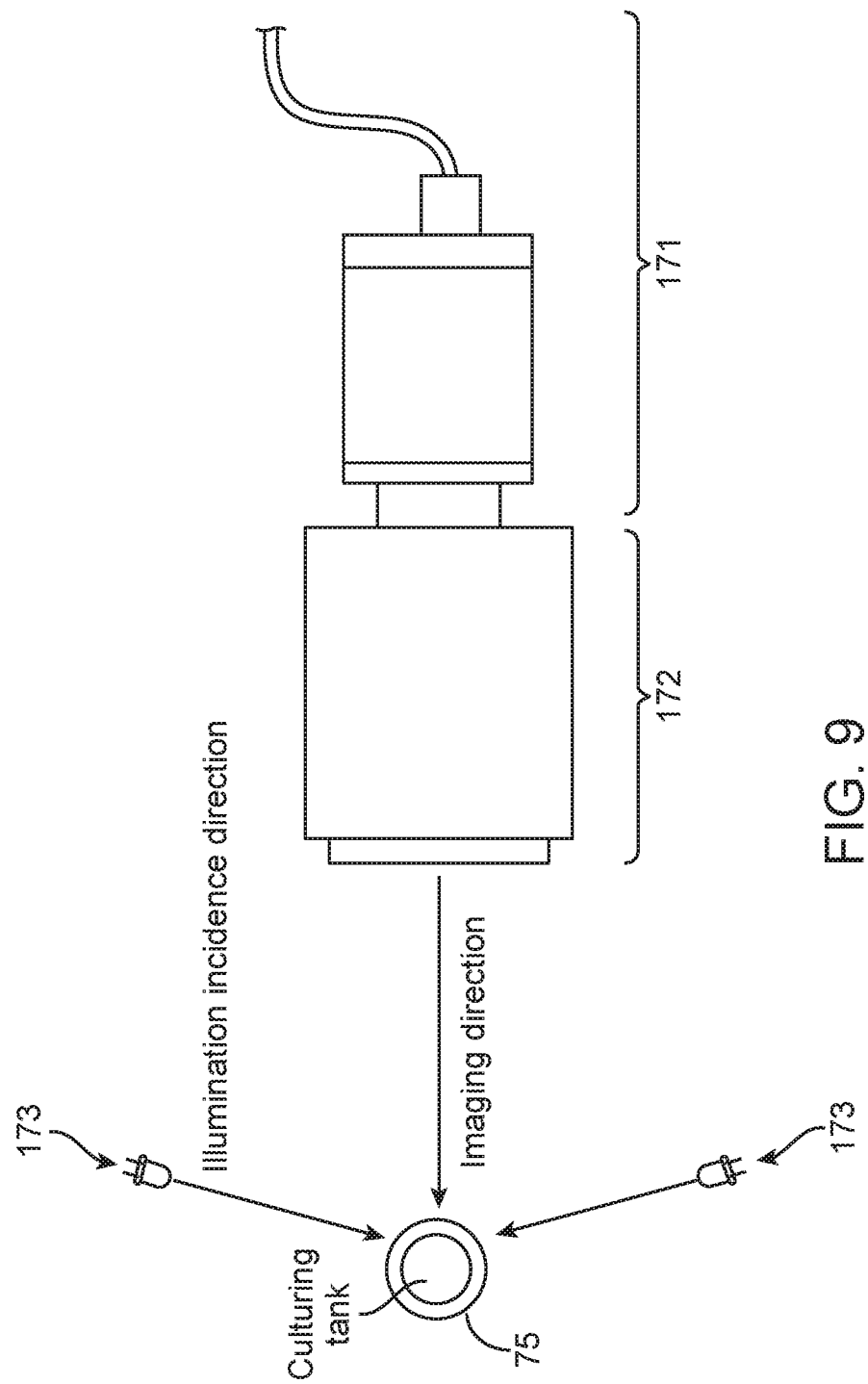
FIG. 9 is a schematic view of a suspension culture vessel and photographing device according to an embodiment of the invention.
Figure 10:
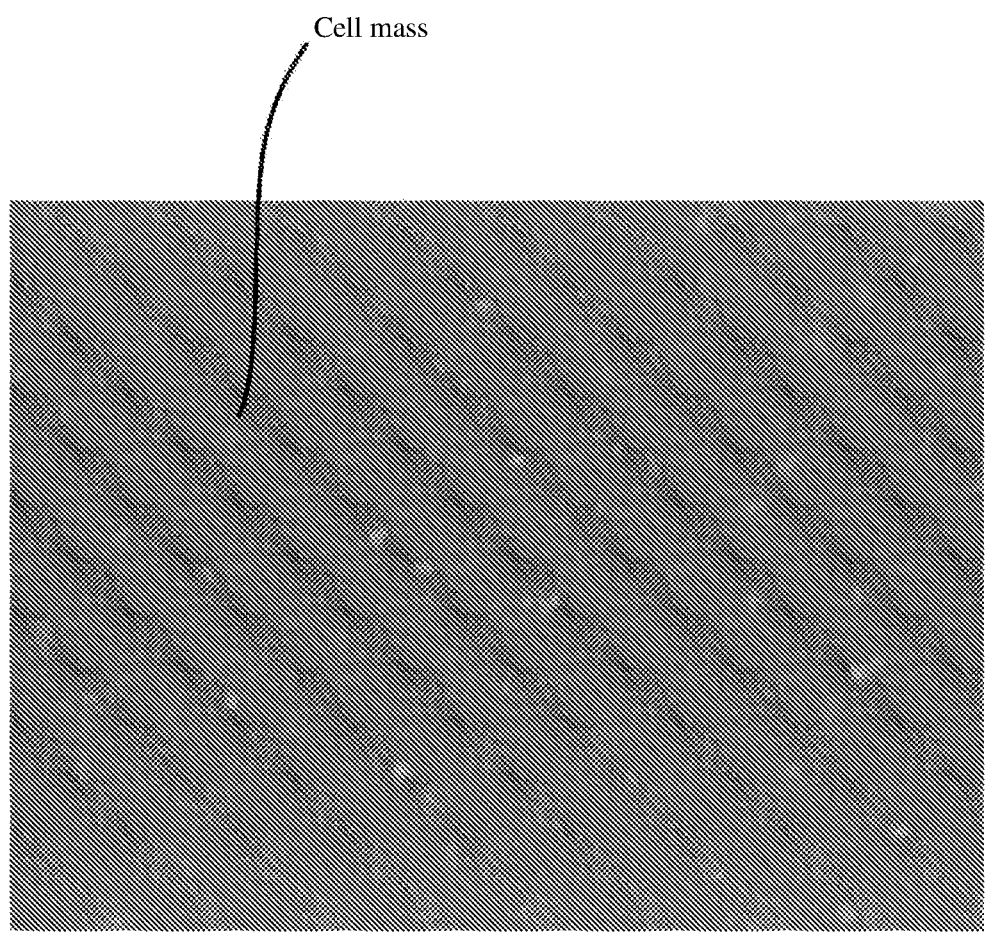
FIG. 10 is an example of an image of cells according to an embodiment of the invention.

FIG. 9 is a schematic view of the suspension culture vessel shown in FIG. 8, as seen from above. In FIG. 9, the vessel 76 shown in FIG. 8 is omitted. When cells are to be imaged with the initializing culturing photographing device 171, a scattered light illumination method may be employed, in which a cell observation illumination light source 173 is situated in the direction perpendicular to the optical axis of the initializing culturing photographing device 171, or a direction nearer the photographing device than the perpendicular direction, and illumination light is irradiated on the cells from the cell observation illumination light source 173. Scattered light from the illumination light on the cells will thus reach the initializing culturing photographing device 171, but the illumination light that has not impacted the cells passes through the culture medium and does not reach the initializing culturing photographing device 171. Thus, the culture medium parts of the image are relatively dark while the cell parts are relatively light. However, the illumination method is not limited to this method so long as the cells can be recognized in the image. FIG. 10 shows an example of an image of cells taken by a scattered light illumination method. The culture medium parts are relatively dark while the cell parts are relatively light.

Figure 11:
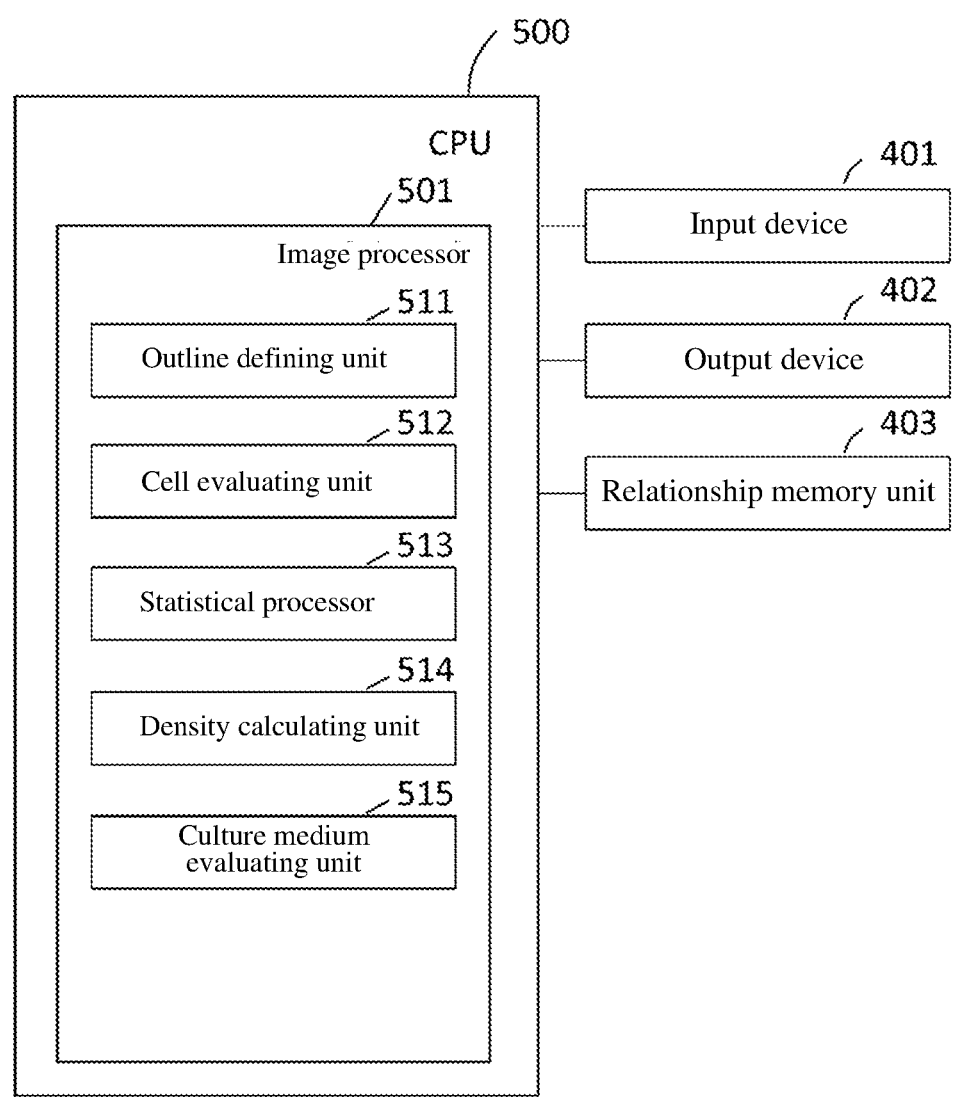
FIG. 11 is a schematic view of a central processing unit according to an embodiment of the invention.

As shown in FIG. 11, the stem cell production system of this embodiment may also comprise a central processing unit (CPU) 500 provided with an image processor 501 that carries out image processing of the image taken by the initializing culturing photographing device 171. An input device 401 such as a keyboard or mouse and an output device 402 such as a monitor may be connected to the CPU 500. The CPU 500 receives the image from the initializing culturing photographing device 171 via a bus, image interface or the like.

Figure 12:
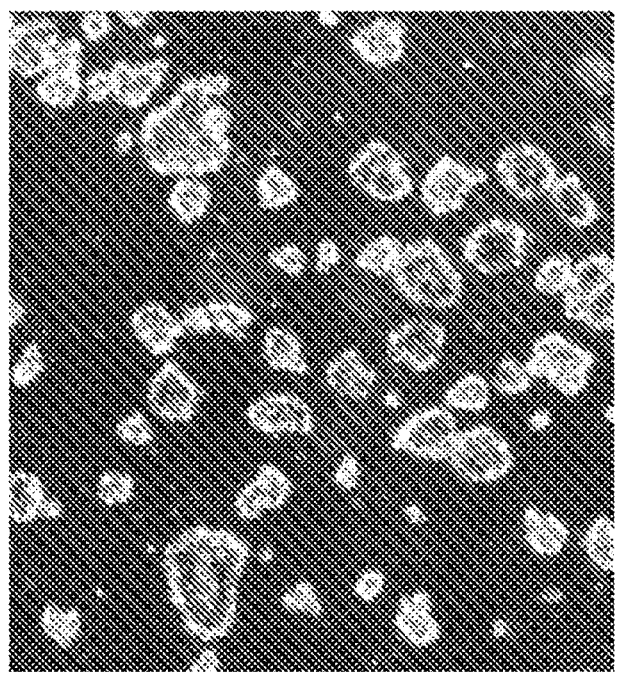
FIG. 12 is an example of an image of a cell mass according to an embodiment of the invention.

The image processor 501 may also comprise an outline defining unit 511 that defines the outlines of cells or cell masses in the cell image. FIG. 12 is an example of an enlarged image of iPS cell masses taken through a macro zoom lens. In the image shown in FIG. 12, the portions visible as white masses are the iPS cell masses, and the dark background portions are the culture medium.

Figure 13:
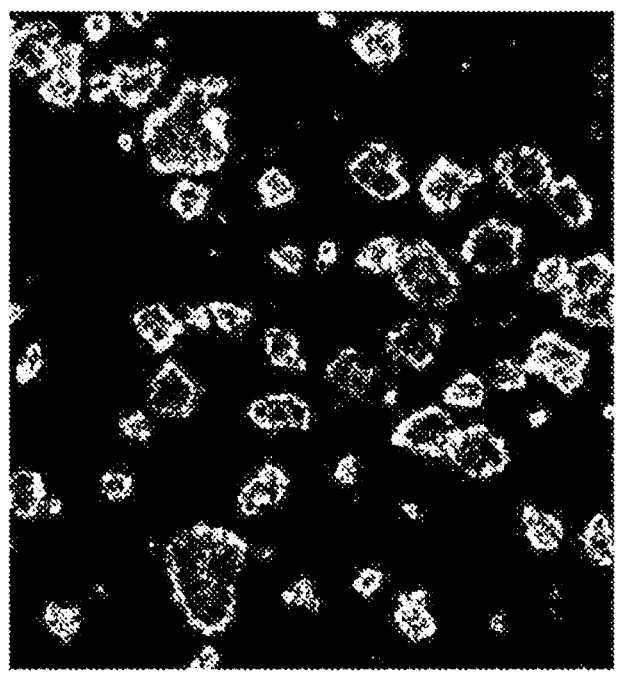
FIG. 13 is an example of a binarized image of a cell mass according to an embodiment of the invention.

When the image shown in FIG. 12 is an 8-bit grayscale image, and the image is subjected to binarization in which the maximum brightness value of 255, for example, is assigned to the values of the brightness of pixels having brightness values of at least a prescribed threshold value, and the minimum brightness value of 0, for example, is substituted for the values of the brightness of pixels having brightness values less than the prescribed threshold value, then not only the culture medium portions but also the interiors of the cell masses appear as the minimum brightness of black, as shown in FIG. 13, and contiguous portions appear between the interiors of the cell masses and the culture medium portions. Therefore, it may not be possible to extract the cells or cell masses with binarization.

Figure 14:
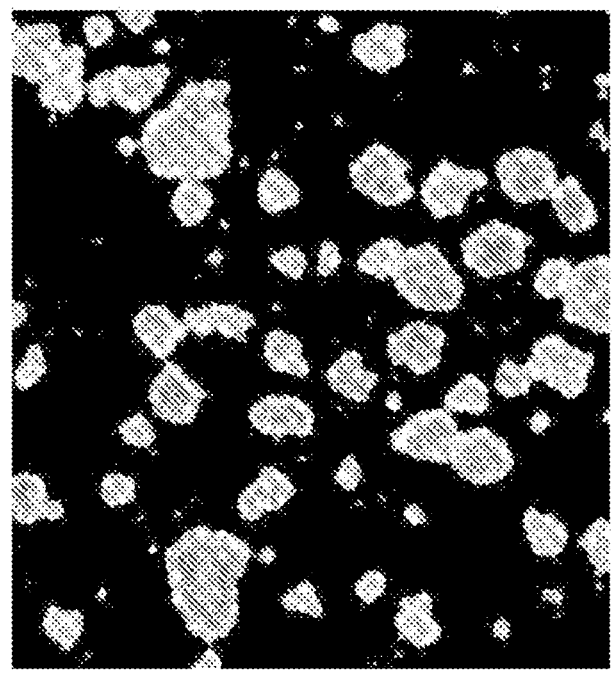
FIG. 14 is an example of an image of a cell mass to which a highpass filter has been applied, according to an embodiment of the invention.

However, the outline defining unit 511 of the stem cell production system according to the embodiment shown in FIG. 11 applies a highpass filter which allows passage of high-frequency components of at least a prescribed frequency in the spatial frequency while blocking low-frequency components of less than the prescribed frequency in the image of the cells, with a brightness value of 0, for example, as the minimum value. Numerous high-frequency components in the spatial frequency are present in the cell or cell mass portions of the cell image, while few high-frequency components in the spatial frequency are present in the culture medium portions. Consequently, in a cell image subjected to a highpass filter as shown in FIG. 14, the brightness values of the culture medium portions are the minimum value of 0, for example, while the cell or cell mass portions retain their brightness values. Therefore, the portions that are not at the minimum value of brightness may be considered to be the cells or cell masses.

In the image shown in FIG. 14, the portions where the brightness was not the minimum value are blobs, and even with detection by blob analysis, two mutually adjacent cell masses, for example, may appear to be a single cell mass in some cases.

Therefore, the outline defining unit 511 of the stem cell production system of the embodiment shown in FIG. 11 applies a watershed algorithm to the image that was subjected to the highpass filter. A watershed algorithm considers the brightness gradient in the image as mountainous corrugations, and divides the image so that zones formed by water flowing from the high locations of the mountains (the locations of high brightness) to the low locations (the locations of low brightness) are a single region.

Figure 15A:
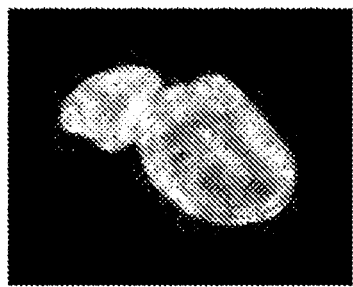
FIGS. 15A to 15C are examples of images of cell masses to which a watershed algorithm has been applied, according to an embodiment of the invention.
Figure 15B:
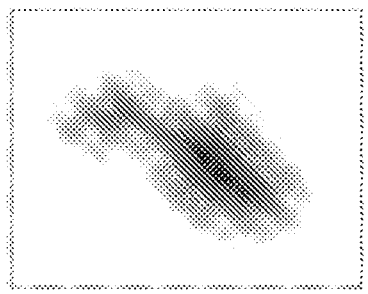

For example, the outline defining unit 511 of the stem cell production system of this embodiment converts the image by the Distance Transform method before applying the watershed algorithm to the image. The Distance Transform method is an image transforming method in which the value of the brightness of each pixel of an image is substituted based on the distance to the nearest background pixel. For example, in an image that has been subjected to a highpass filter, as shown in FIG. 15A, the brightness value in the culture medium region is converted to 255 as the maximum brightness value, to produce a white background as shown in FIG. 15B. Also, the value of the brightness of each pixel in the cell region is converted in a range of 0 up to less than 255, based on the distance to the nearest background pixel. For example, the brightness value is lowered the further it is from the nearest background pixel.

Figure 15C:
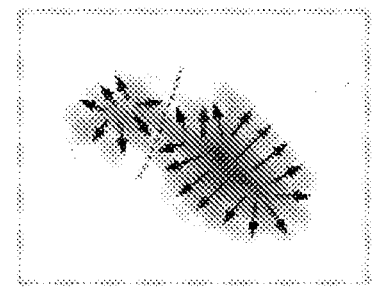

Next, the outline defining unit 511 of the stem cell production system of this embodiment applies a watershed algorithm to the image that has been transformed by the Distance Transform method. In the image shown in FIG. 15B, the dark portions with low brightness are considered to be the mountain ridges, it is imagined how water that has been poured on the image from the perpendicular direction will flow, as indicated by the arrows in FIG. 15C, the location where water that has flowed from different directions impacts is considered to be a valley, as indicated by the broken line in FIG. 15C, and the cell region is divided at the bottom of the valley.

Figure 16:
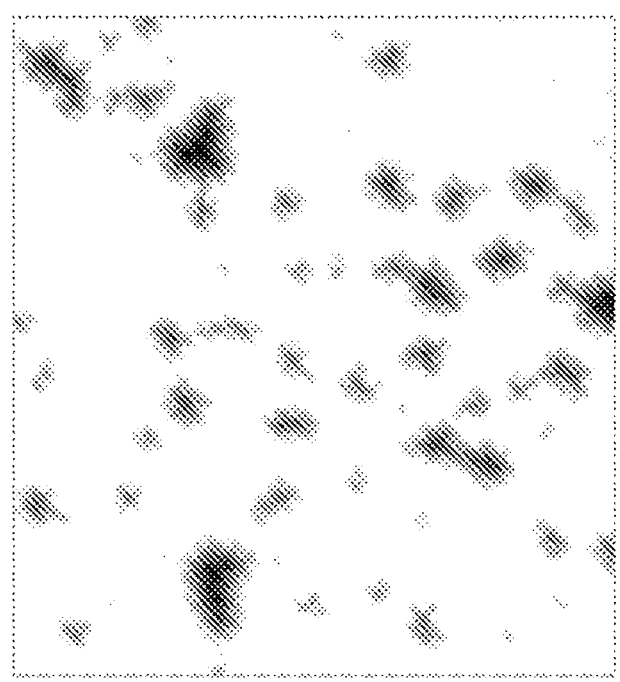
FIG. 16 is an example of an image of cell masses to which a Distance Transform method has been applied, according to an embodiment of the invention.
Figure 17:
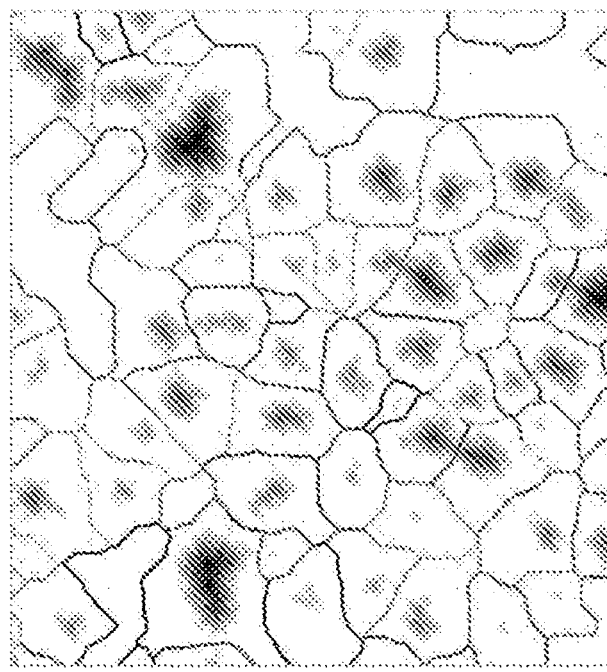
FIG. 17 is an example of an image of cell masses to which a watershed algorithm has been applied, according to an embodiment of the invention.
Figure 18:
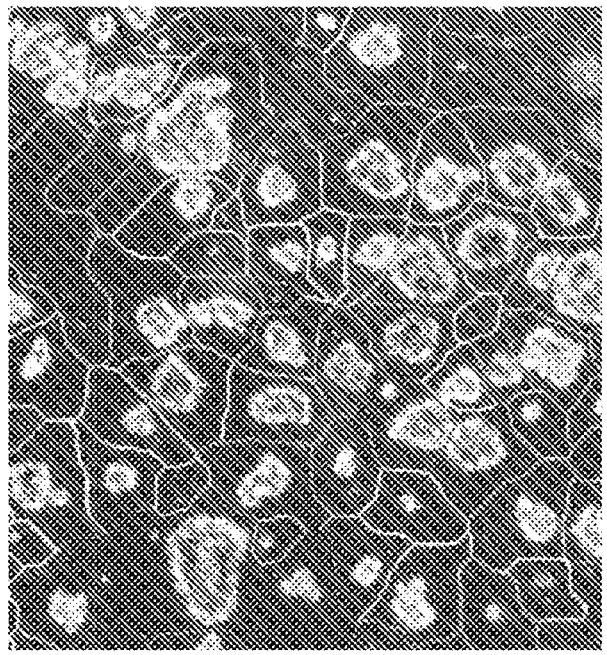
FIG. 18 is an example of an image of cell masses dissociated into multiple regions, according to an embodiment of the invention.
Figure 19:
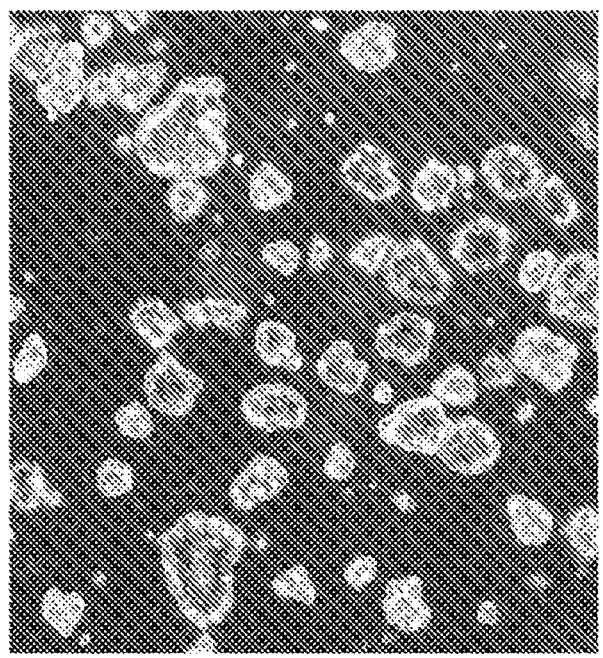
FIG. 19 is an example of an image of cell masses from which the outlines have been extracted, according to an embodiment of the invention.

When the pixels in the cell region of the image shown in FIG. 14 are transformed by the Distance Transform method, the image shown in FIG. 16 is obtained. When a watershed algorithm is applied to the image shown in FIG. 16, the image shown in FIG. 17 is obtained. When the obtained dividing lines are layered over the original image shown in FIG. 12, the image shown in FIG. 18 is obtained. In FIG. 18, the cell masses present in each region divided by the dividing lines are not masses in which a plurality of cell masses are adjacent, but rather may be considered to be single cell masses. In each region, therefore, the outlines of the cell masses can be extracted to allow accurate extraction of single cell masses, as shown in FIG. 19.

The image processor 501 of the stem cell production system of the embodiment shown in FIG. 11 may further comprise a cell evaluating unit 512. The cell evaluating unit 512 evaluates the cell mass size, etc. of each cell mass extracted by the outline defining unit 511. For example, the cell evaluating unit 512 calculates the area of a single cell mass extracted by the outline defining unit 511. When the shape of the single cell mass is considered circular, for example, the cell evaluating unit 512 also calculates the diameter of the single cell mass from the area, using the following formula (1).

$$D = 2(s/\pi)^{1/2} \quad (1)$$

Here, D represents the diameter and S represents the area.

If the cell mass grows too large, the nutrients and hormones in the culture medium may fail to reach the interior and the cells may differentiate. In addition, if cell masses that are too small are transferred to amplifying culture without using a ROCK inhibitor, cell death or karyotypic abnormalities may occur. Consequently, the cell evaluating unit 512 may emit an alert when the individual cell mass sizes are outside of the suitable range. In addition, the cell evaluating unit 512 may output a timing for transfer to amplifying culture when the individual cell mass sizes are beyond a prescribed threshold value. Furthermore, the supply rate of culture medium at the initializing culturing apparatus 50 may be varied according to the calculated cell mass sizes. For example, the supply rate of the culture medium may be increased as the cell mass sizes increase.

Figure 20:
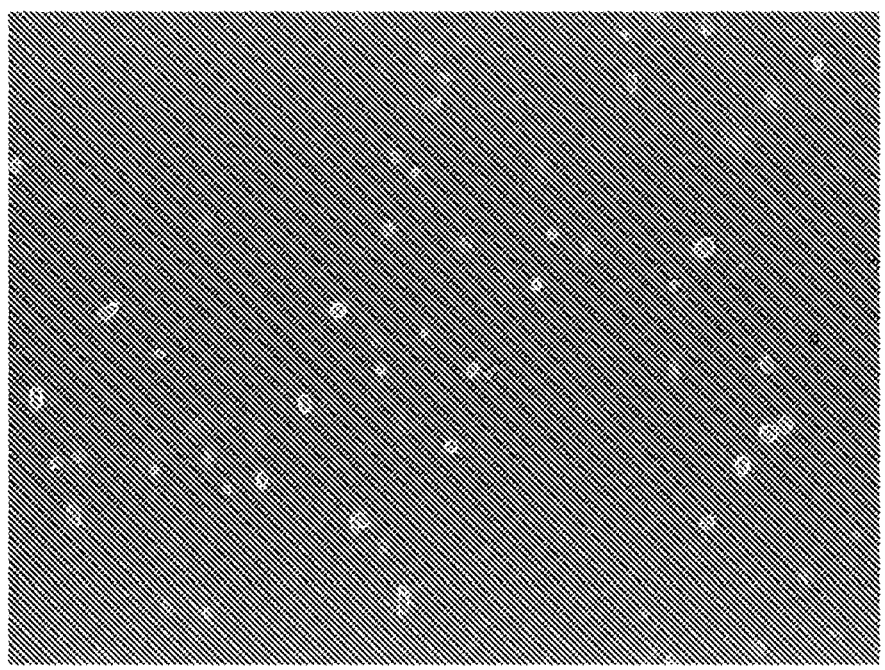
FIG. 20 is an example of an image of cell masses from which the outlines have been extracted, according to an embodiment of the invention.
Figure 21:
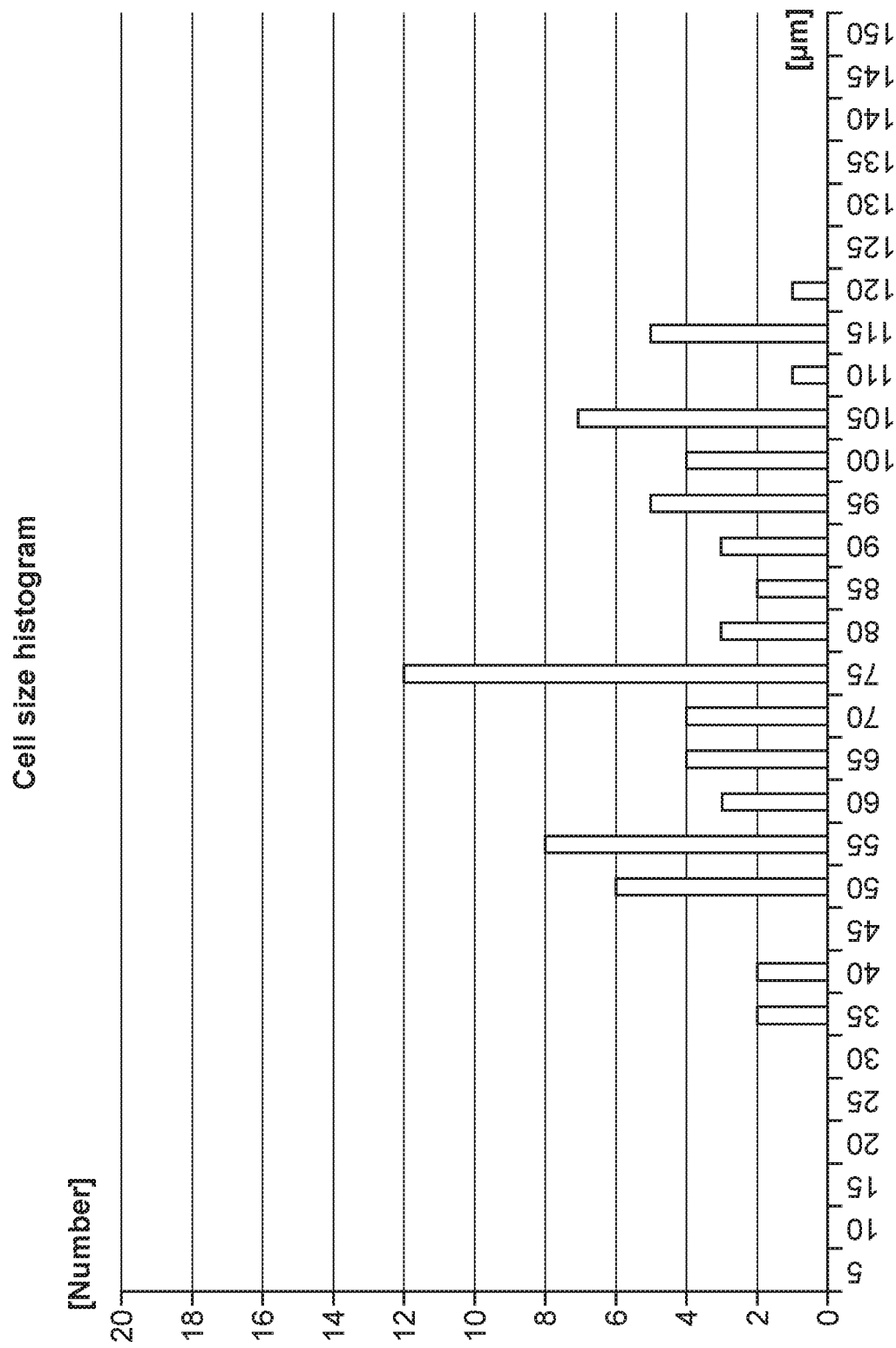
FIG. 21 is an example of a size histogram for cells according to an embodiment of the invention.

The image processor 501 of the stem cell production system of this embodiment may further comprise a statistical processor 513 that statistically processes data obtained from the image that has undergone image processing. FIG. 20 is an example of image processing of the image shown in FIG. 10, with the cell mass portions extracted and outlined. FIG. 21 is an example of a histogram of cell mass sizes, drawn based on the image shown in FIG. 20. By thus continuously and periodically obtaining cell data, it is possible to quantitatively ascertain the degree of growth, number and compactness of the cell masses, allowing the results of culturing to be stabilized. The supply rate of culture medium at the initializing culturing apparatus 50 may also be varied according to the calculated number of cell masses. For example, the supply rate of the culture medium may be increased as the number of cell masses increases.

The image processor 501 of the stem cell production system according to the embodiment shown in FIG. 11 may further comprise a density calculating unit 514 that calculates the turbidity of the culture medium from the image of the culture medium and calculates the cell mass density in the culture medium based on the turbidity of the culture medium.

For example, a relationship memory unit 403 comprising a volatile memory or a non-volatile memory may be connected to the CPU 500. The relationship memory unit 403 stores, for example, the relationship between the turbidity of the culture medium and the cell mass density in the culture medium, that have been previously obtained. The density calculating unit 514 reads out the relationship between turbidity and density from the relationship memory unit 403. The density calculating unit 514 also calculates the density of cell masses in the culture medium, based on the value of the turbidity of the culture medium that has been calculated from the image of the culture medium, and the relationship between turbidity and density. This allows the cell mass density to be measured in a non-destructive manner without harvesting the cell masses from the culture medium.

Moreover, the density calculating unit 514 may output a timing for transfer to the amplifying culturing, when the cell mass density has reached at least at prescribed threshold value. In addition, the density calculating unit 514 may calculate the cell mass density in the culture medium with time, and may calculate the growth rate of the cell masses. An abnormal growth rate may indicate abnormalities in the cells. For example, the density calculating unit 514 emits an alert when an abnormal growth rate has been calculated. Culturing of the cells may be interrupted when this occurs.

If the cell mass density in the culture medium is high and the distance between cell masses is too close, a plurality of cell masses may adhere together to form a single large cell mass. In a large cell mass, the nutrients and hormones in the culture medium may fail to reach the interior and the cells within it may differentiate. On the other hand, if the cell mass density in the culture medium is lower than the preferred range, the cell mass growth rate and cell mass formability may be significantly reduced.

However, since the cell mass density can be calculated by the density calculating unit 514, it is possible to easily determine whether or not the cell mass density is within the preferred range. When the cell mass density has become lower than the preferred range, a judgment may be made to interrupt the culturing, for example. Furthermore, the supply rate of culture medium at the initializing culturing apparatus 50 may be varied according to the calculated cell mass density. For example, the supply rate of the culture medium may be increased as the cell mass density increases.

Figure 22:
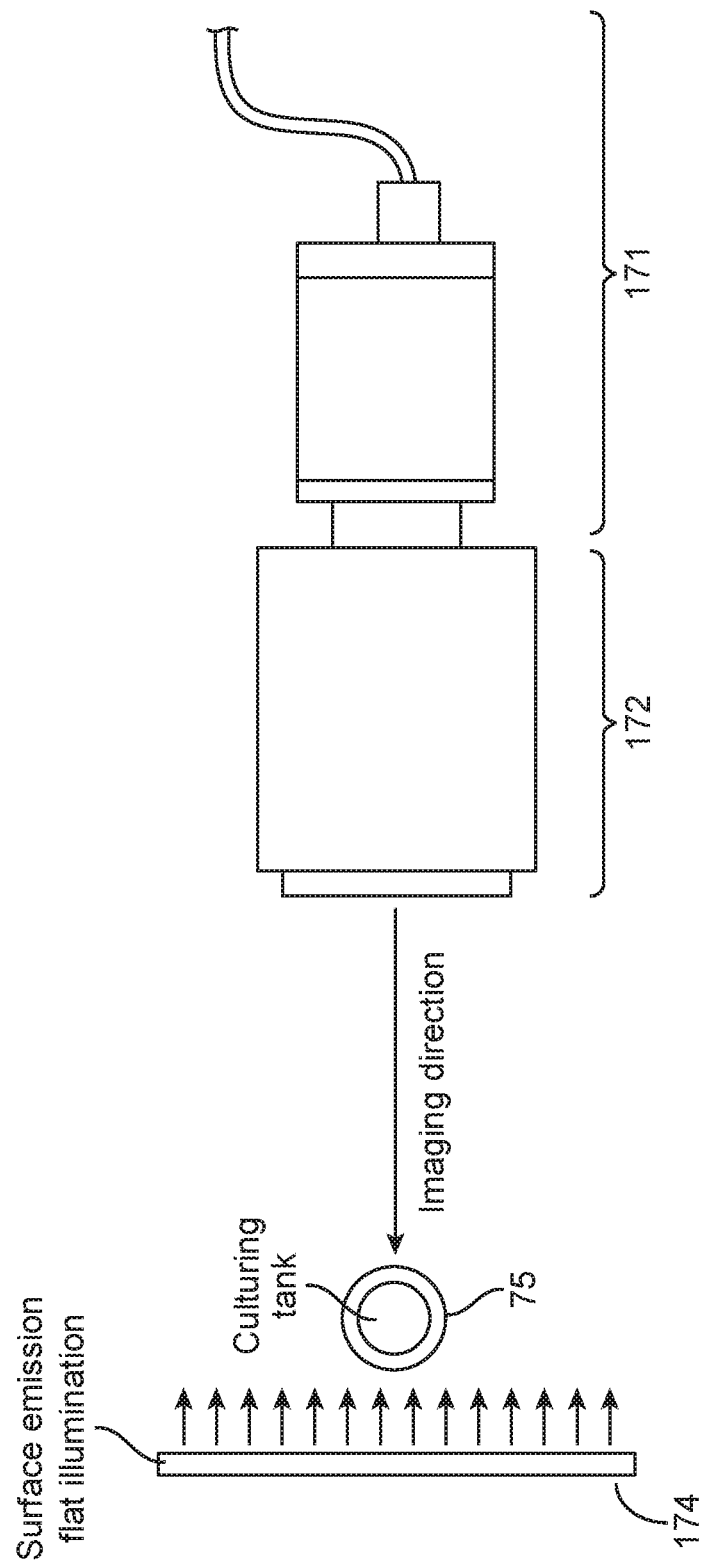
FIG. 22 is a schematic view of a suspension culture vessel and photographing device according to an embodiment of the invention.

In addition, in order to observe variation in the culture medium color that takes place with cell metabolism, a culture medium observation illumination light source 174 may be situated at a location facing the initializing culturing photographing device 171 and sandwiching the suspension culture vessel, as shown in FIG. 22. A surface light source, for example, may be used as the medium observation illumination light source 174, with the medium observation illumination light source 174 emitting white parallel rays, for example. The illumination light emitted from the medium observation illumination light source 174 passes through the culture medium and impinges on the initializing culturing photographing device 171, thereby allowing the culture medium color to be imaged by the initializing culturing photographing device 171.

Cell culturing is generally carried out with a constant culture medium pH near 6.8 to 7.2. When the culture medium pH is to be measured, a pH reagent such as phenol red is added to the culture medium. Phenol red changes due to the pH of the culture medium. When the carbon dioxide concentration of the gas contacting the culture medium is insufficient, carbon dioxide in the air does not equilibrate with carbon dioxide from bicarbonate in the culture medium, and therefore the culture medium becomes alkaline and the culture medium color turns reddish violet. Also, with accumulation of waste products consisting mainly of lactic acid discharged by the cells, the culture medium becomes acidic and the culture medium color turns yellow. Acidity of the culture medium indicates that the nutrients in the culture medium have been depleted.

The image processor 501 of the stem cell production system according to the embodiment shown in FIG. 11 may further comprise a culture medium evaluating unit 515 that evaluates the culture medium based on the image of the culture medium illuminated by the medium observation illumination light source. The culture medium evaluating unit 515 performs image processing of the culture medium image, for example, and expresses the color of the culture medium as the three parameters HSV: Hue, chroma (Saturation) and brightness (Value). Of these, hue is a parameter corresponding to a concept commonly referred to as "color shade" or "tint". Hue is commonly represented as angle units.

Figure 23:
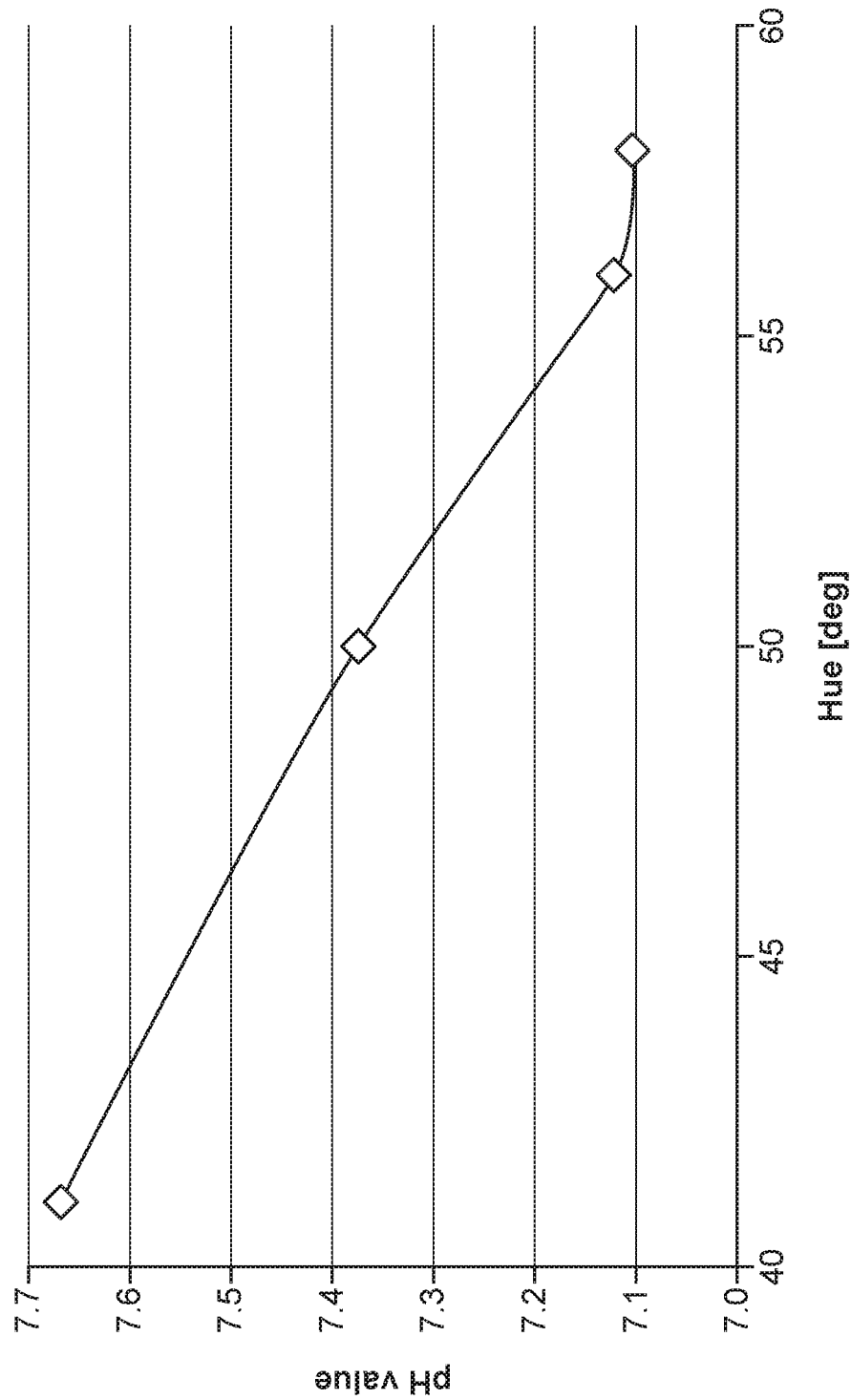
FIG. 23 is an example of a graph showing the relationship between culture medium pH and culture medium hue, according to an embodiment of the invention.

FIG. 23 is an example of a graph showing the relationship between change in culture medium hue and change in culture medium pH, with long-term culturing of cells without exchange of the medium. Immediately after the start of culturing, the culture medium pH was near 7.7, but the culture medium pH decreased to near 7.1 as time progressed. At the same time, the culture medium hue was near 40 immediately after the start of culturing, but increased to nearly 60 as time progressed. Thus, culture medium hue is correlated with culturing time and culture medium pH. Therefore, the culture medium evaluating unit 515 shown in FIG. 11 judges the state of the culture medium by monitoring the hue of the culture medium.

The relationship memory unit 403 stores, for example, the relationship between the hue of the culture medium and the pH of the culture medium, that have been previously obtained. The culture medium evaluating unit 515 reads out the relationship between hue and pH from the relationship memory unit 403. The culture medium evaluating unit 515 also calculates the pH value of the photographed culture medium based on the value of the hue of the culture medium that has been calculated from the culture medium image, and the relationship between hue and pH. For example, the culture medium evaluating unit 515 may obtain an image of the culture medium over time and calculate the value of the pH of the culture medium.

Incidentally, the culture medium pH may also be measured with a pH sensor 271, as shown in FIG. 7. The culture medium temperature may also be measured with a thermometer 272. In this case, the culture medium evaluating unit 515 may receive the value of the culture medium pH from the pH sensor 271, and may receive the value of the culture medium temperature from the thermometer 272.

When the culture medium hue or culture medium pH are outside of the prescribed ranges, the culture medium evaluating unit 515 judges that exchange of culture medium should be promoted, or that contamination has occurred in the culture medium. Medium exchange includes partial exchange of the culture medium, as well as replenishment.

Chemical analysis of the culture medium components is costly, and when the culture medium is taken out of the system for chemical analysis of the culture medium, there is a risk that the aseptic state of the culture medium may not be maintained. In contrast, monitoring the state of the culture medium by monitoring the culture medium hue has low cost and does not affect the aseptic state of the culture medium.

When the culture medium evaluating unit 515 has judged that the culture medium hue or culture medium pH is outside of the prescribed range, the culture medium surrounding the dialysis tube 75 of the suspension culture vessel is exchanged by the supply culture medium solution-feeding pump 77 shown in FIG. 6, for example. Alternatively, when the culture medium is being constantly exchanged, the exchange rate of the culture medium surrounding the dialysis tube 75 of the suspension culture vessel by the supply culture medium solution-feeding pump 77 increases, and the flow rate of the exchanged culture medium increases. This allows the culture medium pH to be maintained within a range suitable for cell culturing, and allows sufficient nutrients to be supplied to the culture medium.

In addition, the culture medium evaluating unit 515 may calculate the growth rate of the cells from the rate of change of the culture medium hue. The relationship memory unit 403 stores, for example, the relationship between the rate of change in the culture medium hue and the growth rate of the cells, that have been previously obtained. The culture medium evaluating unit 515 reads out the relationship between the hue change rate and the growth rate, from the relationship memory unit 403. In addition, the culture medium evaluating unit 515 calculates the value for the growth rate of the cells, based on the calculated value of the hue change rate and the relationship between the hue change rate and the growth rate.

When the culture medium evaluating unit 515 has judged that the temperature of the culture medium is outside of the prescribed range, it may control a temperature regulating device so as to change the temperature surrounding the culturing vessel, or the temperature of the supplied culture medium. For example, when the temperature of the culture medium is lower than the prescribed range, the culture medium evaluating unit 515 regulates the temperature regulating device so that the temperature of the culture medium rises. Also, when the temperature of the culture medium is higher than the prescribed range, the culture medium evaluating unit 515 regulates the temperature regulating device so that the temperature of the culture medium falls.

A first cell mass solution-feeding channel 51 is connected to the initializing culturing apparatus 50 shown in FIG. 1. The initializing culturing apparatus 50 employs a pump or the like to deliver a solution containing trypsin-substituting recombinant enzyme and the cell masses to the first cell mass solution-feeding channel 51. When the cell masses are to be physically disrupted, there is no need for a trypsin-substituting recombinant enzyme. Also, the first cell mass solution-feeding channel 51 may have an inner diameter that allows passage of only induced cells of less than a prescribed size, and it may be connected to a branched fluid channel that removes non-induced cells of a prescribed size or larger. As mentioned above, when a gel medium is used, the cell masses can be collected by suctioning up the gel medium.

The pump that delivers the cell mass-containing solution to the first cell mass solution-feeding channel 51 may be driven when, for example, the value of the cell mass size calculated by the cell evaluating unit 512 shown in FIG. 11 is at least a prescribed threshold value. Alternatively, the pump that delivers the cell mass-containing solution to the first cell mass solution-feeding channel 51 shown in FIG. 1 may be driven when, for example, the value of the cell mass density calculated by the density calculating unit 514 shown in FIG. 11 is at least a prescribed threshold value.

The inner wall of the first cell mass solution-feeding channel 51 shown in FIG. 1 may be coated with poly-HEMA to render it non-cell-adherent, so that the cells do not adhere. Alternatively, a material resistant to cell adhesion may be used as the material for the first cell mass solution-feeding channel 51. Also, by using a material with good thermal diffusivity and $CO_2$ permeability as the material of the first cell mass solution-feeding channel 51, the conditions in the first cell mass solution-feeding channel 51 will be equivalent to the controlled temperature and $CO_2$ concentration in the enclosure 200. In addition, a back-flow valve may be provided in the first cell mass solution-feeding channel 51 from the viewpoint of preventing contamination.

The first cell mass solution-feeding channel 51 is connected to the first dissociating mechanism 60. The first dissociating mechanism 60 comprises a mesh, for example. The cell masses in the solution are dissociated into a plurality of cell masses of the sizes of the holes of the mesh, when they pass through the mesh by water pressure. For example, if the mesh hole sizes are uniform, the sizes of the plurality of cell masses after being dissociated will be approximately uniform. Alternatively, the first dissociating mechanism 60 may comprise a nozzle. For example, if the interior of an approximately conical nozzle is micromachined in a step-wise manner, a cell mass in the solution will be dissociated into a plurality of cell masses when it passes through the nozzle.

Figure 24:
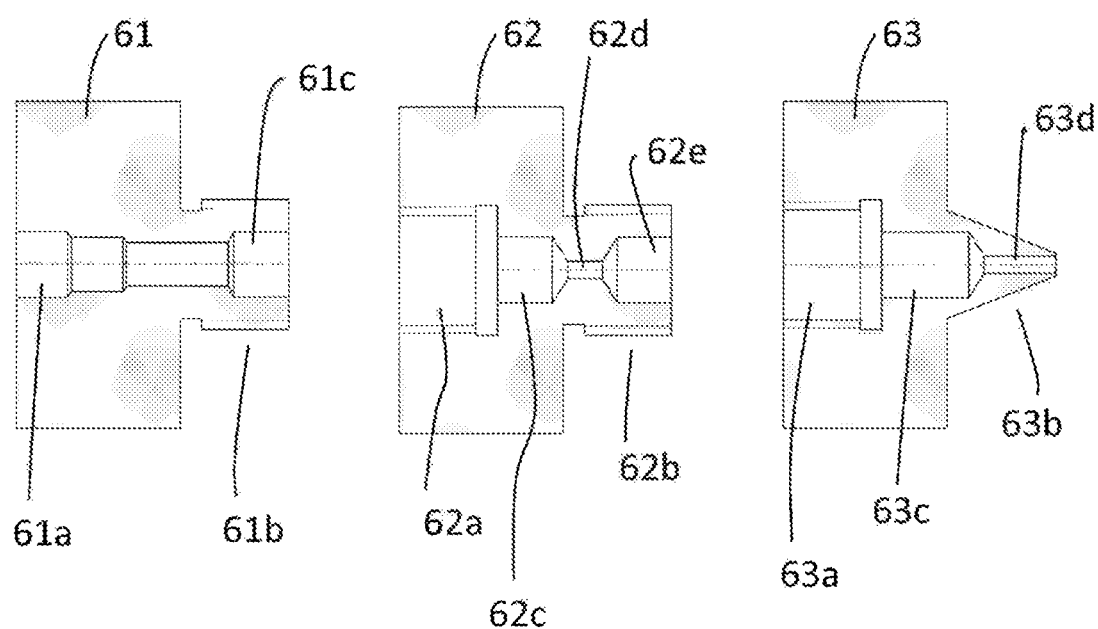
FIG. 24 is a schematic view of a cell mass dissociator according to an embodiment of the invention.
Figure 25:
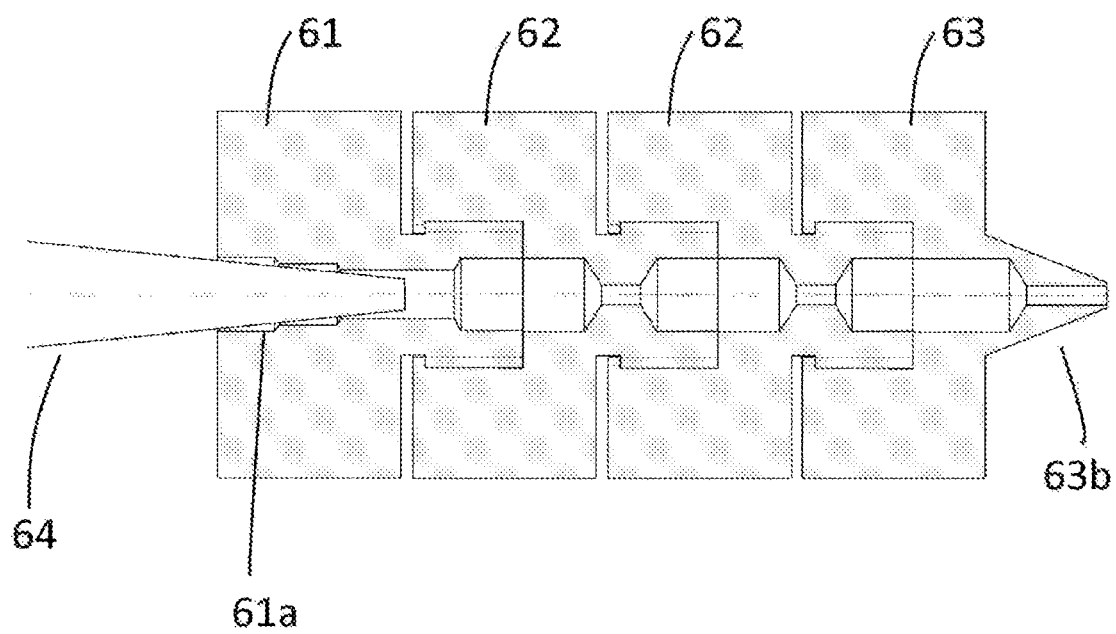
FIG. 25 is a schematic view of a cell mass dissociator according to an embodiment of the invention.
Figure 26:
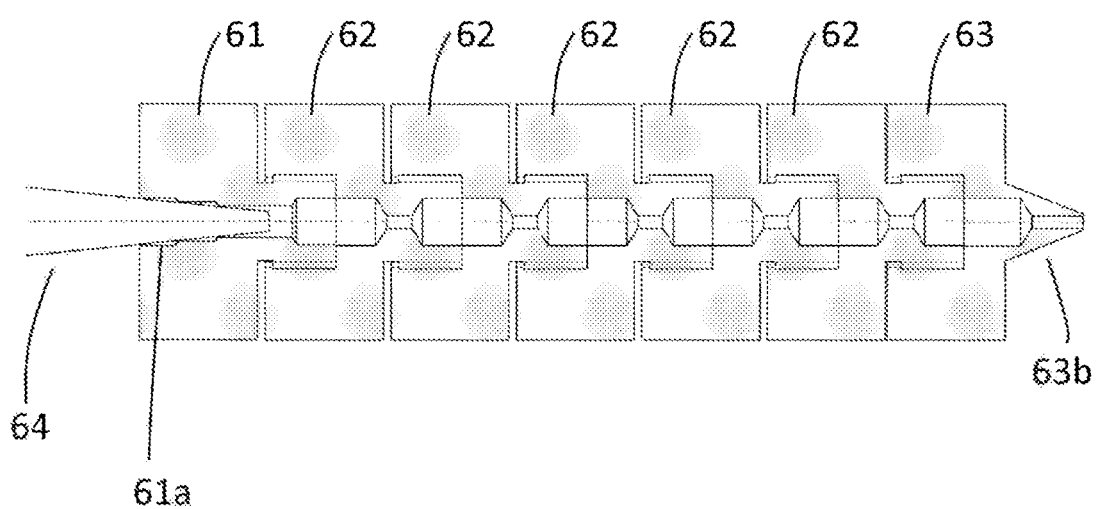
FIG. 26 is a schematic view of a cell mass dissociator according to an embodiment of the invention.

Also alternatively, as shown in FIG. 24, the first dissociating mechanism 60 may comprise a cell mass dissociator comprising a terminal block 61, a connecting block 62 and a tip block 63. The terminal block 61, connecting block 62 and tip block 63 are each provided with a through-hole inside them through which the cell mass-containing culture medium flows. As shown in FIG. 25 and FIG. 26, the terminal block 61, connecting block 62 and tip block 63 are connected. The cell mass dissociator may comprise a single connecting block 62, or it may comprise a plurality of connecting blocks 62.

As shown in FIG. 24, at the first edge of the connecting block 62 there is provided a recess 62*a*, and at the second edge opposite the first edge of the connecting block 62 there is provided a protrusion 62*b*. The protrusion 62*b* is cylindrical, for example. As shown in FIG. 25 and FIG. 26, when a plurality of connecting blocks 62 are used, the protrusions 62*b* engage with the recesses 62*a* of the adjacent connecting blocks 62. The side wall of the protrusion 62*b* shown in FIG. 24 may be smooth, or a male screw may be provided. The inner wall of the recess 62*a* may be smooth, or a female screw may be provided.

The through-hole provided in the connecting block 62 has a first large pore size section 62*c* that connects with the recess 62*a*, a small pore size section 62*d* that connects with the first large pore size section 62*c* and has a smaller pore size than the first large pore size section 62*c*, and a second large pore size section 62*e* that connects with the small pore size section 62*d*, has a larger pore size than the small pore size section 62*d*, and has an opening at the tip of the protrusion 62*b*.

The cross-sectional shapes of the first large pore size section 62*c*, small pore size section 62*d* and second large pore size section 62*e* are circular, for example. The pore size of the first large pore size section 62*c* and the pore size of the second large pore size section 62*e* are the same, for example. Thus, when a plurality of connecting blocks 62 are used and the plurality of connecting blocks 62 are connected, as shown in FIG. 25 and FIG. 26, the second large pore size section 62*e* will smoothly connect with the first large pore size section 62*c* of the adjacent connecting block 62.

The pore sizes of the first and second large pore size sections 62*c*, 62*e* shown in FIG. 24 are, for example, between 2.0 mm and 4.0 mm, inclusive, without any particular restriction to this range. The pore size of the small pore size section 62*d* is, for example, between 0.4 mm and 1.2 mm, inclusive, without any particular restriction to this range. A step is formed at the section connecting from the first large pore size section 62*c* to the small pore size section 62*d*. A step is also formed at the section connecting from the small pore size section 62*d* to the second large pore size section 62*e*. The side walls of the steps may be perpendicular to the central axis of the through-hole, or they may be inclined at less than 90°.

Figure 27:
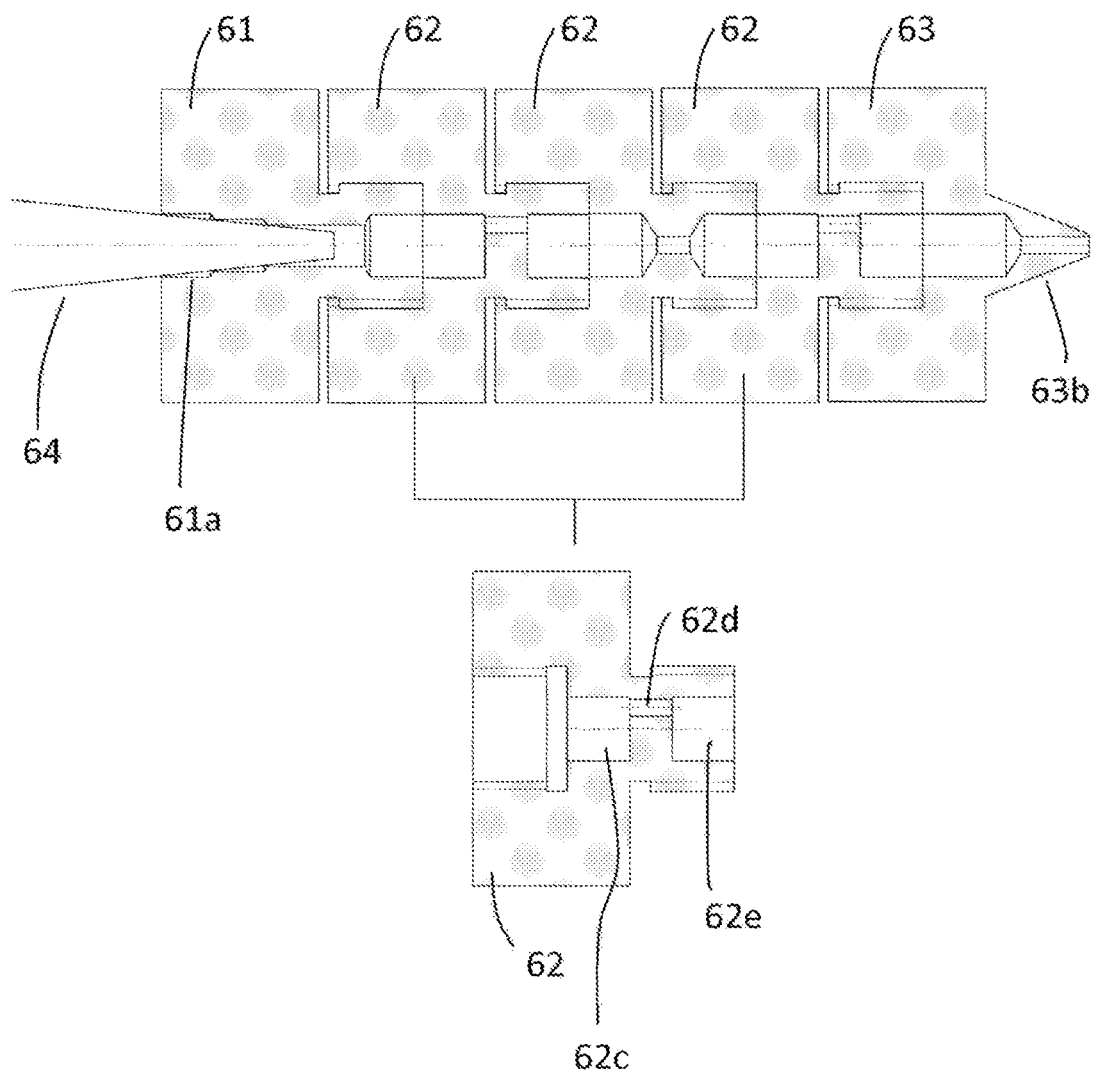
FIG. 27 is a schematic view of a cell mass dissociator according to an embodiment of the invention.

The central axes of the first and second large pore size sections 62*c*, 62*e* and the central axis of the small pore size section 62*d* in the connecting block 62 may match. Alternatively, the central axes of the first and second large pore size sections 62*c*, 62*e* and the central axis of the small pore size section 62*d* in the connecting block 62 may be offset, as shown in FIG. 27.

A recess 63*a* is provided at the first edge of the tip block 63 shown in FIG. 24, and a nozzle solution 63*b* is provided at the second edge opposite the first edge of the tip block 63. When the tip block 63 and the connecting block 62 are connected, the recess 63*a* of the tip block 63 engages with the protrusion 62b of the connecting block 62. The inner wall of the recess 63a may be smooth, or a female screw may be provided.

The through-hole provided in the tip block 63 has a large pore size section 63c that connects with the recess 63a, and a small pore size section 63d that connects with the large pore size section 63c, has a smaller pore size than the large pore size section 63c, and has an opening at the tip of the nozzle section 63b.

The cross-sectional shapes of the large pore size section 63c and the small pore size section 63d are circular, for example. The pore size of the large pore size section 63c of the tip block 63 and the pore size of the second large pore size section 62e of the connecting block 62 are the same, for example. This will allow the second large pore size section 62e of the connecting block 62 and the large pore size section 63c of the adjacent tip block 63 to smoothly connect when the connecting block 62 and the tip block 63 have been connected, as shown in FIG. 25 and FIG. 26.

The pore size of the large pore size section 63c shown in FIG. 24 is, for example, between 2.0 mm and 4.0 mm, inclusive, without any particular restriction to this range. The pore size of the small pore size section 63d is, for example, between 0.4 mm and 1.2 mm, inclusive, without any particular restriction to this range. A step is formed at the section connecting from the large pore size section 63c to the small pore size section 63d. The side walls of the steps may be perpendicular to the central axis of the through-hole, or they may be inclined at less than 90°.

A recess 61a is provided at the first edge of the terminal block 61, and a protrusion 61b is provided at the second edge opposite the first edge of the terminal block 61. When the terminal block 61 and the connecting block 62 are connected, the protrusion 61b of the terminal block engages with the recess 62a of the connecting block 62. The side wall of the protrusion 61b of the terminal block may be smooth, or a male screw may be provided.

The through-hole provided in the terminal block 61 has at least a large pore size section 61c that connects with the recess 61a and has an opening at the tip of the protrusion 61b.

The cross-sectional shapes of the recess 61a and the large pore size section 61c are circular, for example. The pore size of the large pore size section 61c of the terminal block 61 and the pore size of the second large pore size section 62e of the connecting block 62 are the same, for example. This will allow the large pore size section 61c of the terminal block 61 and the large pore size section 62c of the adjacent connecting block 62 to smoothly connect when the terminal block 61 and the connecting block 62 have been connected, as shown in FIG. 25 and FIG. 26.

The pore size of the large pore size section 61c shown in FIG. 24 is, for example, between 2.0 mm and 4.0 mm, inclusive, without any particular restriction to this range.

The materials of the terminal block 61, the connecting block 62 and the tip block 63 may be, but are not restricted to, resins such as polypropylene.

As shown in FIG. 25, FIG. 26 and FIG. 27, an insertion nozzle 64, for example, is inserted in the recess 61a of the terminal block 61. A suction drainer that suction drains the cell mass-containing culture medium, either directly or through a tube or the like, is connected to the insertion nozzle 64. When the terminal block 61, connecting block 62 and tip block 63 are connected, the nozzle section 63b of the tip block 63 is thrust into the cell mass-containing culture medium and suction drainage of the culture medium is carried out once or suction drainage of the culture medium is repeated by the suction drainer, the cell mass-containing culture medium is reciprocated in the through-holes in the connecting block 62 and the tip block 63. Because steps are provided in the through-holes of the connecting block 62 and tip block 63, the cell masses in the culture medium are dissociated into small cell masses in an efficient manner.

Conventionally, dissociation of cell masses has been carried out by a technician using a Pipetman or the like. However, as shown in FIG. 32A, the cell mass sizes dissociated by the conventional method have been non-uniform. Moreover, the obtained cell mass sizes have been variable depending on the technician. If the dissociated cell masses are too large, the nutrients and hormones in the culture medium may fail to reach the interior and the cells may differentiate. In addition, if the cell masses are too small and a ROCK inhibitor is not used, cell death or karyotypic abnormalities may occur. In contrast, by using the cell mass dissociator illustrated in FIG. 25, FIG. 26 and FIG. 27, it is possible to dissociate cell masses into cell masses of uniform sizes, as shown in FIG. 32B. When the cell mass dissociator is used to dissociate cell masses, the culture medium may include enzymes such as trypsin, or TrypLE Express® (ThermoFisher SCIENTIFIC), TrypLE Select® (ThermoFisher SCIENTIFIC) or TrypLE Select® (ThermoFisher SCIENTIFIC). Also, by increasing the number of connecting blocks 62 or raising the pressure during suction drainage of the culture medium, it is possible to degrade the cell masses into single cells.

Figure 28:
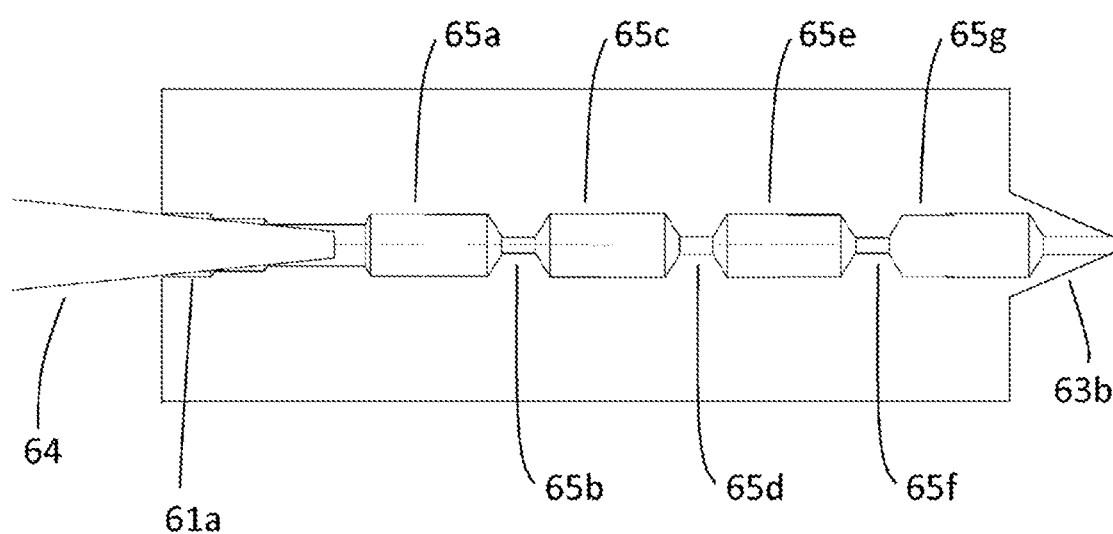
FIG. 28 is a schematic view of a cell mass dissociator according to an embodiment of the invention.
Figure 29:
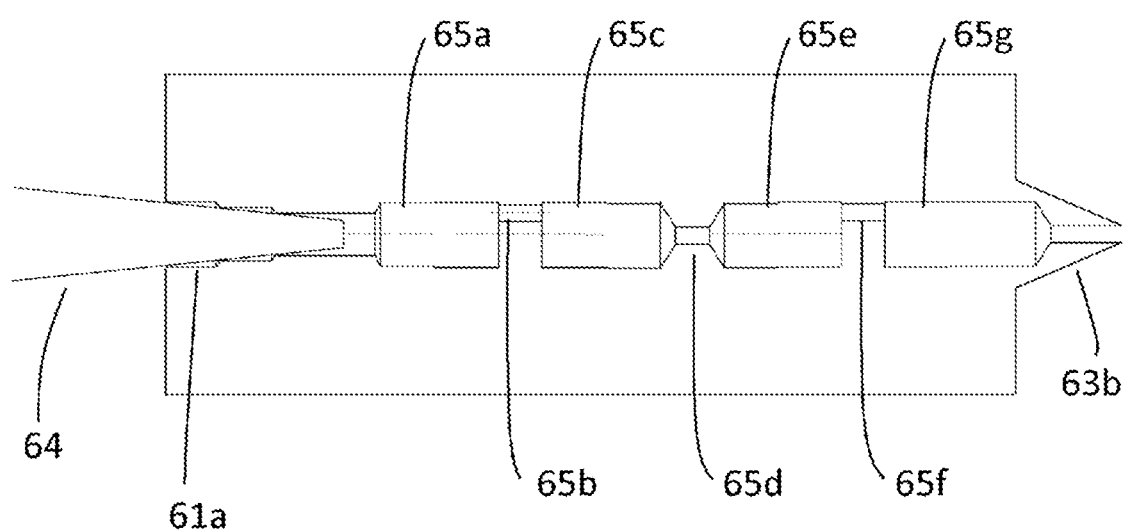
FIG. 29 is a schematic view of a cell mass dissociator according to an embodiment of the invention.

If a suitable number and lengths of repeating large pore size sections and small pore size sections have been determined, the cell mass dissociator does not need to be composed of a plurality of blocks. For example, as shown in FIG. 28, the cell mass dissociator may have an integral cylindrical shape with a through-hole in the interior, the through-hole through which the cell mass-containing culture medium flows having, in an alternating manner, large pore size sections 65a, 65c, 65e, 65g, and small pore size sections 65b, 65d, 65f that connect with the large pore size sections 65a, 65c, 65e, 65g and have smaller pore sizes than the large pore size sections 65a, 65c, 65e, 65g. In this case as well, as shown in FIG. 29, the central axes of the large pore size sections 65a, 65c, 65e, 65g and the central axes of at least some of the small pore size sections 65b, 65d, 65f may be offset.

Figure 30:
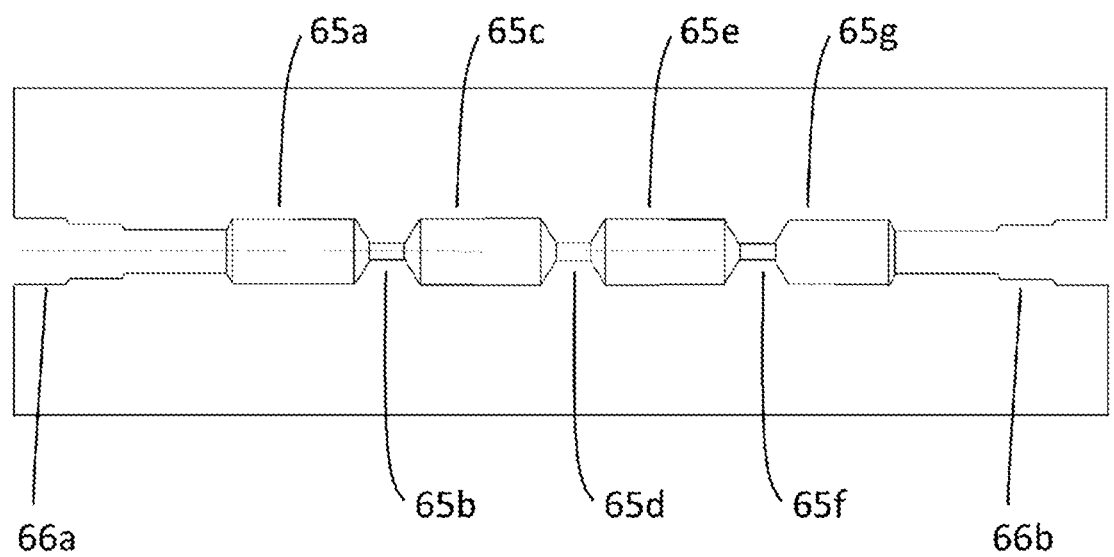
FIG. 30 is a schematic view of a cell mass dissociator according to an embodiment of the invention.
Figure 31:
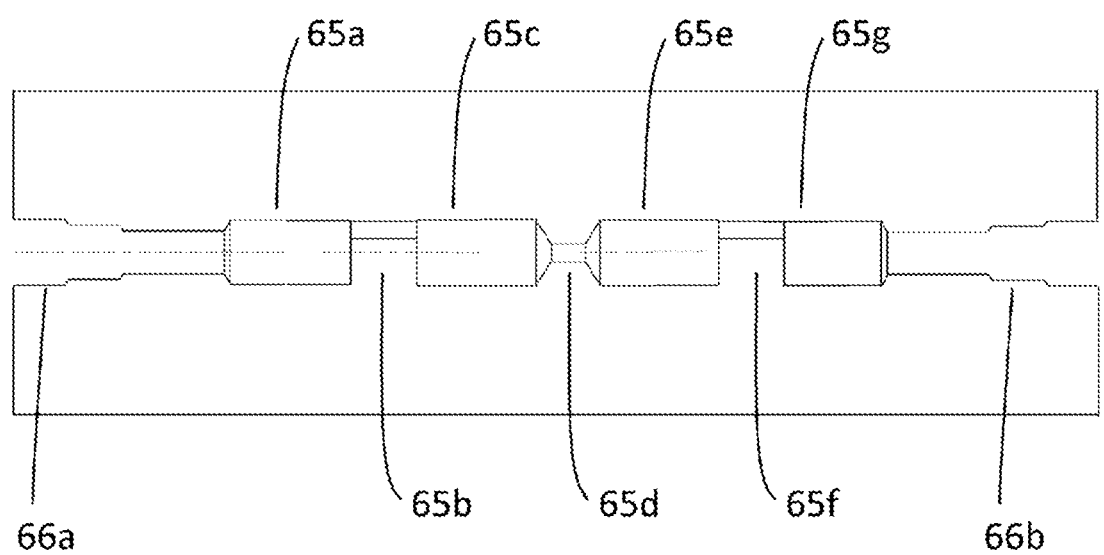
FIG. 31 is a schematic view of a cell mass dissociator according to an embodiment of the invention.

Also, the culture medium may pass through the cell mass dissociator only once to dissociate the cell masses in the culture medium into small cell masses. In this case, as shown in FIG. 30, insertion sections 66a, 66b may be provided to allow insertion of a tube or the like at both ends of the cell mass dissociator. The culture medium passes from the insertion section 66a through the through-hole and is discharged from the insertion section 66b, during which time the cell masses in the culture medium are dissociated. In this case as well, as shown in FIG. 31, the central axes of the large pore size sections 65a, 65c, 65e, 65g and the central axes of at least some of the small pore size sections 65b, 65d, 65f may be offset.

The amplifying culturing apparatus 70 is connected to the first dissociating mechanism 60 shown in FIG. 1. The solution including cell masses that have been dissociated at the first dissociating mechanism 60 is fed to the amplifying culturing apparatus 70.

The amplifying culturing apparatus 70 can house a well plate in its interior. The amplifying culturing apparatus 70 also comprises a pipetting machine. The amplifying culturing apparatus 70 receives the solution including the plurality of cell masses from the first dissociating mechanism 60, and the solution is allocated into the wells with a pipetting machine. After allocating the cell masses into the wells, the amplifying culturing apparatus 70 cultures the cell masses for about 8 days, for example, at 37° C., 5% $CO_2$. The amplifying culturing apparatus 70 also carries out appropriate exchange of the culture medium.

The amplifying culturing apparatus 70 then adds a trypsin-substituting recombinant enzyme such as TrypLE Select® (Life Technologies Corp.) to the cell masses. In addition, the amplifying culturing apparatus 70 places a vessel containing the cell masses in an incubator, and reacts the cell masses with the trypsin-substituting recombinant enzyme for 1 minute at 37° C., 5% $CO_2$. When the cell masses are to be physically disrupted, there is no need for a trypsin-substituting recombinant enzyme. For example, the amplifying culturing apparatus 70 disrupts the cell masses by pipetting with a pipetting machine. Alternatively, the amplifying culturing apparatus 70 may disrupt the cell masses by passing the cell masses through a pipe provided with a filter, or a pipe that intermittently varies the inner diameter, similar to the introduced cell solution-feeding channel 31 shown in FIG. 2 or FIG. 3. The amplifying culturing apparatus 70 then adds culture medium such as maintenance culture medium to the solution containing the cell masses. Furthermore, when the amplifying culturing apparatus 70 carries out adhesion culture, the cell masses are scraped from the vessel with an automatic cell scraper or the like, and the cell mass-containing solution is fed to the first dissociating mechanism 60 through an amplifying culturing solution-feeding channel 71.

Culturing in the amplifying culturing apparatus 70 may be carried out in a $CO_2$-permeable bag instead of a well plate. In addition, the culturing may be by adhesion culture, or by suspension culture, or by hanging drop culture. In the case of suspension culture, agitation culture may be carried out. The culture medium may also be in the form of agar. Agar culture media include gellan gum polymers. When agar culture medium is used, there is no settling or adhesion of cells, and therefore agitation is not necessary even though it is suspension culture.

The amplifying culturing apparatus 70 may also comprise a second culture medium supply device that supplies culture solution to the well plate or $CO_2$-permeable bag. The second culture medium supply device collects the culture solution in the well plate or $CO_2$-permeable bag, and it may use a filter or dialysis membrane to filter the culture solution, to allow reuse of the purified culture solution. During this time, growth factors or the like may be added to the culture solution that is to be reused. The amplifying culturing apparatus 70 may also comprise a temperature regulating device that regulates the temperature of the culture medium, and a humidity control device that controls the humidity in the vicinity of the culture medium.

In the amplifying culturing apparatus 70 as well, the cells may be placed in a culture solution-permeable bag 301 such as a dialysis membrane as shown in FIG. 4, for example, and the culture solution-permeable bag 301 may be placed in a culture solution-impermeable $CO_2$-permeable bag 302, so that the culture solution is placed in bags 301, 302. The initializing culturing apparatus 50 may have multiple bags 302 prepared containing fresh culture solution, and the bag 302 in which the cell-containing bag 301 is placed may be replaced by a bag 302 containing fresh culture solution, at prescribed intervals of time.

The culturing method in the amplifying culturing apparatus 70 is not limited to the method described above, and may employ a suspension culture vessel such as shown in FIG. 5, similar to the culturing method in the initializing culturing apparatus 50. In the amplifying culturing apparatus 70, the plurality of cell masses are to be placed in the dialysis tube 75 of the suspension culture vessel shown in FIG. 5. The details regarding the suspension culture vessel are as explained above. In the amplifying culturing apparatus 70 as well, a supply culture medium solution-feeding pump 77 may be used as shown in FIG. 6, for exchange and supply of the gel medium surrounding the dialysis tube 75 in the vessel 76. Alternatively, as shown in FIG. 7, the supply culture medium solution-feeding pump 77 and the interior of the dialysis tube 75 in the suspension culture vessel 76 may be connected by the solution-feeding tube 78, to supply the components necessary for culturing of cells in the culture medium in the dialysis tube 75.

The stem cell production system shown in FIG. 1 may further comprise an amplifying culturing photographing device that photographically records culturing in the amplifying culturing apparatus 70. If a colorless culture medium is used for the culture medium in the amplifying culturing apparatus 70, it will be possible to minimize diffuse reflection and autologous fluorescence that may be produced when using a colored culture medium. In order to confirm the pH of the culture medium, however, a pH indicator such as phenol red may be included. Moreover, since induced cells and non-induced cells have differences in cellular shape and size, the stem cell production system may further comprise an induced state monitoring device that calculates the proportion of induced cells by photographing the cells in the amplifying culturing apparatus 70. Alternatively, the induced state monitoring device may determine the proportion of induced cells by antibody immunostaining or RNA extraction. In addition, the stem cell production system may comprise a non-induced cell removing device that removes cells that have not been induced, by magnetic-activated cell sorting, flow cytometry or the like.

The amplifying culturing photographing device is similar to the initializing culturing photographing device 171 shown in FIG. 8, and it may photograph culturing in the amplifying culturing apparatus 70 through a telecentric lens 172. The illumination method during photography by the amplifying culturing photographing device may also be the same as the illumination method during photography by the initializing culturing photographing device 171, which is as described above.

The amplifying culturing photographing device is also connected to a CPU 500 comprising an image processor 501, as shown in FIG. 11. The image processor 501 comprising the outline defining unit 511, cell evaluating unit 512, statistical processor 513, density calculating unit 514 and culture medium evaluating unit 515 performs image processing on the image taken by the amplifying culturing photographing device, similar to the image taken by the initializing culturing photographing device 171. The details regarding the image processor 501 are as described above.

For example, if the cell mass grows too large during amplifying culturing, the nutrients and hormones in the culture medium may fail to reach the interior and the cells may differentiate. In addition, if cell masses that are too small are subcultured, without using a ROCK inhibitor, cell death or karyotypic abnormalities may occur. Consequently, the cell evaluating unit 512 may emit an alert when the individual cell mass sizes are outside of the suitable range. In addition, the cell evaluating unit 512 may output a timing for subculturing when the individual cell mass sizes are beyond a prescribed threshold value. In this case, the cell masses may be fragmented to reduce the sizes of the individual cell masses, and subcultured by resuming culturing in the culturing vessel. In addition, if the individual cell mass sizes after fragmentation of the cell masses are calculated during the subculturing, it is possible to judge whether or not the fragmentation has been adequate. Furthermore, the supply rate of culture medium at the amplifying culturing apparatus 70 may be varied according to the calculated cell mass sizes. For example, the supply rate of the culture medium may be increased as the cell mass sizes increase.

The supply rate of culture medium at the amplifying culturing apparatus 70 may also be varied according to the number of cell masses calculated by the statistical processor 513. For example, the supply rate of the culture medium may be increased as the number of cell masses increases.

The density calculating unit 514 may also output a timing for subculturing, when the cell mass density has reached at least at prescribed threshold value. When the cell mass density has become higher than the suitable range, the cell mass density may be adjusted to within the suitable range by subculturing, for example. In addition, if the cell mass density after fragmentation of the cell masses is calculated during the subculturing, it is possible to judge whether or not the fragmentation has been adequate. Furthermore, the supply rate of culture medium at the amplifying culturing apparatus 70 may be varied according to the calculated cell mass density. For example, the supply rate of the culture medium may be increased as the cell mass density increases.

When the culture medium evaluating unit 515 has judged that the culture medium hue or the culture medium pH is outside of the prescribed range, the culture medium surrounding the dialysis tube 75 of the suspension culture vessel is exchanged by the supply culture medium solution-feeding pump 77 shown in FIG. 6, for example, at the amplifying culturing apparatus 70 as well. Alternatively, when the culture medium is being constantly exchanged, the exchange rate of the culture medium surrounding the dialysis tube 75 of the suspension culture vessel by the supply culture medium solution-feeding pump 77 increases, and the flow rate of the exchanged culture medium increases. This allows the culture medium pH to be maintained within a range suitable for cell culturing, and allows sufficient nutrients to be supplied to the culture medium.

The cell masses that have been dissociated by the first dissociating mechanism 60 shown in FIG. 1 are again cultured in the amplifying culturing apparatus 70. Dissociation of the cell masses at the first dissociating mechanism 60 and culturing of the cell masses in the amplifying culturing apparatus 70 are repeated until the necessary cell volume is obtained.

The pump that delivers the cell mass-containing solution in the amplifying culturing apparatus 70 to the first dissociating mechanism 60 through the amplifying culturing solution-feeding channel 71 may be driven when, for example, the value of the cell mass size calculated by the cell evaluating unit 512 shown in FIG. 11 is at least a prescribed threshold value. Alternatively, the pump that delivers the cell mass-containing solution to the first cell mass solution-feeding channel 51 shown in FIG. 1 may be driven when, for example, the value of the cell mass density calculated by the density calculating unit 514 shown in FIG. 11 is at least a prescribed threshold value.

A second cell mass solution-feeding channel 72 is connected to the amplifying culturing apparatus 70. The amplifying culturing apparatus 70 delivers the cell mass-containing solution, that has been amplifying cultured and detached from the vessel, to the second cell mass solution-feeding channel 72 using a pump or the like. However, detachment is not necessary in the case of suspension culture. The second cell mass solution-feeding channel 72 may have an inner diameter that allows passage of only induced cells of less than a prescribed size, and it may be connected to a branched fluid channel that removes non-induced cells of a prescribed size or larger.

The inner wall of the second cell mass solution-feeding channel 72 may be coated with poly-HEMA to render it non-cell-adherent, so that the cells do not adhere. Alternatively, a material resistant to cell adhesion may be used as the material for the second cell mass solution-feeding channel 72. Also, by using a material with good thermal diffusivity and $CO_2$ permeability as the material of the second cell mass solution-feeding channel 72, the conditions in second cell mass solution-feeding channel 72 will be equivalent to the controlled temperature and $CO_2$ concentration in the enclosure 200. In addition, a back-flow valve may be provided in the second cell mass solution-feeding channel 72 from the viewpoint of preventing contamination.

The second cell mass solution-feeding channel 72 is connected to the second dissociating mechanism 80. The second dissociating mechanism 80 comprises a mesh, for example. The cell masses in the solution are dissociated into a plurality of cell masses of the sizes of the holes of the mesh, when they pass through the mesh by water pressure. For example, if the mesh hole sizes are uniform, the sizes of the plurality of cell masses after being dissociated will be approximately uniform. Alternatively, the second dissociating mechanism 80 may comprise a nozzle. For example, if the interior of an approximately conical nozzle is micromachined in a step-wise manner, a cell mass in the solution will be dissociated into a plurality of cell masses when it passes through the nozzle.

Alternatively, the second dissociating mechanism 80, similar to the first dissociating mechanism 60, may comprise a cell mass dissociator comprising a terminal block 61, connecting block 62 and tip block 63 as shown in FIG. 24 to FIG. 27, or an integral cell dissociator as shown in FIG. 28 to FIG. 31. The details regarding the cell mass dissociator are as explained above.

The cell mass transport mechanism 90 that successively sends the plurality of cell masses to the packaging device 100 is connected to the second dissociating mechanism 80 shown in FIG. 1. A pre-packaging cell channel 91 is connected between the cell mass transport mechanism 90 and the packaging device 100. The cell mass transport mechanism 90 employs a pump or the like to send each of the cell masses that have been dissociated by the second dissociating mechanism 80, to the packaging device 100 through the pre-packaging cell channel 91.

The pre-packaging cell channel 91 is coated with poly-HEMA so that the cells do not adhere. Alternatively, a material resistant to cell adhesion may be used as the material for the pre-packaging cell channel 91. Also, by using a material with good thermal diffusivity and $CO_2$ permeability as the material of the pre-packaging cell channel 91, the conditions in the pre-packaging cell channel 91 will be equivalent to the controlled temperature and $CO_2$ concentration in the enclosure 200. In addition, a back-flow valve may be provided in the pre-packaging cell channel 91 from the viewpoint of preventing contamination.

A cryopreservation liquid solution-feeding mechanism 110 is connected to the pre-packaging cell channel 91. The cryopreservation liquid solution-feeding mechanism 110 feeds a cell cryopreservation liquid into the pre-packaging cell channel 91. As a result, the cell masses are suspended in the cell cryopreservation liquid inside the pre-packaging cell channel 91.

The packaging device 100 freezes each of the plurality of cell masses in order, that have been fed through the pre-packaging cell channel 91. For example, each time it receives cell masses, the packaging device 100 places the cell masses in a cryopreservation vessel such as a cryotube, and immediately freezes the cell mass solution at −80° C. or below, for example. When using a cryopreservation vessel with a small surface area per volume, more time will tend to be necessary for freezing, and therefore it is preferred to use a cryopreservation vessel with a large surface area per volume. By using a cryopreservation vessel with a large surface area per volume it is possible to increase the survival rate of the cells after thawing. The shape of the cryopreservation vessel may be capillary-like or spherical, without any particular restrictions. Immediate freezing is not necessarily essential, depending on the survival rate required for the cells after thawing.

Vitrification, for example, may be employed for the freezing. In this case, the cell cryopreservation liquid used may be DAP213 (Cosmo Bio Co., Ltd.) or Freezing Medium (ReproCELL, Inc.). The freezing may also be carried out by a common method other than vitrification. In this case, the cell cryopreservation liquid used may be CryoDefend-Stem Cell (R&D Systems) or STEM-CELLBANKER® (Zenoaq). The freezing may be carried out with liquid nitrogen, or it may be carried out with a Peltier element. When a Peltier element is used, temperature changes can be controlled and temperature variation can be minimized. The packaging device 100 carries the cryopreservation vessel out of the enclosure 200. When the frozen cells are to be used in the clinic, the cryopreservation vessel is preferably a completely closed system. However, the packaging device 100 may package the stem cells in a preservation vessel without freezing.

Alternatively, in the packaging device 100, the cell mass solution may be exchanged from the culture medium to the cryopreservation liquid using a solution exchanger 101 as illustrated in FIGS. 33A to 33G. Inside the solution exchanger 101 there is provided a filter 102 having at the bottom a fine hole which does not permit passage of cell masses. In the solution exchanger 101 there is also provided a cell mass introduction hole where a first solution-feeding channel 103 that delivers cell mass-containing culture medium onto the internal filter 102 is connected, an exchange solution introduction hole where a second solution-feeding channel 104 that delivers cell mass-free frozen solution onto the internal filter 102 is connected, and a cell mass outflow hole where a first discharge channel 105 that discharges cell mass-containing frozen solution onto the internal filter 102 is connected. There is also provided in the solution exchanger 101 a waste liquid outflow hole wherein there is connected a second discharge channel 106 that discharges solution that has passed through the filter 102. Tubes or the like may be used for each of the first solution-feeding channel 103, second solution-feeding channel 104, first discharge channel 105 and second discharge channel 106.

Figures 33A, 33B, 33C, 33D, 33E, 33F, 33G:
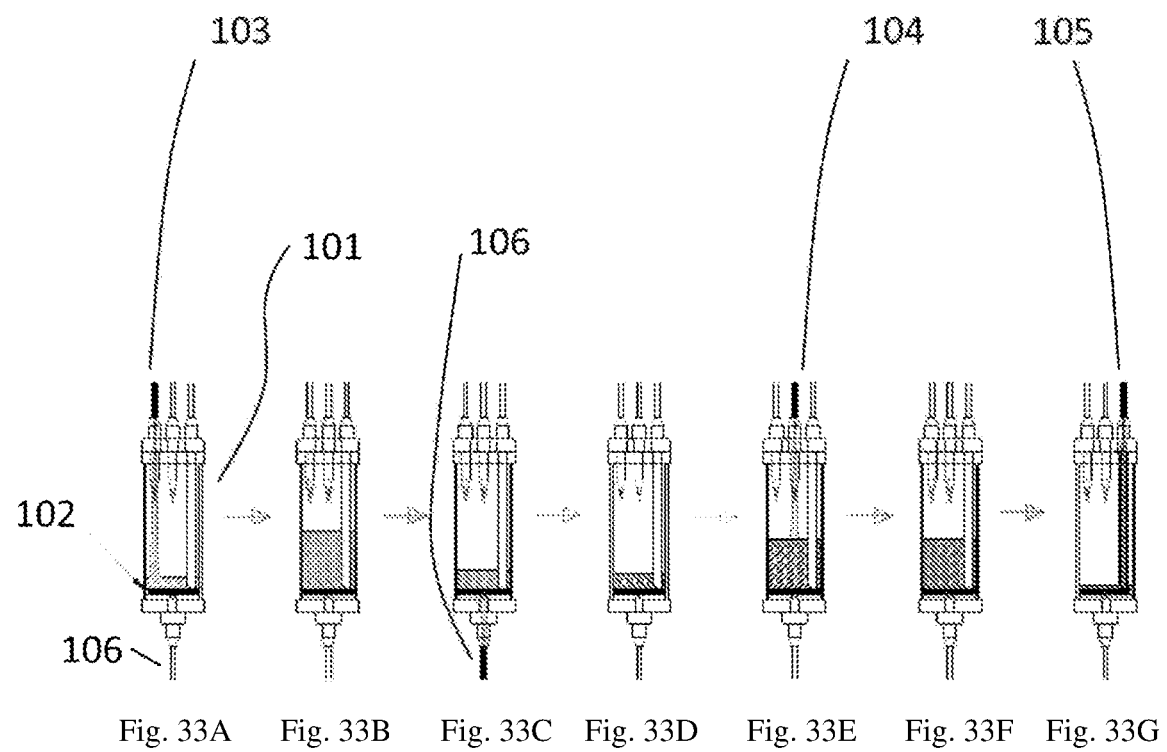
FIGS. 33A to 33G are schematic views of a solution exchanger according to an embodiment of the invention.

First, as shown in FIG. 33A and FIG. 33B, cell mass-containing culture medium is placed inside the solution exchanger 101 from the first solution-feeding channel 103, while flow of the solution in the second discharge channel 106 is stopped. Next, as shown in FIG. 33C, a state is formed allowing flow of the solution in the second discharge channel 106, and the culture medium is discharged from the solution exchanger 101. The cell mass remains on the filter 102 during this time, as shown in FIG. 33D. First, as shown in FIG. 33E and FIG. 33F, the cryopreservation liquid is placed inside the solution exchanger 101 from the second solution-feeding channel 104, while flow of the solution in the second discharge channel 106 is stopped, and the cell masses are dispersed in the cryopreservation liquid. Next, as shown in FIG. 33G, the cell mass-containing cryopreservation liquid is discharged from the first discharge channel 105. The cell mass-containing cryopreservation liquid is sent to a cryopreservation vessel or the like through the first discharge channel 105.

The solution exchanger 101 shown in FIGS. 33A to 33G may be used not only for exchange from culture medium to cryopreservation liquid, but also for exchange from old culture medium to fresh culture medium. In this case, the second solution-feeding channel 104 delivers fresh culture medium.

Alternatively, when dissociating the cell masses, the solution exchanger 101 may be used for exchange of the culture medium with solution containing a cell mass dissociating enzyme. Examples of cell mass dissociating enzymes include trypsin, and trypsin-substituting recombinant enzymes such as TrypLE Select® (Life Technologies Corp.). In this case, the second solution-feeding channel 104 delivers solution containing a cell mass dissociating enzyme.

The stem cell production system shown in FIG. 1 may further comprise a packaging step photographing device in which the packaging step is photographed at the packaging device 100.

The stem cell production system may still further comprise a sterilizing device that performs sterilization inside the enclosure 200. The sterilizing device may be a dry heat sterilizing device. In this case, the wirings of the devices that use electricity, such as the separating device 10, preintroduction cell solution-feeding channel 20, inducing factor solution-feeding mechanism 21, factor introducing device 30, cell mass preparation device 40 and packaging device 100, are preferably heat-resistant wirings. Alternatively, the sterilizing device may emit sterilizing gas such as ozone gas, hydrogen peroxide gas or formalin gas into the enclosure 200, to sterilize the interior of the enclosure 200.

The stem cell production system may also record the behavior of the separating device 10, preintroduction cell solution-feeding channel 20, inducing factor solution-feeding mechanism 21, factor introducing device 30, cell mass preparation device 40 and packaging device 100, and may transmit the image taken by the photographing device to an external server, in either a wired or wireless manner. At the external server, factors such as the conditions including the inducing factor introduction conditions, the culturing conditions and the freezing conditions, and results such as incomplete initialization of the stem cells, failed differentiation and growth of the stem cells and chromosomal aberrations, for example, are analyzed by a neural network, and the conditions leading to results may be extracted and results predicted. In addition, the external server may control the separating device 10, inducing factor solution-feeding mechanism 21, factor introducing device 30, cell mass preparation device 40 and packaging device 100 of the stem cell production system based on a standard operation procedure (SOP), monitor whether or not each device is running based on the SOP, and automatically produce a running record for each device.

With the stem cell production system described above, it is possible to carry out induction, establishment, amplifying culturing and cryopreservation of stem cells such as iPS cells, fully automatically in a single process.

The stem cell production system of this embodiment is not limited to the construction illustrated in FIG. 1. For example, in the stem cell production system of the embodiment shown in FIG. 34, blood is delivered from the blood storing unit 201 to the mononuclear cell separating unit 203, through a blood solution-feeding channel 202. Tubes, for example, may be used as the blood storing unit 201 and mononuclear cell separating unit 203. The blood solution-feeding channel 202 is a resin tube or silicon tube, for example. This also applies for the other solution-feeding channels described below. An identifier such as a barcode is attached to the blood storing unit 201 for control of the blood information. A pump 204 is used for feeding of the solution. The pump 204 that is used may be a positive-displacement pump. Examples of positive-displacement pumps include reciprocating pumps including piston pumps, plunger pumps and diaphragm pumps, and rotating pumps including gear pumps, vane pumps and screw pumps. Examples of diaphragm pumps include tubing pumps and piezoelectric pumps. Examples of tubing pumps include Peristaltic Pump® (Atto Corp.) and RP-Q1 and RP-TX (Takasago Electric, Inc.). Examples of piezoelectric pumps include SDMP304, SDP306, SDM320 and APP-20KG (Takasago Electric, Inc.). A microflow chip module (Takasago Electric, Inc.) comprising a combination of various different pumps may also be used. When a sealed pump such as a Peristaltic Pump®, tubing pump or diaphragm pump is used, delivery can be accomplished without direct contact of the pump with the blood inside the blood solution-feeding channel 202. The same also applies to the other pumps described below. Alternatively, syringe pumps may be used for the pump 204, and for the pump 207, pump 216, pump 222, pump 225, pump 234, pump 242 and pump 252 described below. Even pumps other than sealed pumps may be reutilized after heat sterilization treatment.

An erythrocyte coagulant is fed to the mononuclear cell separating unit 203 from the separating agent storing device 205, through a solution-feeding channel 206 and the pump 207. Tubes, for example, may be used as the separating agent storing device 205. An identifier such as a barcode is attached to the separating agent storing device 205 for control of the separating agent information. The erythrocyte coagulant used may be, for example, HetaSep® (STEMCELL Technologies) or an Erythrocyte Coagulant (Nipro Corp.). In the mononuclear cell separating unit 203, the erythrocytes precipitate by the erythrocyte coagulant and the mononuclear cells are separated. The mononuclear cell-containing supernatant in the mononuclear cell separating unit 203 is sent to a mononuclear cell purifying filter 210 through a mononuclear cell solution-feeding channel 208 and pump 209. At the mononuclear cell purifying filter 210, components other than the mononuclear cells are removed to obtain a mononuclear cell-containing solution. The mononuclear cell purifying filter 210 used may be Purecell® (PALL), Cellsorba E (Asahi Kasei Corp.), SEPACELL PL (Asahi Kasei Corp.), ADACOLUMN® (Jimro), or a separation bag (Nipro Corp.).

Figure 34:
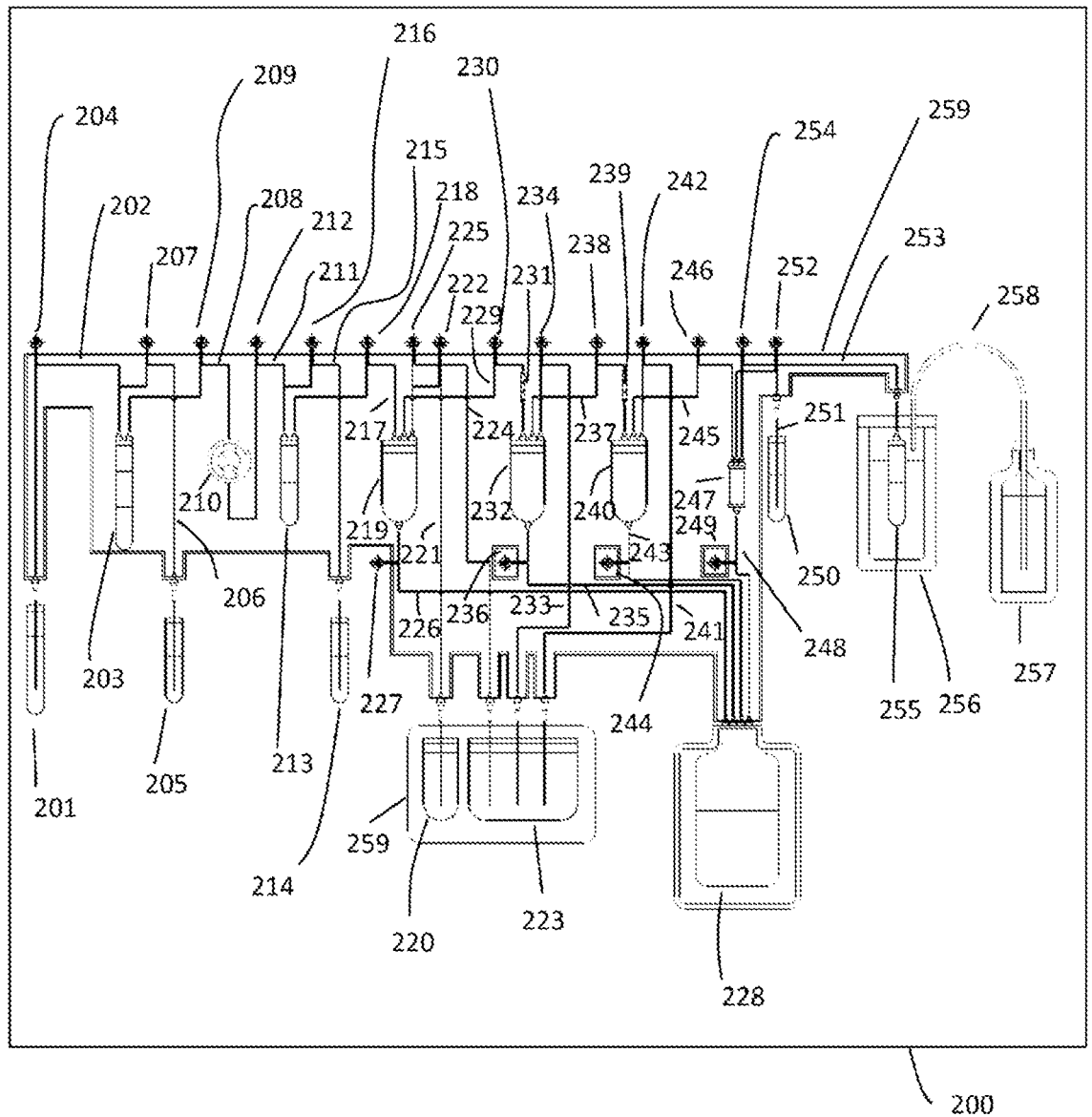
FIG. 34 is a schematic view of a stem cell production system according to an embodiment of the invention.

In FIG. 34, the mononuclear cell separating unit 203, separating agent storing device 205, mononuclear cell purifying filter 210 and pumps 204, 207, 209 constitute a separating device.

The mononuclear cell-containing solution is sent to a factor introducing device 213 through a preintroduction cell solution-feeding channel 211 and pump 212. Tubes, for example, may be used as the factor introducing device 213. Pluripotency inducing factors are fed to the factor introducing device 213 from a factor storing device 214 including pluripotency inducing factors, through a factor solution-feeding channel 215 and the pump 216. Tubes, for example, may be used as the factor storing device 214. An identifier such as a barcode is attached to the factor storing device 214 for control of the pluripotency inducing factor information. The factor storing device 214 and the pump 216 constitute the inducing factor solution-feeding mechanism. In the factor introducing device 213 as the factor introducing device, the pluripotency inducing factors are introduced into cells by RNA lipofection, for example, and inducing factor-introduced cells are prepared. However, the method of transfection of the inducing factor is not limited to RNA lipofection. For example, Sendai virus vector including pluripotency inducing factors may be used. Alternatively, the pluripotency inducing factor may be a protein.

The inducing factor-introduced cells are sent through an introduced cell solution-feeding channel 217 and pump 218 to an initializing culturing vessel 219 as a part of the cell mass preparation device. The introduced cell solution-feeding channel 217 is, for example, temperature-permeable and $CO_2$-permeable. The suspension culture vessel shown in FIG. 5 may be used as the initializing culturing vessel 219. In this case, the inducing factor-introduced cells are placed in a dialysis tube. For the first few days after introduction of the pluripotency inducing factors to the cells, blood cell culture medium is supplied to the initializing culturing vessel 219 shown in FIG. 34 from a blood cell culture medium storing unit 220 including blood cell culture medium, through a culture medium solution-feeding channel 221 and pump 222. The culture medium solution-feeding channel 221 is, for example, temperature-permeable and $CO_2$-permeable. An identifier such as a barcode is attached to the blood cell culture medium storing unit 220 for control of the blood cell culture medium information. The blood cell culture medium storing unit 220, culture medium solution-feeding channel 221 and pump 222 constitute the culture medium supply device. The pump 222 may continuously supply blood cell culture medium, or it may supply blood cell culture medium at a prescribed timing, according to directions by the CPU 500 shown in FIG. 11.

Next, stem cell culture medium is supplied to the initializing culturing vessel 219 shown in FIG. 34, from a stem cell culture medium storing unit 223 including stem cell culture medium, through a culture medium solution-feeding channel 224 and pump 225. An identifier such as a barcode is attached to the stem cell culture medium storing unit 223 for control of the stem cell culture medium information. The culture medium solution-feeding channel 224 is, for example, temperature-permeable and $CO_2$-permeable. The stem cell culture medium storing unit 223, culture medium solution-feeding channel 224 and pump 225 constitute the culture medium supply device. The pump 225 may continuously supply stem cell culture medium, or it may supply stem cell culture medium at a prescribed timing, according to directions by the CPU 500 shown in FIG. 11.

The blood cell culture medium storing unit 220 and stem cell culture medium storing unit 223 may be placed in cold storage in the cold storage section 259 at a low temperature of 4° C., for example. The culture medium fed from the blood cell culture medium storing unit 220 and the stem cell culture medium storing unit 223 may be fed to the culturing vessel, for example, after having the temperature raised to 37° C. with a heater outside the cold storage section 259. Alternatively, the temperature surrounding the solution-feeding channel may be set so that the culture medium stored at low temperature increases in temperature to 37° C. while it progresses through the solution-feeding channel. The used culture medium in the initializing culturing vessel 219 is sent to a waste liquid storage section 228 through a waste liquid solution-feeding channel 226 and pump 227. An identifier such as a barcode is attached to the waste liquid storage section 228 for control of the waste liquid information.

The cell masses that have been cultured at the initializing culturing vessel 219 are sent to a first amplifying culturing vessel 232 as a part of the cell mass preparation device, through an introduced cell solution-feeding channel 229, pump 230 and cell mass dissociator 231. The cell mass dissociator 231 may also comprise the construction shown in FIG. 30 or FIG. 31, for example. By passing through the cell mass dissociator 231, the cell masses are dissociated into smaller cell masses. The suspension culture vessel shown in FIG. 5 may be used as the first amplifying culturing vessel 232 shown in FIG. 34. In this case, the cell masses are placed in a dialysis tube. Stem cell culture medium is supplied to the first amplifying culturing vessel 232 shown in FIG. 34, from the stem cell culture medium storing unit 223 including stem cell culture medium, through a culture medium solution-feeding channel 233 and pump 234. The introduced cell solution-feeding channel 229 and culture medium solution-feeding channel 233 are, for example, temperature-permeable and $CO_2$-permeable. The stem cell culture medium storing unit 223, culture medium solution-feeding channel 233 and pump 234 constitute the culture medium supply device. The pump 234 may continuously supply stem cell culture medium, or it may supply stem cell culture medium at a prescribed timing, according to directions by the CPU 500 shown in FIG. 11.

The used culture medium in the first amplifying culturing vessel 232 shown in FIG. 34 is sent to the waste liquid storage section 228 through a waste liquid solution-feeding channel 235 and pump 236.

The cell masses that have been cultured at the first amplifying culturing vessel 232 are sent to a second amplifying culturing vessel 240 as a part of the cell mass preparation device, through an introduced cell solution-feeding channel 237, pump 238 and cell mass dissociator 239. The cell mass dissociator 239 may also comprise the construction shown in FIG. 30 or FIG. 31, for example. By passing through the cell mass dissociator 239, the cell masses are dissociated into smaller cell masses. The suspension culture vessel shown in FIG. 5 may be used as the second amplifying culturing vessel 240 shown in FIG. 34. In this case, the cell masses are placed in a dialysis tube. Stem cell culture medium is supplied to the second amplifying culturing vessel 240 shown in FIG. 34, from the stem cell culture medium storing unit 223 including stem cell culture medium, through a culture medium solution-feeding channel 241 and pump 242. The introduced cell solution-feeding channel 237 and culture medium solution-feeding channel 241 are, for example, temperature-permeable and $CO_2$-permeable. The stem cell culture medium storing unit 223, culture medium solution-feeding channel 241 and pump 242 constitute the culture medium supply device. The pump 242 may continuously supply stem cell culture medium, or it may supply stem cell culture medium at a prescribed timing, according to directions by the CPU 500 shown in FIG. 11.

The used culture medium in the second amplifying culturing vessel 240 shown in FIG. 34 is sent to the waste liquid storage section 228 through a waste liquid solution-feeding channel 243 and pump 244.

The cell masses that have been cultured in the second amplifying culturing vessel 240 are sent to a solution exchanger 247 through an introduced cell solution-feeding channel 245 and pump 246. The solution exchanger 247 comprises the construction shown in FIGS. 33A to 33G, for example. In the solution exchanger 247 shown in FIG. 34, the cell masses are held at a filter while the culture medium is sent to the waste liquid storage section 228 through a waste liquid solution-feeding channel 248 and pump 249.

After stopping flow of the solution in the waste liquid solution-feeding channel 248 by stopping driving of the pump 249, or after closing the waste liquid solution-feeding channel 248 with a valve or the like, cryopreservation liquid is placed in the solution exchanger 247 from a cryopreservation liquid storing device 250 that includes cryopreservation liquid, through a solution-feeding channel 251 and pump 252. This disperses the cell masses in the cryopreservation liquid.

The cryopreservation liquid that has dispersed the cell masses is fed into a cryopreservation vessel 255 through a solution-feeding channel 253 and pump 254, as parts of the packaging device. The cryopreservation vessel 255 is situated in a low-temperature repository 256. Liquid nitrogen at −80° C., for example, is fed to the low-temperature repository 256 from a liquid nitrogen repository 257, through a solution-feeding channel 258. The cell masses in the cryopreservation vessel 255 are thus frozen. However, freezing of the cell masses does not need to be by liquid nitrogen. For example, the low-temperature repository 256 may be a freezer such as a compression freezer, an absorption freezer or a Peltier freezer.

Back-flow valves may also be provided in the solution-feeding channels as appropriate. The solution-feeding channels, mononuclear cell separating unit 203, mononuclear cell purifying filter 210, factor introducing device 213, initializing culturing vessel 219, first amplifying culturing vessel 232, second amplifying culturing vessel 240 and solution exchanger 247 are housed in a cassette-like case 259, for example, made of a resin or the like. The case 259 is made of a sterilizable heat-resistant material, for example. The case 259 is adjusted to an environment suitable for cell culture, such as 37° C., 5% $CO_2$ concentration. The solution-feeding channel through which the culture medium flows is made of a $CO_2$-permeable material, for example. However, the case 259 is not limited to a cassette-like form. It may instead be a flexible bag, for example. The solution-feeding channels, mononuclear cell separating unit 203, mononuclear cell purifying filter 210, factor introducing device 213, initializing culturing vessel 219, first amplifying culturing vessel 232, second amplifying culturing vessel 240 and solution exchanger 247 may also be housed in a plurality of separate cases.

The case 259 is disposed in the enclosure 200. The pump, blood storing unit 201, separating agent storing device 205, factor storing device 214, blood cell culture medium storing unit 220, stem cell culture medium storing unit 223, waste liquid storage section 228, cryopreservation vessel 255, low-temperature repository 256 and liquid nitrogen repository 257 are disposed inside the enclosure 200 and outside of the case 259.

The case 259 and enclosure 200 comprise engaging parts that mutually engage, for example. The case 259 will thus be disposed at a prescribed location in the enclosure 200. Furthermore, the pump, blood storing unit 201, separating agent storing device 205, factor storing device 214, blood cell culture medium storing unit 220, stem cell culture medium storing unit 223, waste liquid storage section 228, cryopreservation vessel 255, low-temperature repository 256 and liquid nitrogen repository 257 are also disposed at prescribed locations in the enclosure 200. When the case 259 is disposed at a prescribed location in the enclosure 200, the solution-feeding channels in the case 259 are in contact with the pump, blood storing unit 201, separating agent storing device 205, factor storing device 214, blood cell culture medium storing unit 220, stem cell culture medium storing unit 223, waste liquid storage section 228, cryopreservation vessel 255, low-temperature repository 256 and liquid nitrogen repository 257.

For example, the case 259 and its contents may be disposable, and upon completion of freezing of the cell masses, they may be discarded and exchanged with new ones. Alternatively, when the case 259 and its contents are to be reused, an identifier such as a barcode may be attached to the case 259 to manage the number of times used, etc.

With the stem cell production system of the embodiment described above, it is possible to automatically produce cryopreserved stem cells such as iPS cells from blood.

Other Embodiments

An embodiment of the invention has been described above, but the description and pertinent drawings that are intended merely to constitute a part of the disclosure are not to be understood as limiting the invention. Various alternative embodiments, embodiments and operating technologies will be readily apparent to a person skilled in the art from this disclosure. For example, the factor introducing device 30 may induce the cells not by electroporation or RNA lipofection, but rather by a virus vector such as retrovirus, lentivirus or Sendai virus, or by transfection using plasmids, or by protein transfection. Also, the preintroduction cell solution-feeding channel 20, introduced cell solution-feeding channel 31, cell mass solution-feeding channel 51, amplifying culturing solution-feeding channel 71, cell mass solution-feeding channel 72 and pre-packaging cell channel 91 may be provided on a substrate by a microfluidics technique. Thus, it will be understood that the invention encompasses various embodiments not described herein.

Example 1

(Preparation)

Human blood cells were acquired from a healthy adult male. There were also prepared modified mRNA (TriLink), a non-adherent dish, a 15 mL tube, a 50 mL tube, Ficoll, a Cytoflowmeter (BD), anti-CD34 antibody (Miltenyi Biotec), anti-CD3 antibody (Miltenyi Biotec), MACS® buffer (Miltenyi Biotec), T cell culture medium, low serum culture medium (Opti-MEM®, Gibco), siRNA introducing reagent (Lipofectamine®, RNAiMAX, ThermoFisherScience) and anti-TRA-1-60 antibody (BD).

The T cell (CD3-positive cell) culture medium was a liquid mixture of the following culture medium A and culture medium B. Culture medium A as a liquid mixture of 15 mL of X vivo-10 (Lonza, 04-743Q) and IL-2 (10 µg/mL). Culture medium B was prepared by mixing X vivo-10 and 50 µL of Dynabeads CD3/CD28 (Life Technologies, 111-31D) in a 1.5 mL tube, vortexing the mixture for 5 seconds, allowing spin-down, stationing the mixture in a DynaMag-2 (Thermo fisher Science), and removing the supernatant after one minute of stationing.

There was additionally prepared a blood cell culture medium (blood stem/precursor cell medium) by adding 10 µL of IL-6 (100 µg/mL), 10 µL of SCF (300 µg/mL), 10 µL of TPO (300 µg/mL), 10 µL of Flt3 ligand (300 µg/mL) and 10 µL of IL-3 (10 µg/mL) to 10 mL of serum-free medium (StemSpan H3000, STEMCELL Technologies).

There were further prepared an OCT3/4 mRNA-containing solution, SOX2 mRNA-containing solution, KLF4 mRNA-containing solution, c-MYC mRNA-containing solution, LIN28A mRNA-containing solution and green fluorescent protein (GFP) mRNA-containing solution, each to a concentration of 100 ng/µL. Next, 385 µL of the OCT3/4 mRNA-containing solution, 119 µL of the SOX2 mRNA-containing solution, 156 µL of the KLF4 mRNA-containing solution, 148 µL of the c-MYC mRNA-containing solution, 83 µL of the LIN28A mRNA-containing solution and 110 µL of the GFP mRNA-containing solution were mixed to obtain an initializing factor mixture. The obtained initializing factor mixture was dispensed into 1.5 mL-volume RNase-Free tubes (Eppendorf Tube®, Eppendorf AG) at 50 µL Each, and Preserved in a Freezer at −80° C.

(Preparation of Mononuclear Cells)

A centrifuge was set to 18° C. Blood was sampled in amounts from 5 mL to 50 mL, EDTA was added to the blood, and each mixture was gently mixed. Also, medium for human lymphocyte separation Ficoll-Paque PREMIUM, GE Healthcare, Japan) was dispensed into two 15 mL tubes at 5 mL each. After adding 5 mL of PBS to the blood for dilution, 5 mL of each was overlaid onto the human lymphocyte separation medium in the tubes. During this time, the diluted blood was slowly added onto the medium while causing it to slide on the tube wall, so as not to disturb the interface.

The solutions in the tubes were centrifuged at 400×g, 18° C. for 30 minutes. Acceleration and deceleration were carried out slowly during the procedure. After centrifugation, a white cloudy intermediate layer appeared in the tube. The white cloudy intermediate layer includes mononuclear cells. The white cloudy intermediate layer in each tube was slowly collected with a Pipetman and transferred to a new 15 mL tube. The lower layer was not handled during this time. Approximately 1 mL of the white cloudy intermediate layer could be collected from each tube. The intermediate layers of two tubes were combined and transferred to a single tube.

After adding 12 mL of PBS to the collected mononuclear cells, the solution was further centrifuged at 200×g, 18° C. for 10 minutes. Next, an aspirator was used to remove the supernatant of the solution by aspiration, and 3 mL of serum-free hematopoietic cell culture medium of known composition (X-VIVO® 10, Lonza) was added forming a suspension, to obtain a mononuclear cell suspension. A 10 µL portion of the mononuclear cell suspension was stained with Trypan blue and the count was determined with a hemocytometer.

(Separation of CD34 or CD3-Positive Cells)

Reaction was performed between $1 \times 10^7$ mononuclear cells and CD34 antibody or CD3 antibody for 15 minutes in 100 µL of solution at 4° C. Following the reaction, 5 mL of MACS® buffer (Miltenyi Biotec) was added to the solution, and centrifugation was performed at 270 g. After centrifugation, the supernatant was removed and 1 mL of MACS buffer was added. Next, utilizing the separation program of an automatic magnetic cell separator (autoMACS, Miltenyi Biotec), CD34-positive cells and CD3-positive cells were separated from among the mononuclear cells.

(Culturing of Separated Cells)

After suspending $5 \times 10^6$ of the separated mononuclear cells in 1 mL of T cell culture medium or blood stem/precursor cell culture medium, they were seeded in a 12-well plate and cultured. The culturing conditions were 5% $CO_2$ concentration, 19% oxygen concentration, 37° C. temperature.

(Lipofection of Initializing Factor)

A first mixture was prepared by mixing 100 μL of low serum culture medium (Opti-MEM®, Gibco) and 25 μL of initializing factor mixture. A second mixture was also prepared by mixing 112.5 μL of low serum culture medium (Opti-MEM®, Gibco) and 12.5 μL of siRNA introducing reagent (Lipofectamine®, RNAiMAX, ThermoFisher-Science). Next, the first mixture and second mixture were combined and allowed to stand at room temperature for 15 minutes, to prepare a lipofection reaction mixture.

After gently adding 60 μL of the obtained lipofection reaction mixture to the 12-well plate in which the mononuclear cells were being cultured, the mononuclear cells were then cultured in a feeder-free manner at 37° C. for 18 hours. The culturing conditions were 5% $CO_2$ concentration, 19% oxygen concentration, 37° C. temperature. The mononuclear cell density upon addition of the lipofection reaction mixture was $3 \times 10^6$. After 18 hours, the mononuclear cells were collected in a 15 mL tube and centrifuged at 300 g, and the supernatant was removed. Next, 1.25 mL of CD34 blood cell culture medium was added to a 15 mL tube, the mononuclear cell suspension was returned to the same 12-well plate, and feeder-free culturing of the mononuclear cells was carried out overnight at 37 degrees. The culturing conditions were 5% $CO_2$ concentration and 19% oxygen concentration. The steps described above were repeated once every 2 days for 7 days.

(Confirmation of GFP Expression)

Figure 35:
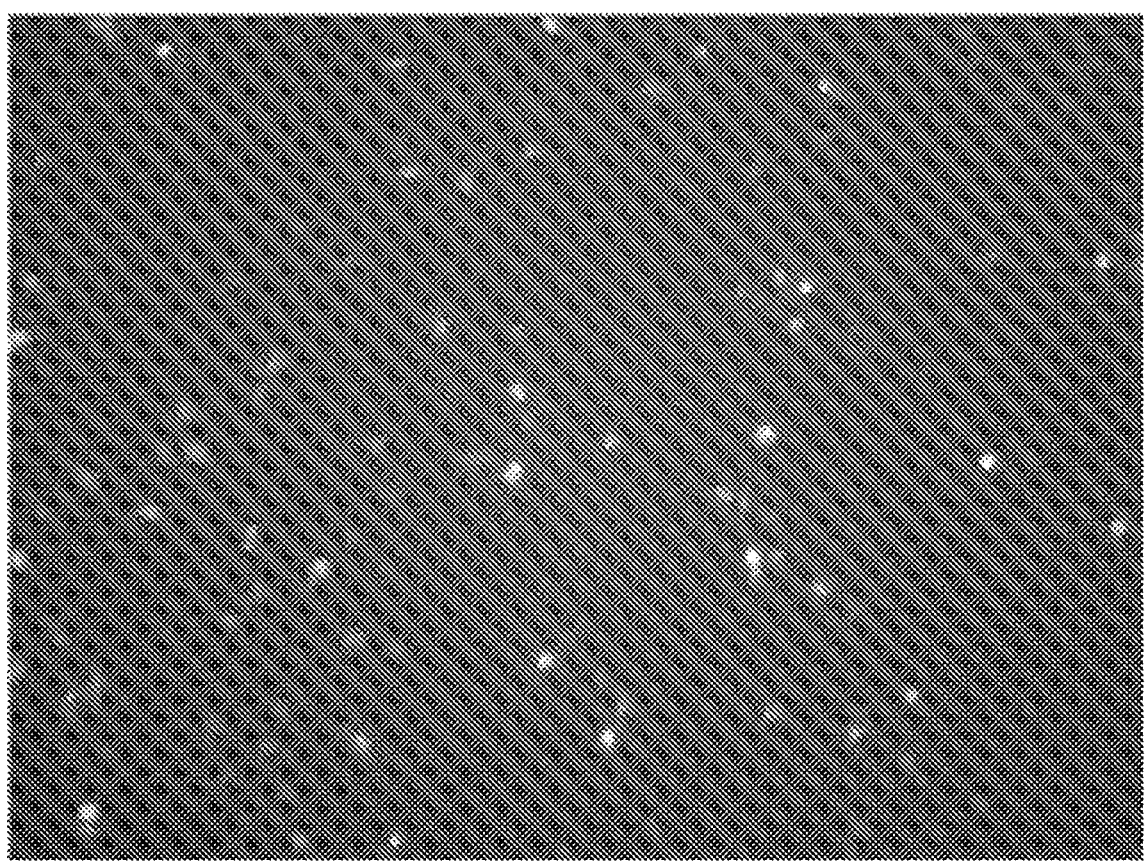
FIG. 35 is a fluorescent microscope photograph for Example 1.

On the 7th day after the start of lipofection, the density of cells after a total of 4 lipofections was $3 \times 10^6$. When a portion of the cells was removed from the 12-well plate and GFP expression was examined with a fluorescent microscope, expression of GFP was confirmed, as shown in FIG. 35. This confirmed that mRNA had been transfected in the mononuclear cells, and that protein had been synthesized from the transfected mRNA.

(Confirmation of TRA-1-60 Expression)

On the 7th day after the start of lipofection, a portion of the cells were removed from the 12-well plate, and the removed cells were stained with antibody for TRA-1-60 as a surface antigen specifically expressed on the iPS cells that had begun to be initialized, the antibody being labeled with Allophycocyanin (APC) fluorescent dye. Next, the ratio of TRA-1-60-positive cells was determined with a fluorescence activated cell sorter (FACS®, BD), to confirm that reprogramming of the cells had been initiated, iPS cell genes had been expressed and iPS cells had emerged.

Figure 36:
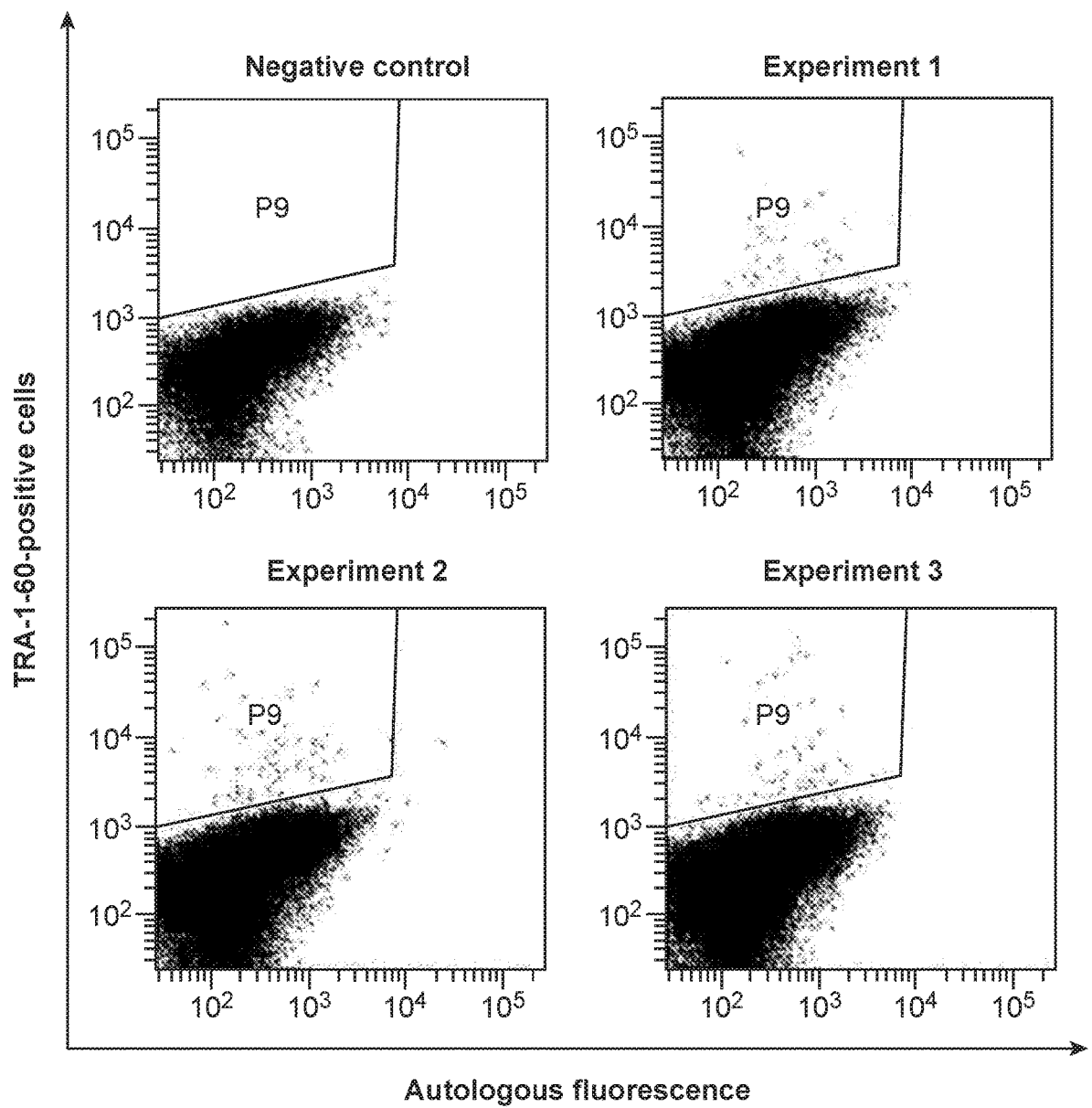
FIG. 36 is a graph showing analysis results for Example 1, using a fluorescence activated flow cytometer.

As shown in FIG. 36, a dot plot was drawn with autologous fluorescence intensity on the x-axis and fluorescent labeled anti-TRA-1-60 antibody fluorescence intensity on the y-axis. No TRA-1-60-positive cells were detected in a negative control without gene introduction. In contrast, TRA-1-60-positive cells were detected in Experiments 1, 2 and 3. Experiment 1 represents the results of induction from all of the mononuclear cells without separation by markers, Experiment 2 represents the results of induction from cells separated as CD3-positive, and Experiment 3 represents the results of induction from cells separated as CD34-positive. It was thus demonstrated that iPS cells can be induced by using lipofection of initializing factor RNA to introduce the initializing factor into blood-derived cells.

Example 2

A bFGF-containing human iPS culture medium was prepared by mixing 500 mL of Primate ES Cell Medium (ReproCELL) and 0.2 mL of bFGF (Gibco PHG0266) at a 10 μg/mL concentration.

Also, deacylated gellan gum (Nissan Chemical Industries, Ltd.) was added to the bFGF-containing human iPS culture medium to a concentration of 0.02 wt %, to prepare a bFGF-containing human iPS gel medium. In addition, 5 mL of trypsin at 2.5 wt % concentration, 5 mL of collagenase IV at 1 mg/mL concentration, 0.5 mL of $CaCl_2$) at 0.1 mol/L concentration, 10 mL of KnockOut Serum Replacement® (Invitrogen 10828-028) and 30 mL of purified water were mixed to prepare a dissociation solution, commonly known as CTK solution.

After adding 300 μL of the CTK solution to a 6-well dish (Thermoscientific 12-556-004) in which iPS cells were being cultured on feeder cells, the mixture was incubated for 3 minutes in a $CO_2$ incubator. After 3 minutes, the dish was removed from the incubator, detachment of the feeder cells alone was confirmed, and an aspirator was used to remove the CTK solution. After removing the CTK solution, 500 μL of PBS (Santa Cruz Biotech sc-362183) was added to the 6-well dish to rinse the iPS cells, and then the PBS was removed from the 6-well dish and 0.3 mL of dissociation solution (Accutase®) was added to the 6-well dish, which was placed in a $CO_2$ incubator and incubated for 5 minutes. Next, 0.7 mL of bFGF-containing iPS culture medium was added to the 6-well dish and the iPS cells were suspended until single cells were obtained.

After suspension of the iPS cells, 4 mL of bFGF-containing human iPS culture medium was added to a 15 mL centrifugation tube, and the iPS cell suspension was centrifuged at 270 g using a centrifuge. After centrifugation, the supernatant was removed, 1 mL of bFGF-containing human iPS culture medium was added to a 15 mL centrifugation tube, and a hemocytometer was used to calculate the cell count. After cell counting, $5 \times 10^5$ of iPS cells each were seeded in a 15 mL Falcon Tube® (Corning 352096) or a non-adherent dish, and suspension culture was carried out without agitation.

A 2 mL portion of bFGF-containing human iPS gel medium was used in the 15 mL tube. A 2 mL portion of non-gelled bFGF-containing human iPS culture medium was used in the non-adherent dish. ROCK inhibitor (Selleck S1049) was added at 10 μmol/L to each medium. Thereafter, 500 μL of bFGF-containing human iPS gel medium was added each day to the 15 mL tube and non-adherent dish and 500 μL of bFGF-containing human iPS culture medium was added each day to the non-adherent dish. Also, ROCK inhibitor was added to the 15 mL tube and non-adherent dish each day to a final concentration of 10 μmol/L, and suspension culture was continued for 7 days.

Figures 37A, 37B:
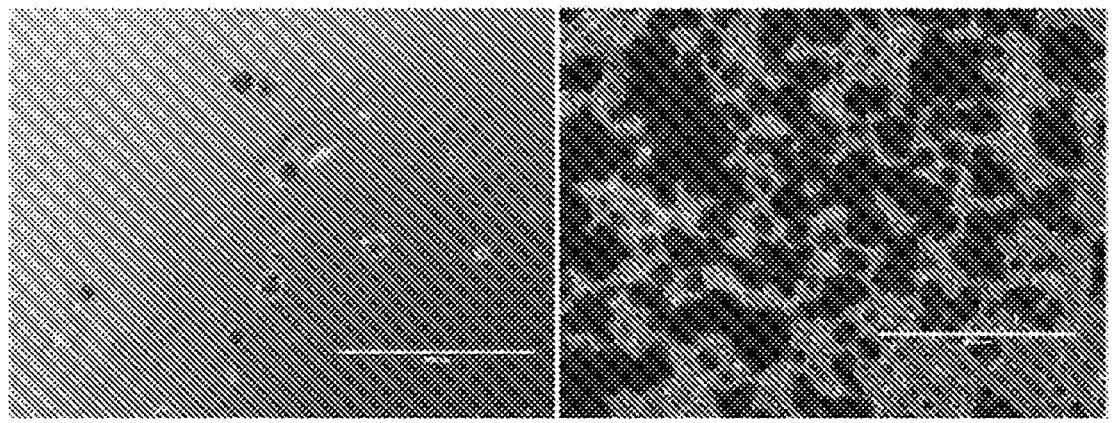
FIGS. 37A and 37B are a pair of photographs of iPS cells colonies, for Example 2.
Figure 38A:
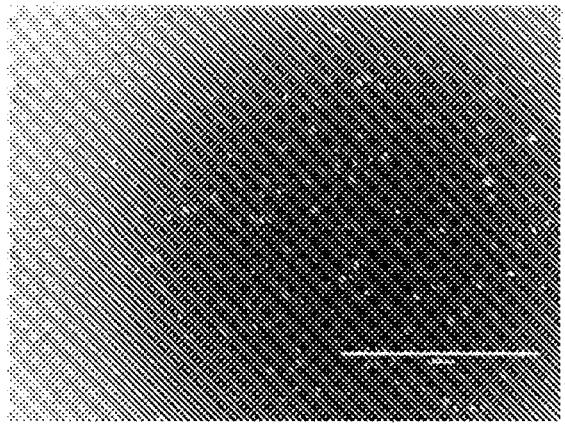
FIGS. 38A and 38B are a pair of photographs of iPS cells colonies, for Example 2.
Figure 38B:
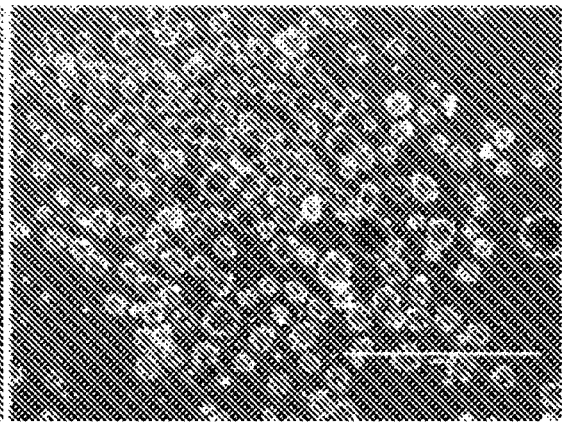

The results are shown in FIGS. 37A and 37B. As shown in FIG. 37B, when iPS cells were cultured in the non-adherent dish using non-gelled bFGF-containing human iPS culture medium, notable aggregation of the iPS cell colonies was observed. In contrast, as shown in FIG. 37A, when iPS cells were cultured using bFGF-containing human iPS gel medium in the 15 mL tube, no such conspicuous aggregation was observed. FIG. 38A is a photograph on the 1st day after culturing of iPS cells using bFGF-containing human iPS gel medium in the 15 mL tube, and FIG. 38B is a photograph on the 9th day after culturing of iPS cells using bFGF-containing human iPS gel medium in the 15 mL tube. The photographs of FIG. 38A and FIG. 38B confirmed colony formation without aggregation between iPS cells of different lines.

Figures 39A, 39B:
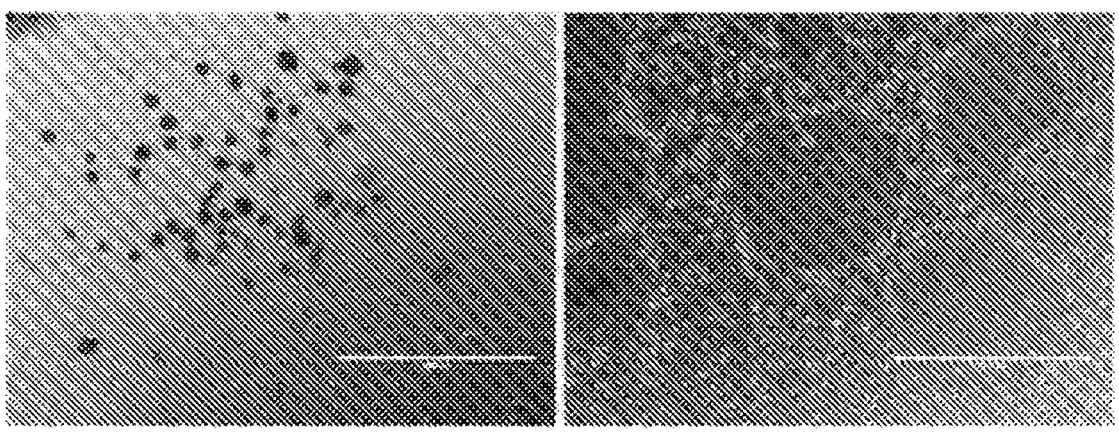
FIGS. 39A and 39B are a pair of photographs of iPS cells colonies, for Example 2.
Figure 40:
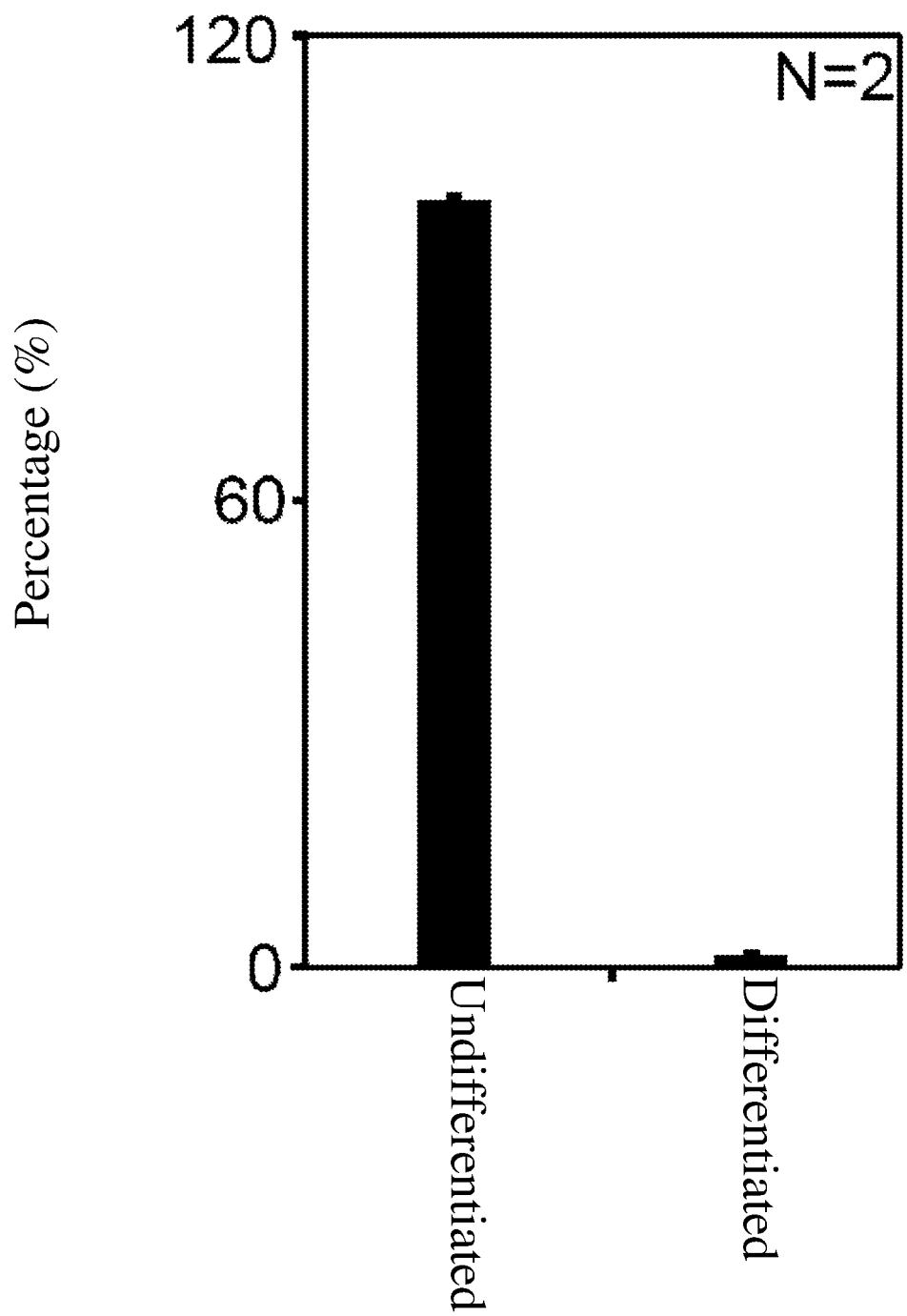
FIG. 40 is a graph showing the state of differentiation of iPS cells colonies, for Example 2.

FIG. 39A is a photograph immediately before reseeding of the iPS cell colonies that had been suspension cultured for 7 days in gel medium, onto feeder cells. FIG. 39B is a photograph taken when confirming the forms of the colonies after 3 days. As shown in FIG. 40, the results confirmed that at least 95% of the colonies were undifferentiated. It was thus demonstrated that iPS cells can be cultured in gel medium while maintaining their undifferentiated state.

Example 3

The same bFGF-containing human iPS culture medium and bFGF-containing human iPS gel medium were prepared as in Example 2. After adding 300 μL of the CTK solution to a 6-well dish in which iPS cells were being cultured on feeder cells, the mixture was incubated for 3 minutes in a $CO_2$ incubator. After 3 minutes, the dish was removed from the incubator, detachment of the feeder cells alone was confirmed, and an aspirator was used to remove the CTK solution. After removing the CTK solution, 500 μL of PBS was added to the dish to rinse the iPS cells, and then the PBS was removed from the dish and 0.3 mL of Accumax was added to the dish, after which the dish was placed in a $CO_2$ incubator and incubated for 5 minutes. Next, 0.7 mL of bFGF-containing iPS culture medium was added to the dish and the iPS cells were suspended until single cells were obtained.

After suspension of the iPS cells, 4 mL of bFGF-containing human iPS culture medium was added to a 15 mL centrifugation tube, and the iPS cell suspension was centrifuged at 270 g using a centrifuge. After centrifugation, the supernatant was removed, 1 mL of bFGF-containing human iPS culture medium was added to a 15 mL centrifugation tube, and a hemocytometer was used to calculate the cell count. The cells were counted, and then $5 \times 10^5$ iPS cells were seeded in each 15 mL tube and suspension culture was carried out without agitation.

A 2 mL portion of bFGF-containing human iPS gel medium was used in a 15 mL tube. ROCK inhibitor was added at 10 μmol/L to each medium. A 500 μL portion of bFGF-containing human iPS gel medium was added to the 15 mL tube each day thereafter. A 500 μL portion of gel medium includes 0.5 μL of ROCK inhibitor. As a control, iPS cells were also suspension cultured for 7 days under the same conditions, but without addition of a ROCK inhibitor.

Figure 41A:
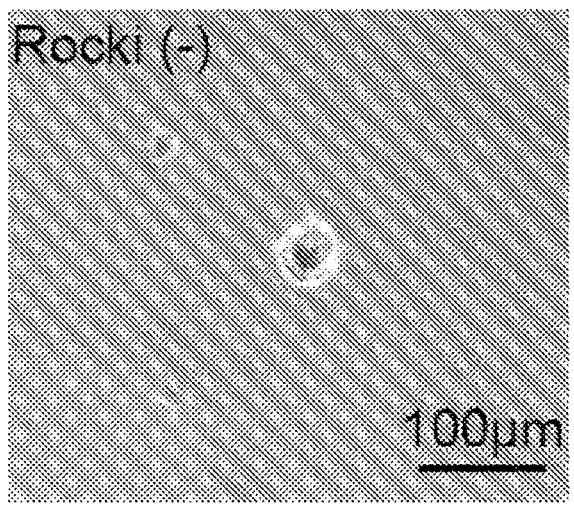
FIGS. 41A and 41B are a pair of photographs of iPS cells colonies, for Example 3.
Figure 41B:
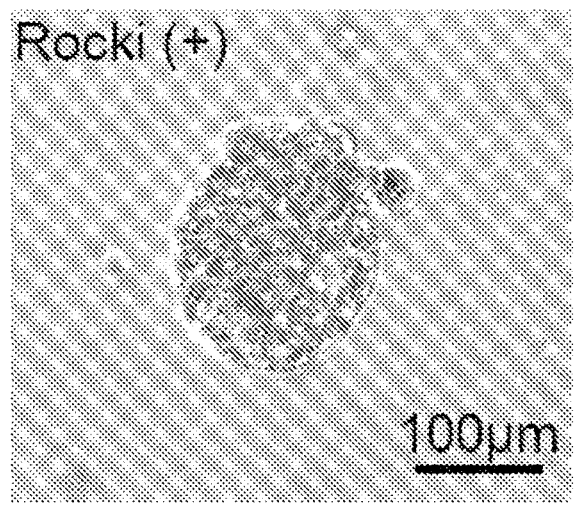

As shown in FIG. 41A, no iPS cell colonies formed when a ROCK inhibitor was not added to the bFGF-containing human iPS culture medium. In contrast, as shown in FIG. 41B, iPS cell colonies formed when a ROCK inhibitor was added to the bFGF-containing human iPS culture medium. These results demonstrated that a ROCK inhibitor is effective for suspension culturing of iPS cells from single cells.

Example 4

Figure 42:
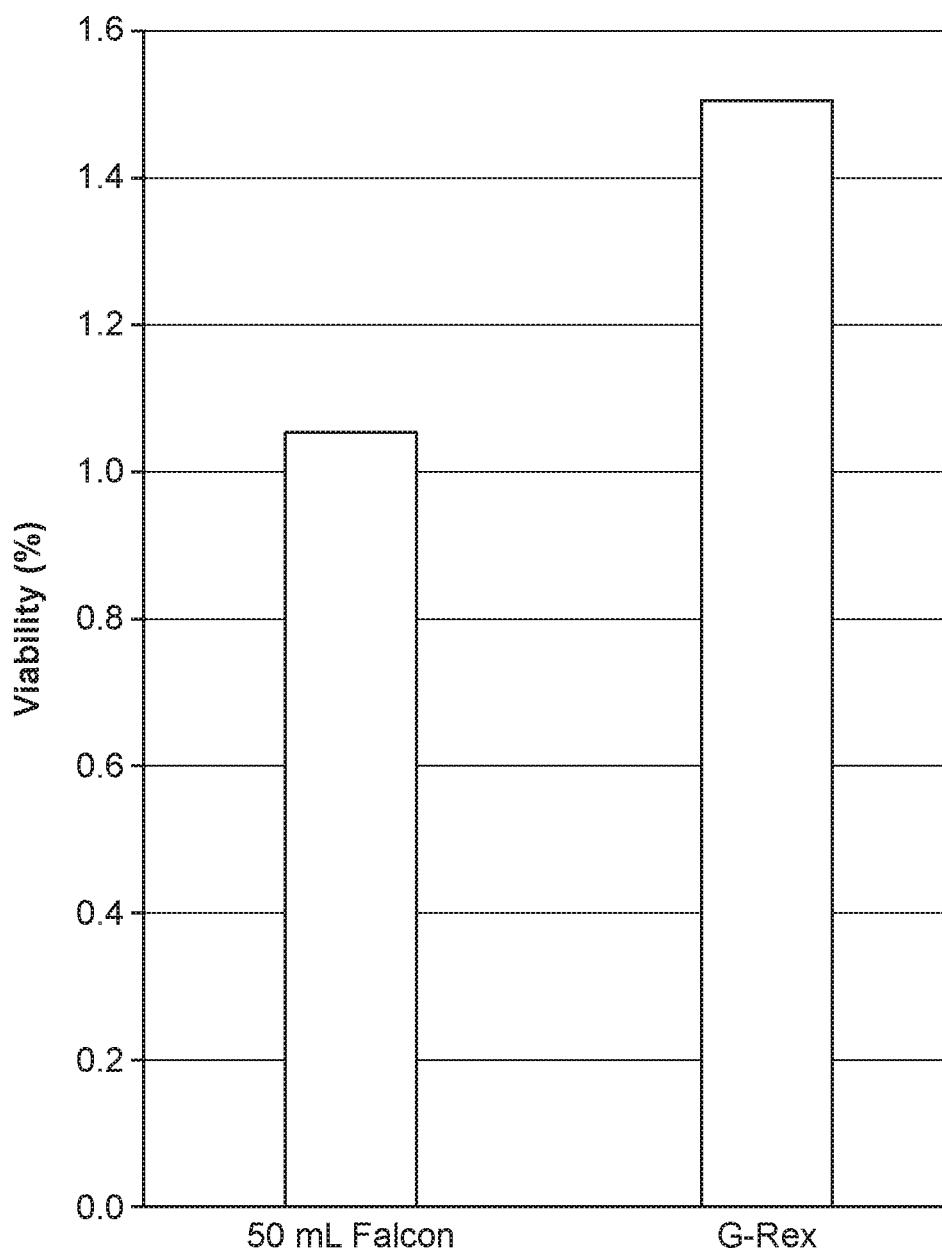
FIG. 42 is a graph showing the results for Example 4.
Figure 43A:
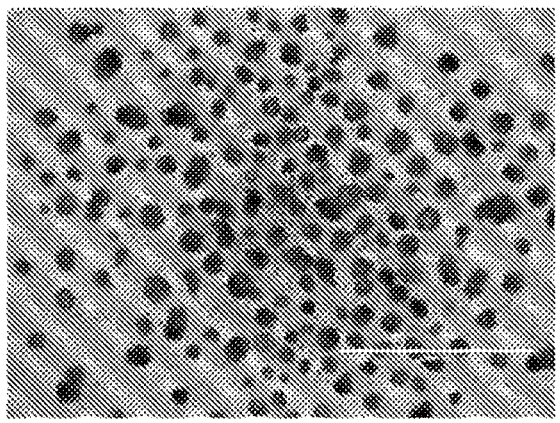
FIGS. 43A to 43C are a set of photographs of iPS cell masses, for Example 5.
Figure 43B:
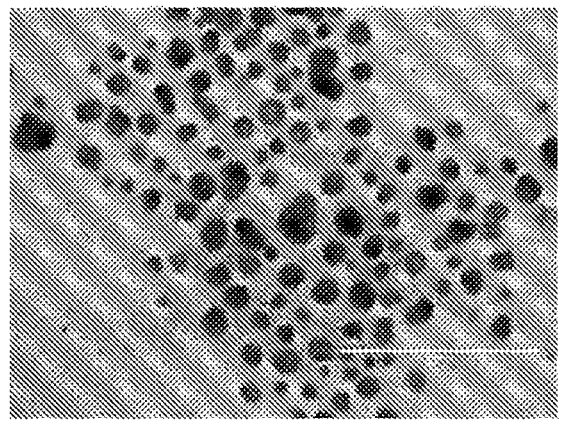
Figure 43C:
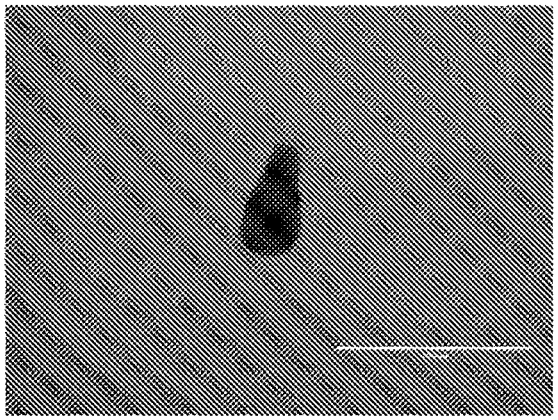
Figure 44:
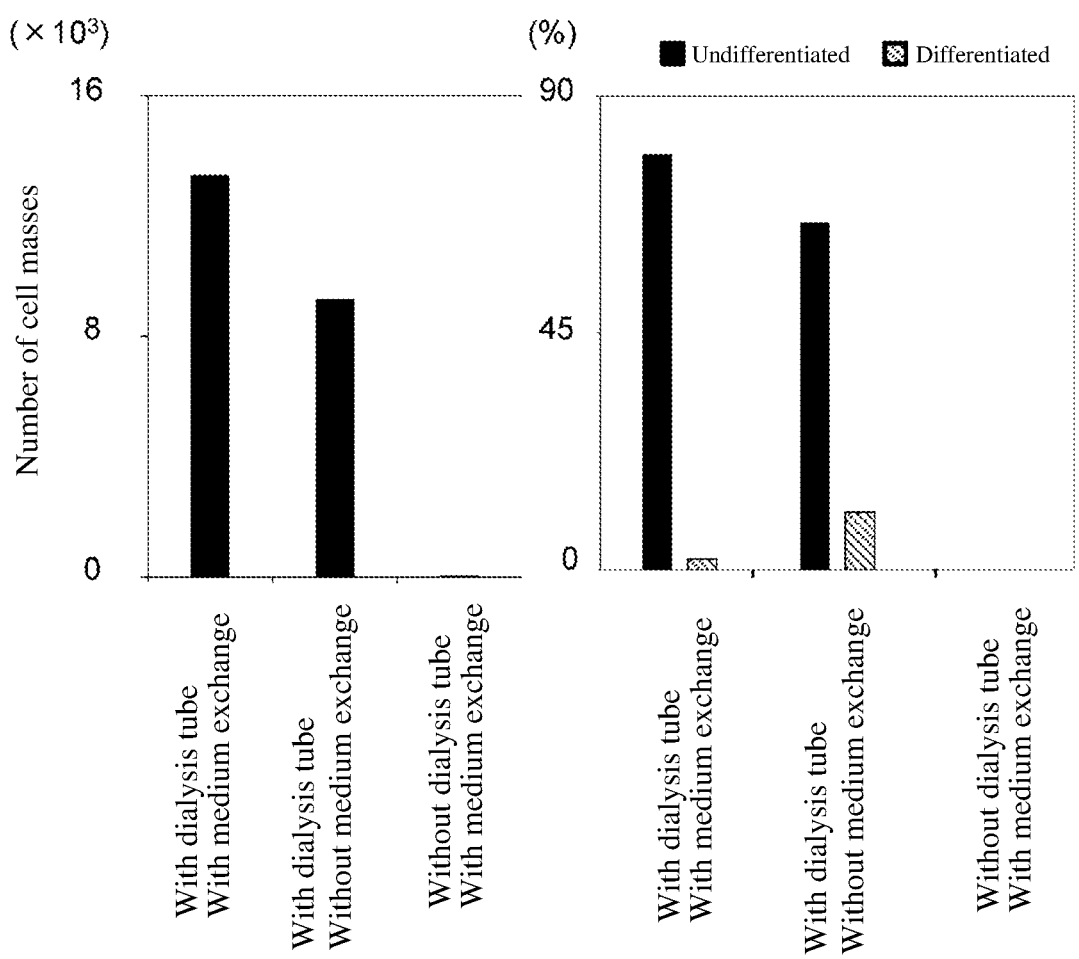
FIG. 44 is a pair of graphs showing the results for Example 5.

Using a $CO_2$-non-permeable vessel, Falcon 50 mL Conical Tube®, and a $CO_2$-permeable vessel, G-Rex® (Wilson Wolf), as dialysis tube-housing vessels, cells were suspension cultured under the same conditions, other than the vessels. As a result, as shown in FIG. 42, culturing using the $CO_2$-permeable vessel produced a higher cell viability.

Example 5

Gel medium containing iPS cells was added to each of two dialysis modules (Spectrum G235035) comprising a dialysis tube with a 100 kDa molecular cutoff. The dialysis modules were each placed in a 50 mL centrifugation tube, and gel medium was placed around the dialysis tubes in the centrifugation tubes. The gel medium containing the iPS cells was also directly placed in a separate 50 mL centrifugation tube.

Next, a pump was connected to one of the centrifugation tubes of the two centrifugation tubes in which dialysis tubes had been placed, as shown in FIG. 6, and the gel medium in the centrifugation tube was continuously exchanged for several days. The gel medium was stored at 4° C., and set so as to be at 37° C. when reaching the centrifugation tube. No pump was connected to the other centrifugation tube of the two centrifugation tubes in which a dialysis tube had been placed, and the gel medium in the centrifugation tube was not exchanged. The gel medium was also not exchanged in the centrifugation tube in which a dialysis tube had not been placed.

When the cells cultured in each vessel were observed after culturing for the same period, numerous cell masses formed when the cell masses were cultured in a dialysis tube and the gel medium surrounding the dialysis tube was continuously exchanged with a pump, as shown in FIGS. 43A to 43C and FIG. 44. The number of differentiated cells was also very low. However, when the cell masses were cultured in a dialysis tube and the gel medium surrounding the dialysis tube was not continuously exchanged with a pump, the number of cell masses was low and the number of differentiated cells increased. Moreover, when the cell masses were cultured without using a dialysis tube and the gel medium was not continuously exchanged with a pump, virtually no cell masses were formed.

EXPLANATION OF SYMBOLS

10 Separating device
20 Preintroduction cell solution-feeding channel
21 Inducing factor solution-feeding mechanism
30 Factor introducing device
31 Introduced cell solution-feeding channel
40 Cell mass preparation device
50 Initializing culturing apparatus
51 Cell mass solution-feeding channel
60 Dissociating mechanism
61 Terminal block
61a Recess
61b Protrusion
61c Large pore size section
62 Connecting block
62a Recess
62b Protrusion
62c Large pore size section
62d Small pore size section
62e Large pore size section
63 Tip block
63a Recess
63b Nozzle section
63c Large pore size section
63d Small pore size section
64 Insertion nozzle
65a Large pore size section
65b Small pore size section
66a Insertion section
66b Insertion section
70 Amplifying culturing apparatus
71 Amplifying culturing solution-feeding channel
72 Cell mass solution-feeding channel 75 Dialysis tube
76 Vessel
77 Supply culture medium solution-feeding pump
78 Solution-feeding tube
79 Waste liquid tube
80 Dissociating mechanism
90 Cell mass transport mechanism
91 Pre-packaging cell channel
100 Packaging device
101 Solution exchanger
102 Filter
103 Solution-feeding channel
104 Solution-feeding channel
105 Discharge channel
106 Discharge channel
110 Cryopreservation liquid solution-feeding mechanism
171 Initializing culturing photographing device
172 Telecentric lens
173 Cell observation illumination light source
174 Medium observation illumination light source
200 Enclosure
201 Blood storing unit
202 Blood solution-feeding channel
203 Mononuclear cell separating unit
204 Pump
205 Separating agent storing device
206 Solution-feeding channel
207 Pump
208 Mononuclear cell solution-feeding channel
209 Pump
210 Mononuclear cell purifying filter
212 Pump
213 Factor introducing device
214 Factor storing device
215 Factor solution-feeding channel
216 Pump
217 Introduced cell solution-feeding channel
218 Pump
219 Initializing culturing vessel
220 Blood cell culture medium storing unit
221 Culture medium solution-feeding channel
222 Pump
223 Stem cell culture medium storing unit
224 Culture medium solution-feeding channel
224 Pump
225 Pump
226 Waste liquid solution-feeding channel
227 Pump
228 Waste liquid storage section
229 Introduced cell solution-feeding channel
230 Pump
231 Cell mass dissociator
232 Amplifying culturing vessel
233 Culture medium solution-feeding channel
234 Pump
235 Waste liquid solution-feeding channel
236 Pump
237 Introduced cell solution-feeding channel
238 Pump
239 Cell mass dissociator
240 Amplifying culturing vessel
241 Culture medium solution-feeding channel
242 Pump
243 Waste liquid solution-feeding channel
244 Pump
245 Introduced cell solution-feeding channel
246 Pump
247 Solution exchanger
248 Waste liquid solution-feeding channel
249 Pump
250 Cryopreservation liquid storing device
251 Solution-feeding channel
252 Pump
253 Solution-feeding channel
254 Pump
255 Cryopreservation vessel
256 Low-temperature repository
257 Liquid nitrogen repository
258 Solution-feeding channel
259 Cold storage section
259 Case
271 Sensor
272 Thermometer
301 Bag
302 Bag
401 Input device
402 Output device
403 Relationship memory unit
500 CPU
501 Image processor
511 Outline defining unit
512 Cell evaluating unit
513 Statistical processor
514 Density calculating unit
515 Culture medium evaluating unit

The invention claimed is:

1. A method for producing an induced pluripotent stem cell comprising:
    transporting a cell-containing solution comprising cells through a preintroduction cell solution-feeding channel to a factor introducing device connected to the preintroduction cell solution-feeding channel,
    transporting pluripotency inducing factors from a factor storing unit that preserves the pluripotency inducing factors to the factor introducing device through a factor solution-feeding channel,
    introducing the pluripotency inducing factors into the cells to prepare cells comprising factor-introduced cells in the factor introducing device, and
    culturing the factor-introduced cells to prepare a cell mass or a plurality of cell masses comprising induced pluripotent stem cells in a cell mass preparation device,
    wherein the cell mass preparation device comprises an initializing culturing apparatus that cultures the factor-introduced cells, and
    wherein the factor introducing device is non-rotatable.

2. The method according to claim 1, wherein the cell mass preparation device further comprises an amplifying culture apparatus that amplifies the factor-introduced cells, and
    wherein the method further comprises amplifying culturing the factor-introduced cells in the amplifying culture apparatus.

3. The method according to claim 1, wherein a pump feeds a solution containing the pluripotency inducing factors from the factor storing unit to the factor introducing device through the factor solution-feeding channel.

4. The method according to claim 1, wherein the inducing factors are introduced into the cells by RNA lipofection in the factor introducing device.

5. The method according to claim 1, wherein the inducing factors comprise at least one selected from the group consisting of DNA, RNA, and protein.

6. The method according to claim 1, wherein the inducing factors are incorporated into a vector.

7. The method according to claim 6, wherein the vector comprises Sendai virus vector.

8. The method according to claim 1, wherein the factor introducing device further comprises a pump for streaming liquid comprising the inducing factors in the factor solution-feeding channel, and
wherein the pump is a diaphragm pump, a tubing pump, or a peristaltic pump.

9. The method according to claim 1, wherein the initializing culturing apparatus comprises a suspension culture vessel that comprises:
a semipermeable membrane in which the factor-introduced cells and culture medium have been inserted; and
a vessel in which the semipermeable membrane is placed, and
the culture medium is situated around the periphery of the semipermeable membrane.

10. The method according to claim 1, further comprising delivering the factor-introduced cells from the factor introducing device to the initializing culturing apparatus through a cell solution-feeding channel.

11. The method according to claim 2, wherein the amplifying culturing apparatus comprises:
a suspension culture vessel that comprises a semipermeable membrane in which the cell mass or the plurality of cell masses and a medium have been inserted; and
a vessel in which the semipermeable membrane is placed, and
the culture medium is situated around the periphery of the semipermeable membrane.

12. The method according to claim 2, further comprising delivering the factor-introduced cells from the initializing culturing apparatus to the amplifying culturing apparatus through a cell solution-feeding channel.

13. The method according to claim 2, further comprising connecting the inside of a semipermeable membrane of a suspension culture vessel of the initializing culturing apparatus with the inside of a semipermeable membrane of a suspension culture vessel of the amplifying culturing apparatus by a cell solution-feeding channel,
wherein the factor-introduced cells and a medium are entered into the semipermeable membrane of the suspension culture vessel of the initializing culturing apparatus, and
wherein the cell mass or the plurality of cell masses and a medium are entered into the semipermeable membrane of the suspension culture vessel of the amplifying culturing apparatus.

14. The method according to claim 2, wherein the cell mass preparation device further comprises:
a first dissociator that dissociates the cell mass or the plurality of cell masses comprising induced pluripotent stem cells into at least one first cell mass; and
a second dissociator that dissociates the cell mass or the plurality of cell masses comprising induced pluripotent stem cells into at least one second cell mass, the at least one second cell mass comprising or consisting of cells that have been amplified.

15. The method according to claim 14, wherein the first dissociator is provided in a cell solution-feeding channel that connects the initializing culturing apparatus to the amplifying culturing apparatus.

16. The method according to claim 14, further comprising dissociating the cell mass or the plurality of cell masses into single cells with at least one of the first or second dissociators.

17. The method according to claim 14, wherein at least one of the first or second dissociators comprise a dissociator having a through-hole in the interior, the through-hole having large pore size sections and small pore size sections connecting with the large pore size sections,
wherein the large pore size sections and small pore sections alternate, and the cell mass or the plurality of cell masses flows through the through-hole.

18. The method according to claim 14,
at least one of the first or second dissociators comprise a connecting block with a through-hole provided in the interior of the connecting block, the connecting block comprising a first edge and a second edge,
wherein a recess is provided at the first edge of the connecting block and a protrusion is provided at the second edge of the connecting block, and
wherein protrusions engage with recesses of adjacent connecting blocks, and
the through-hole has a first large pore size section that connects with the recess, a small pore size section that connects with the first large pore size section and has a smaller pore size than the first large pore size section, and a second large pore size section that connects with the small pore size section, the second large pore size section having a larger pore size than the small pore size section and an opening at the tip of the protrusion, and
the at least one first cell mass or the at least one second cell mass flows through the through-hole.

19. The method according to claim 1, further comprising packaging the cell mass or the plurality of cell masses in a packaging device.

20. The method according to claim 19, wherein the packaging device freezes the cell mass or the plurality of cell masses.

21. The method according to claim 1, wherein a solution exchanger is connected to the cell mass preparation device or the initializing culturing apparatus, the solution exchanger comprising:
a tubular component;
a liquid permeable filter disposed inside the tubular component; and
a cell mass introduction hole disposed inside the tubular component for introduction of solution from the cell mass preparation device or the initializing culturing apparatus onto the liquid permeable filter;
an exchange solution introduction hole for introduction of exchange solution onto the liquid permeable filter;
a cell mass outflow hole for outflow of the exchange solution including the onto the liquid permeable filter; and
a waste liquid outflow hole through which the solution that has permeated the liquid permeable filter flows out.

22. The method according to claim 1, further comprising separating cells from blood by a separating device,
wherein the separated cells are contained in the cell-containing solution to be transported through the pre-introduction cell solution-feeding channel.

23. The method according to claim 22, wherein the separating device further comprises a mononuclear cell purifying filter that purifies mononuclear cells.

24. The method according to claim 2, wherein at least one of the factor introducing device, a suspension culture vessel of the initializing culturing apparatus, or a suspension culture vessel of the amplifying culturing apparatus is housed by a case.

25. The method according to claim 24, wherein at least one of the suspension culture vessel of the initializing culturing apparatus, the suspension culture vessel of the amplifying culturing apparatus, or the case is disposable.

26. The method according to claim 2, wherein at least one selected from the group consisting of the factor introducing device, a suspension culture vessel of the initializing culturing apparatus, and a suspension culture vessel of the amplifying culturing apparatus is housed in each of a plurality of cases.

27. The method according to claim 22, wherein at least one selected from the group consisting of the separating device, the factor introducing device, a suspension culture vessel of the initializing culturing apparatus, and a suspension culture vessel of the amplifying culturing apparatus is housed in each of a plurality of cases.

28. The method according to claim 2, further comprising regulating the temperature of a culture medium in the initializing culturing apparatus and the amplifying culturing apparatus by a temperature regulating device.

29. The method according to claim 1, wherein the inducing factor solution-feeding mechanism, the factor introducing device, and the cell mass preparation device are controlled based on an operation procedure by a server, and the server monitors whether or not the inducing factor solution-feeding mechanism, the factor introducing device, and the cell mass preparation device are running based on the operation procedure and creates a running record of it.

30. The method according to claim 1, wherein the preintroduction cell solution-feeding channel, the factor introducing device, and the cell mass preparation device are housed by an enclosure.

* * * * *